(12) United States Patent
Schouten et al.

(10) Patent No.: US 8,283,523 B2
(45) Date of Patent: *Oct. 9, 2012

(54) GRG23 EPSP SYNTHASES: COMPOSITIONS AND METHODS OF USE

(75) Inventors: Laura Cooper Schouten, Pittsboro, NC (US); Brian Vande Berg, Durham, NC (US); Volker Heinrichs, Raleigh, NC (US)

(73) Assignee: Athenix Corp., Research Triangle Park, NC (US)

( * ) Notice: Subject to any disclaimer, the term of this patent is extended or adjusted under 35 U.S.C. 154(b) by 42 days.

This patent is subject to a terminal disclaimer.

(21) Appl. No.: 12/856,072

(22) Filed: Aug. 13, 2010

(65) Prior Publication Data

US 2011/0232179 A1 Sep. 29, 2011

Related U.S. Application Data

(62) Division of application No. 11/943,801, filed on Nov. 21, 2007, now Pat. No. 7,834,249.

(60) Provisional application No. 60/861,455, filed on Nov. 29, 2006, provisional application No. 60/872,200, filed on Dec. 1, 2006, provisional application No. 60/972,502, filed on Sep. 14, 2007.

(51) Int. Cl.
*C12N 15/82* (2006.01)
*C12N 15/63* (2006.01)
*C12N 15/52* (2006.01)

(52) U.S. Cl. ........... 800/300; 435/252.3; 435/320.1; 435/419; 536/23.2; 800/288; 800/300.1

(58) Field of Classification Search .............. None
See application file for complete search history.

(56) References Cited

U.S. PATENT DOCUMENTS

| | | | |
|---|---|---|---|
| 7,674,958 B2 * | 3/2010 | Peters et al. | 800/300 |
| 2007/0136840 A1 | 6/2007 | Peters et al. | |
| 2007/0294785 A1 | 12/2007 | Heinrichs et al. | |

FOREIGN PATENT DOCUMENTS

| | | |
|---|---|---|
| WO | WO 98/07846 A1 | 2/1998 |
| WO | WO 99/60132 A1 | 11/1999 |
| WO | WO 2005/040344 A2 | 5/2005 |
| WO | WO 2006/110586 A2 | 10/2006 |
| WO | WO 2007/064828 A2 | 7/2007 |

OTHER PUBLICATIONS

Amin, N., et al., "Construction of Stabilized Proteins by Combinatorial Consensus Mutagenesis," *Protein Engineering, Design & Selection*, Nov. 2004, pp. 787-793, vol. 17, No. 11.

Lehmann, M. and M. Wyss, "Engineering Proteins for Thermostability: The Use of Sequence Alignments Versus Rational Design and Directed Evolution," *Current Opinion in Biotechnology*, 2001, pp. 371-375, vol. 12.

Polizzi, K.M., et al., "Structure-guided Consensus Approach to Create a More Thermostable Penicillin G Acylase," *Biotechnol. J.*, May 5, 2006, pp. 531-536.

Rud, I., et al., "A Synthetic Promoter Library for Constitutive Gene Expression in *Lactobacillus plantarum*," *Microbiology*, Apr. 2006, pp. 1011-1019, vol. 152, No. 4.

Padgette, S.R., et al., "Site-directed Mutagenesis of a Conserved Region of the 5-Enolpyruvylshikimate-3-phosphate Synthase Active Site," *J. Biol. Chem.*, Nov. 25, 1991, pp. 22364-22369, vol. 266, No. 33.

Stalker, D.M., et al., "A Single Amino Acid Substitution in the Enzyme 5-Enolpyruvylshikimate-3-Phosphate Synthase Confers Resistance to the Herbicide Glyphosate," *J. Biol. Chem.*, Apr. 25, 1985, pp. 4724-4728, vol. 260, No. 8.

* cited by examiner

*Primary Examiner* — David H Kruse

(57) ABSTRACT

Compositions and methods for conferring herbicide resistance or tolerance to bacteria, plants, plant cells, tissues and seeds are provided. Compositions include polynucleotides encoding herbicide resistance or tolerance polypeptides, vectors comprising those polynucleotides, and host cells comprising the vectors. The nucleotide sequences of the invention can be used in DNA constructs or expression cassettes for transformation and expression in organisms, including microorganisms and plants. Compositions also include transformed bacteria, plants, plant cells, tissues, and seeds. In particular, isolated polynucleotides encoding glyphosate resistance or tolerance polypeptides are provided. Additionally, amino acid sequences corresponding to the polynucleotides are encompassed.

24 Claims, 3 Drawing Sheets

GRG23 EPSP SYNTHASES: COMPOSITIONS AND METHODS OF USE

CROSS REFERENCE TO RELATED APPLICATION

This application claims the benefit of U.S. patent application Ser. No. 11/943,801, filed Nov. 21, 2007, which claims the benefit of U.S. Provisional Application Ser. Nos. 60/861,455, filed Nov. 29, 2006; 60/872,200, filed Dec. 1, 2006; and 60/972,502, filed Sep. 14, 2007, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "APA049US03D02_SEQLIST.txt", created on Jul. 29, 2010, and having a size of 151,000 bytes and is filed concurrently with the specification. The sequence listing contained in this ASCII formatted document is part of the specification and is herein incorporated by reference in its entirety.

FIELD OF THE INVENTION

This invention relates to plant molecular biology, particularly novel EPSP synthase polypeptides that confer improved resistance or tolerance to the herbicide glyphosate.

BACKGROUND OF THE INVENTION

N-phosphonomethylglycine, commonly referred to as glyphosate, is an important agronomic chemical. Glyphosate inhibits the enzyme that converts phosphoenolpyruvic acid (PEP) and 3-phosphoshikimic acid (S3P) to 5-enolpyruvyl-3-phosphoshikimic acid. Inhibition of this enzyme (5-enolpyruvylshikimate-3-phosphate synthase; referred to herein as "EPSP synthase", or "EPSPS") kills plant cells by shutting down the shikimate pathway, thereby inhibiting aromatic amino acid biosynthesis.

Since glyphosate-class herbicides inhibit aromatic amino acid biosynthesis, they not only kill plant cells, but are also toxic to bacterial cells. Glyphosate inhibits many bacterial EPSP synthases, and thus is toxic to these bacteria. However, certain bacterial EPSP synthases have a high tolerance to glyphosate.

Plant cells resistant to glyphosate toxicity can be produced by transforming plant cells to express glyphosate-resistant bacterial EPSP synthases. Notably, the bacterial gene from *Agrobacterium tumefaciens* strain CP4 has been used to confer herbicide resistance on plant cells following expression in plants. A mutated EPSP synthase from *Salmonella typhimurium* strain CT7 confers glyphosate resistance in bacterial cells, and confers glyphosate resistance on plant cells (U.S. Pat. Nos. 4,535,060; 4,769,061; and 5,094,945).

U.S. Pat. No. 6,040,497 reports mutant maize EPSP synthase enzymes having substitutions of threonine to isoleucine at position 102 and proline to serine at position 106 (the "TIPS" mutation). Such alterations confer glyphosate resistance upon the maize enzyme. A mutated EPSP synthase from *Salmonella typhimurium* strain CT7 confers glyphosate resistance in bacterial cells, and is reported to confer glyphosate resistance upon plant cells (U.S. Pat. Nos. 4,535,060; 4,769,061; and 5,094,945). He et al. ((2001) *Biochim et Biophysica Acta* 1568:1-6) have developed EPSP synthases with increased glyphosate tolerance by mutagenesis and recombination between the *E. coli* and *Salmonella typhimurium* EPSP synthase genes, and suggest that mutations at position 42 (T42M) and position 230 (Q230K) are likely responsible for the observed resistance. Subsequent work (He et al. (2003) *Biosci. Biotech. Biochem.* 67:1405-1409) shows that the T42M mutation (threonine to methionine) is sufficient to improve tolerance of both the *E. coli* and *Salmonella typhimurium* enzymes. Due to the many advantages herbicide resistance plants provide, herbicide resistance genes improved glyphosate resistance activity are desirable.

An alternate method for mutagenesis is the "permutational mutagenesis" method described in U.S. patent application Ser. No. 11/762,580, filed Jun. 13, 2007.

SUMMARY OF INVENTION

Compositions and methods for conferring resistance or tolerance to are provided. Compositions include EPSP synthase enzymes that are resistant to glyphosate herbicide, and nucleic acid molecules encoding such enzymes, vectors comprising those nucleic acid molecules, and host cells comprising the vectors. The compositions include nucleic acid molecules encoding herbicide resistance polypeptides, including those encoding polypeptides comprising SEQ ID NO:9, 11, 13, 15, 17, 19, 21, 23, 25, 27, 29, 31, 33, or 35, as well as the polynucleotide sequences of SEQ ID NO:6, 8, 10, 12, 14, 16, 18, 20, 22, 24, 26, 28, 30, 32, or 34. The coding sequences can be used in DNA constructs or expression cassettes for transformation and expression in organisms, including microorganisms and plants. Compositions also comprise transformed bacteria, plants, plant cells, tissues, and seeds that are glyphosate resistant by the introduction of the compositions of the invention into the genome of the organism. Where the organism is a plant, the introduction of the sequence allows for glyphosate containing herbicides to be applied to plants to selectively kill glyphosate sensitive weeds or other untransformed plants, but not the transformed organism. The sequences can additionally be used a marker for selection of plant cells growing under glyphosate conditions.

Methods for identifying an EPSP synthase enzyme with glyphosate resistance activity are additionally provided. The methods comprise identifying additional EPSP synthase sequences that are resistant to glyphosate based on the presence of the domain of the invention.

DETAILED DESCRIPTION OF THE INVENTION

Figure 1:
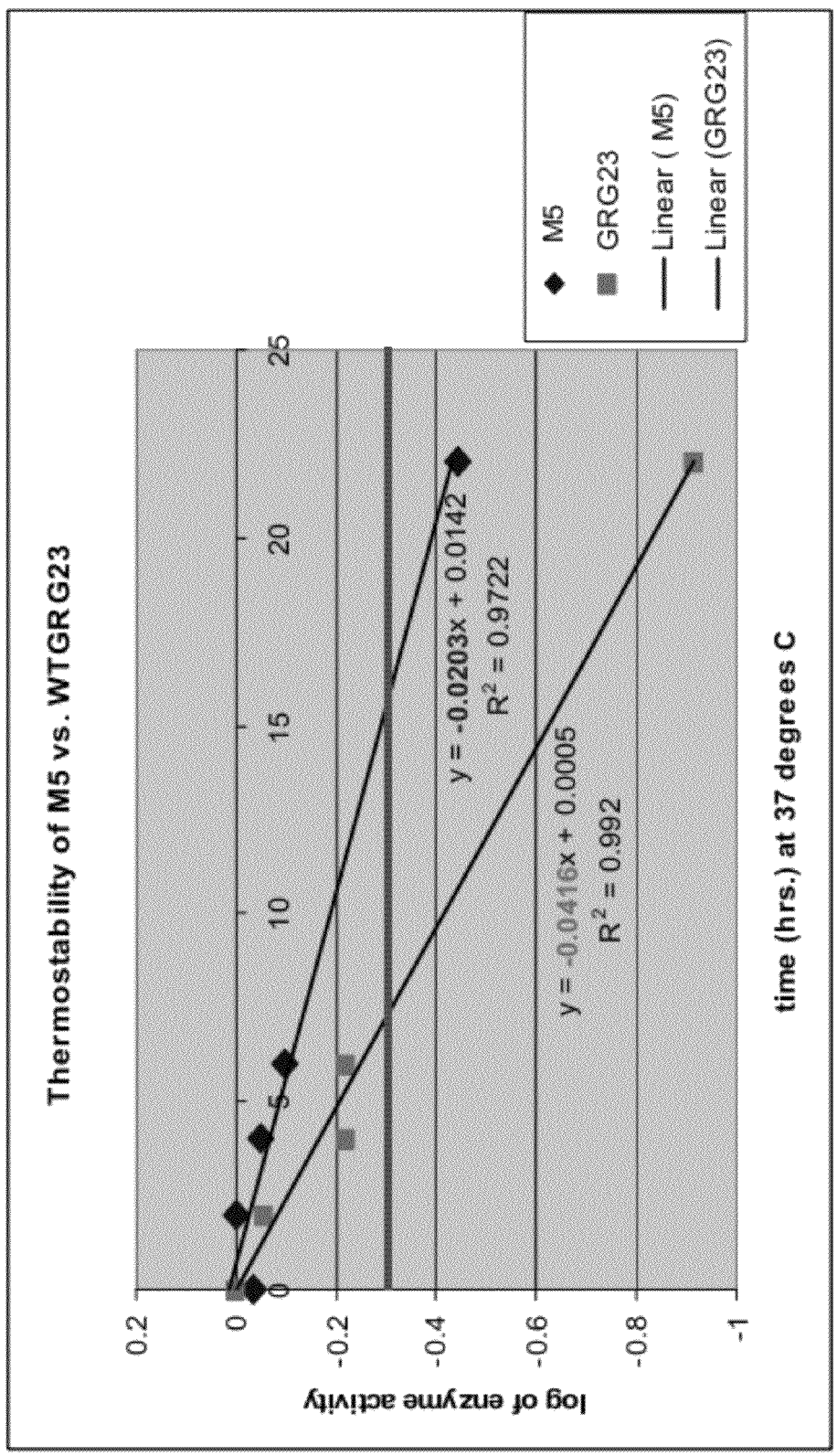
FIG. 1 demonstrates the enzymatic activity of GRG23 (ace1) ("M5"; SEQ ID NO:10) compared to wild type GRG23 ("WTGRG23"; SEQ ID NO:2) at 37° C. for 0 to 25 hours.
Figure 2:
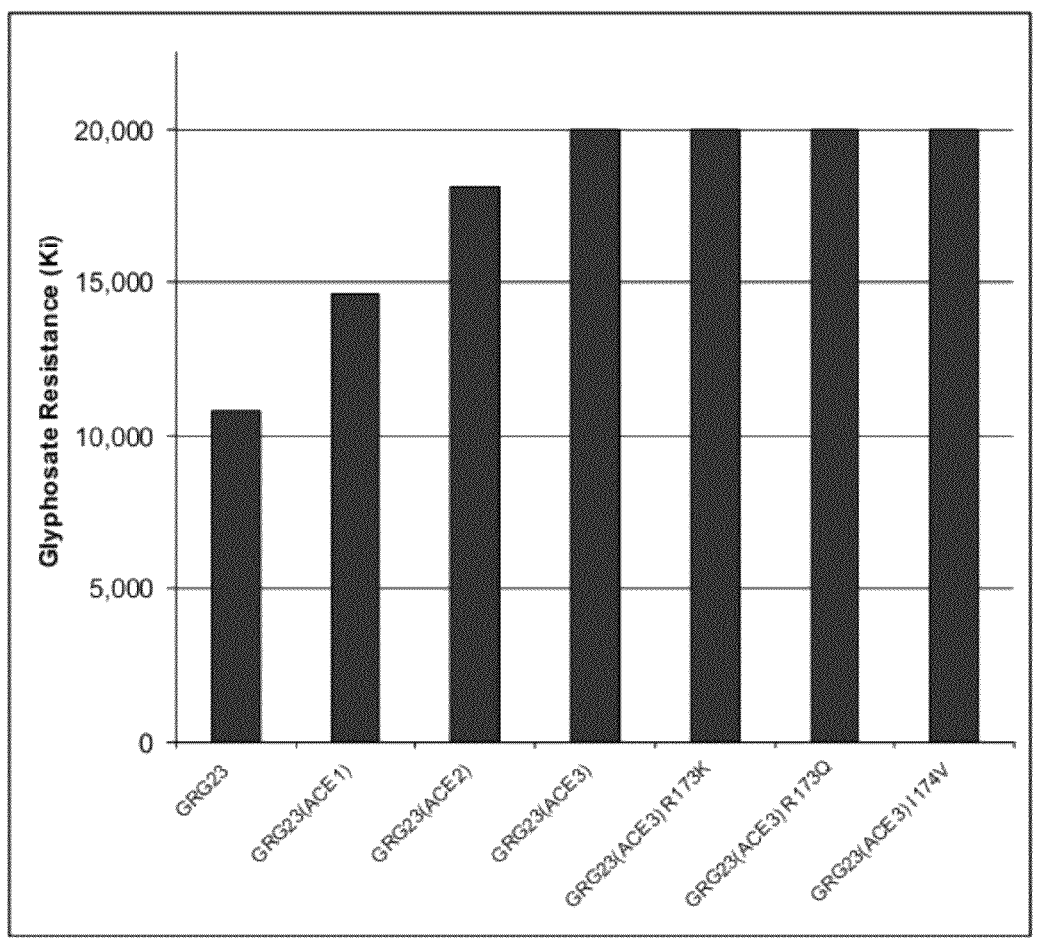
FIG. 2 shows the resistance of GRG23 and several variants to glyphosate, expressed as the inhibition constant, or $K_i$
Figure 3:
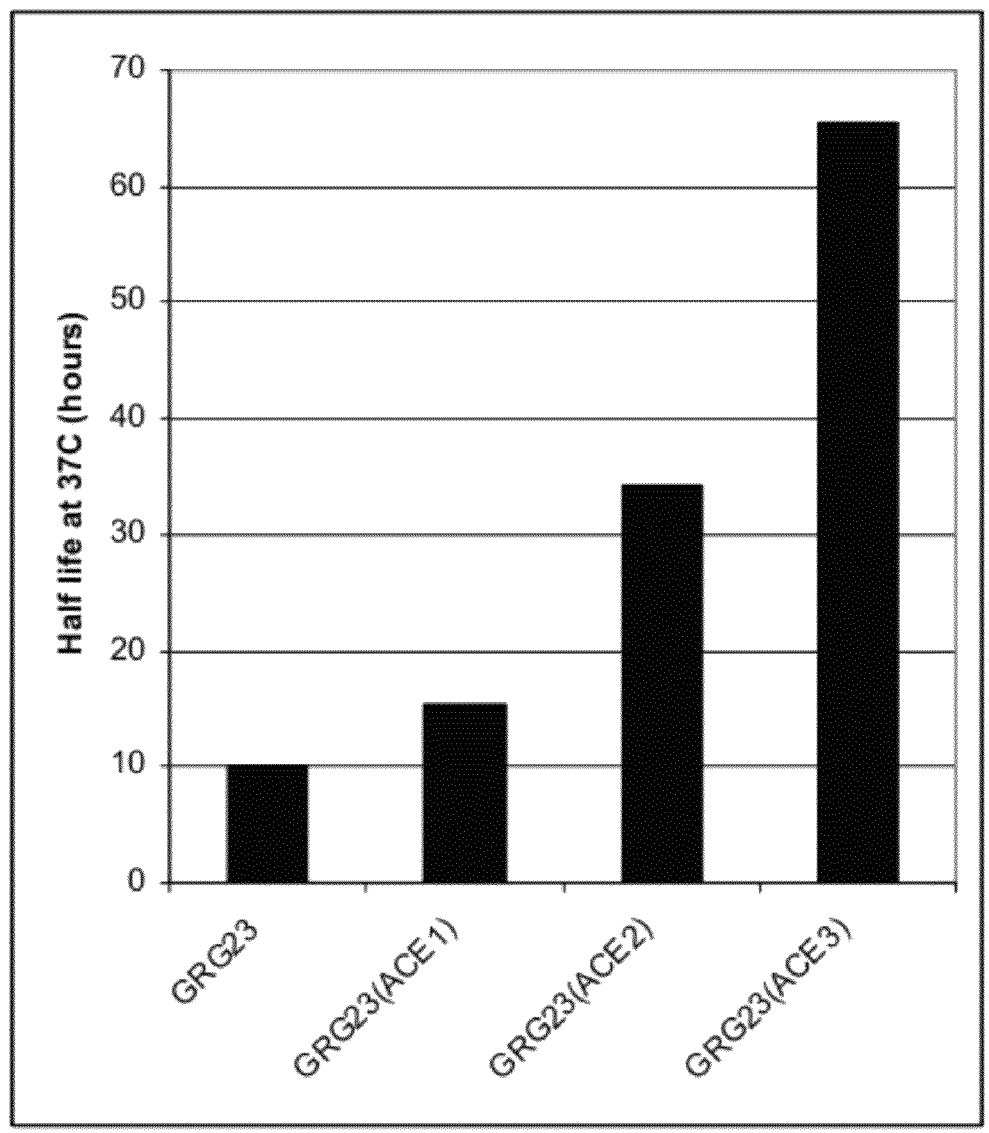
FIG. 3 shows the half life of GRG23 and GRG23 variants at 37'C.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention is drawn to compositions and methods for regulating herbicide resistance in organisms, particularly in plants or plant cells. The methods involve transforming organisms with nucleotide sequences encoding the glyphosate resistance gene of the invention. The nucleotide sequences of the invention are useful for preparing plants that show increased tolerance to the herbicide glyphosate. Thus, by "glyphosate resistance" or "glyphosate tolerance" gene of the invention is intended the nucleotide sequence set forth in SEQ ID NO:6, 8, 10, 12, 14, 16, 18, 20, 22, 24, 26, 28, 30, 32, or 34, and fragments and variants thereof that encode a glyphosate resistance or tolerance polypeptide. Likewise, a "glyphosate resistance" or "glyphosate tolerance" polypeptide of the invention is a polypeptide having the amino acid sequence set forth in SEQ ID NO:9, 11, 13, 15, 17, 19, 21, 23, 25, 27, 29, 31, 33, or 35, and fragments and variants thereof, that confer glyphosate resistance or tolerance to a host cell.

A. Isolated Polynucleotides, and Variants and Fragments Thereof.

In some embodiments, the present invention comprises isolated, recombinant, or purified polynucleotides. An "isolated" or "purified" polynucleotide or polypeptide, or biologically active portion thereof, is substantially free of other cellular material, or culture medium when produced by recombinant techniques, or substantially free of chemical precursors or other chemicals when chemically synthesized. By "biologically active" is intended to possess the desired biological activity of the native polypeptide, that is, retain herbicide resistance activity. An "isolated" polynucleotide may be free of sequences (for example, protein encoding sequences) that naturally flank the nucleic acid (i.e., sequences located at the 5' and 3' ends of the nucleic acid) in the genomic DNA of the organism from which the polynucleotide is derived. For purposes of the invention, "isolated" when used to refer to polynucleotides excludes isolated chromosomes. For example, in various embodiments, the isolated glyphosate resistance-encoding polynucleotide can contain less than about 5 kb, 4 kb, 3 kb, 2 kb, 1 kb, 0.5 kb, or 0.1 kb of nucleotide sequence that naturally flanks the polynucleotide in genomic DNA of the cell from which the polynucleotide is derived.

Polynucleotides of the invention include those that encode glyphosate-resistant polypeptides comprising SEQ ID NO:9, 11, 13, 15, 17, 19, 21, 23, 25, 27, 29, 31, 33, or 35, as well as the polynucleotide sequences of SEQ ID NO:6, 8, 10, 12, 14, 16, 18, 20, 22, 24, 26, 28, 30, 32, or 34.

By "glyphosate" is intended any herbicidal form of N-phosphonomethylglycine (including any salt thereof) and other forms that result in the production of the glyphosate anion in planta. An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer time than cells that do not express the protein. A "glyphosate resistance protein" includes a protein that confers upon a cell the ability to tolerate a higher concentration of glyphosate than cells that do not express the protein, or to tolerate a certain concentration of glyphosate for a longer period of time than cells that do not express the protein. By "tolerate" or "tolerance" is intended either to survive, or to carry out essential cellular functions such as protein synthesis and respiration in a manner that is not readily discernable from untreated cells.

The present invention further contemplates variants and fragments of the polynucleotides described herein. A "fragment" of a polynucleotide may encode a biologically active portion of a polypeptide, or it may be a fragment that can be used as a hybridization probe or PCR primer using methods disclosed elsewhere herein. Polynucleotides that are fragments of a polynucleotide comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 contiguous nucleotides, or up to the number of nucleotides present in a full-length polynucleotide disclosed herein depending upon the intended use (e.g., an EPSP synthase polynucleotide comprising SEQ ID NO:1). By "contiguous" nucleotides is intended nucleotide residues that are immediately adjacent to one another.

Fragments of the polynucleotides of the present invention generally will encode polypeptide fragments that retain the biological activity of the full-length glyphosate resistance protein; i.e., herbicide-resistance activity. By "retains herbicide resistance activity" is intended that the fragment will have at least about 30%, at least about 50%, at least about 70%, at least about 80%, 85%, 90%, 95%, 100%, 110%, 125%, 150%, 175%, 200%, 250%, at least about 300% or greater of the herbicide resistance activity of the full-length glyphosate resistance protein disclosed herein as SEQ ID NO:2, 3, or 5. Methods for measuring herbicide resistance activity are well known in the art. See, for example, U.S. Pat. Nos. 4,535,060, and 5,188,642, each of which are herein incorporated by reference in their entirety.

A fragment of a polynucleotide that encodes a biologically active portion of a polypeptide of the invention will encode at least about 15, 25, 30, 50, 75, 100, 125, 150, 175, 200, 250, 300, 350, 400 contiguous amino acids, or up to the total number of amino acids present in a full-length polypeptide of the invention.

The invention also encompasses variant polynucleotides. "Variants" of the polynucleotide include those sequences that encode the polypeptides disclosed herein but that differ conservatively because of the degeneracy of the genetic code, as well as those that are sufficiently identical.

The term "sufficiently identical" is intended a polypeptide or polynucleotide sequence that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity compared to a reference sequence using one of the alignment programs using standard parameters. One of skill in the art will recognize that these values can be appropriately adjusted to determine corresponding identity of polypeptides encoded by two polynucleotides by taking into account codon degeneracy, amino acid similarity, reading frame positioning, and the like.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may lead to generation of variants that confer herbicide resistance. These herbicide resistance proteins are encompassed in the present invention and may be used in the methods of the present invention.

Naturally occurring allelic variants can be identified with the use of well-known molecular biology techniques, such as polymerase chain reaction (PCR) and hybridization techniques as outlined below. Variant polynucleotides also include synthetically derived polynucleotides that have been generated, for example, by using site-directed or other mutagenesis strategies but which still encode the polypeptide having the desired biological activity.

The skilled artisan will further appreciate that changes can be introduced by further mutation of the polynucleotides of the invention thereby leading to further changes in the amino acid sequence of the encoded polypeptides, without altering the biological activity of the polypeptides. Thus, variant isolated polynucleotides can be created by introducing one or more additional nucleotide substitutions, additions, or deletions into the corresponding polynucleotide encoding the EPSP synthase domain disclosed herein, such that one or more amino acid substitutions, additions or deletions are introduced into the encoded polypeptide. Further mutations can be introduced by standard techniques, such as site-directed mutagenesis and PCR-mediated mutagenesis, or gene shuffling techniques. Such variant polynucleotides are also encompassed by the present invention.

Variant polynucleotides can be made by introducing mutations randomly along all or part of the coding sequence, such as by saturation mutagenesis, and the resultant mutants can be screened for the ability to confer herbicide resistance activity to identify mutants that retain activity.

Gene shuffling or sexual PCR procedures (for example, Smith (1994) *Nature* 370:324-325; U.S. Pat. Nos. 5,837,458; 5,830,721; 5,811,238; and 5,733,731, each of which is herein incorporated by reference) can be used to further modify or enhance polynucleotides and polypeptides having the EPSP synthase domain of the present invention (for example, polypeptides that confer glyphosate resistance). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in different clones becoming mixed and accumulating in some of the resulting sequences. Multiple cycles of selection and shuffling have led to the functional enhancement of several enzymes (Stemmer (1994) *Nature* 370:389-391; Stemmer (1994) *Proc. Natl. Acad. Sci. USA* 91:10747-10751; Crameri et al. (1996) *Nat. Biotechnol.* 14:315-319; Zhang et al. (1997) *Proc. Natl. Acad. Sci. USA* 94:4504-4509; and Crameri et al. (1997) *Nat. Biotechnol.* 15:436-438). Such procedures could be performed, for example, on polynucleotides encoding polypeptides having the sequence domain of the present invention to generate polypeptides that confer glyphosate resistance.

Using methods such as PCR, hybridization, and the like corresponding herbicide resistance sequences can be identified by looking for EPSP synthase domains of the present invention. See, for example, Sambrook and Russell (2001) *Molecular Cloning: A Laboratory Manual* (Cold Spring Harbor Laboratory Press, Cold Spring Harbor, N.Y.) and Innis et al. (1990) *PCR Protocols: A Guide to Methods and Applications* (Academic Press, NY).

B. Isolated Proteins and Variants and Fragments Thereof

Herbicide resistance polypeptides are also encompassed within the present invention. An herbicide resistance polypeptide that is substantially free of cellular material includes preparations of polypeptides having less than about 30%, 20%, 10%, or 5% (by dry weight) of non-herbicide resistance polypeptide (also referred to herein as a "contaminating protein"). In the present invention, "herbicide resistance protein" is intended an EPSP synthase polypeptide having the sequence domain of the invention. Fragments, biologically active portions, and variants thereof are also provided, and may be used to practice the methods of the present invention.

"Fragments" or "biologically active portions" include polypeptide fragments comprising a portion of an amino acid sequence encoding an herbicide resistance protein and that retains herbicide resistance activity. A biologically active portion of an herbicide resistance protein can be a polypeptide that is, for example, 10, 25, 50, 100 or more amino acids in length. Such biologically active portions can be prepared by recombinant techniques and evaluated for herbicide resistance activity.

By "variants" is intended proteins or polypeptides having an amino acid sequence that is at least about 60%, 65%, about 70%, 75%, about 80%, 85%, 90%, 91%, 92%, 93%, 94%, 95%, 96%, 97%, 98% or 99% identical to an EPSP synthase polypeptide having the EPSP synthase domain of the present invention. One of skill in the art will recognize that these values can be appropriately adjusted to determine corresponding identity of polypeptides encoded by two polynucleotides by taking into account codon degeneracy, amino acid similarity, reading frame positioning, and the like.

For example, conservative amino acid substitutions may be made at one or more nonessential amino acid residues. A "nonessential" amino acid residue is a residue that can be altered from the wild-type sequence of a polypeptide without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for polypeptide activity. However, one of skill in the art would understand that functional variants may have minor conserved or non-conserved alterations in the conserved residues.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

C. Polynucleotide Constructs

The polynucleotides encoding the EPSP synthase polypeptides of the present invention may be modified to obtain or enhance expression in plant cells. The polynucleotides encoding the polypeptides identified herein may be provided in expression cassettes for expression in the plant of interest. A "plant expression cassette" includes a DNA construct, including a recombinant DNA construct, that is capable of resulting in the expression of a polynucleotide in a plant cell. The cassette can include in the 5'-3' direction of transcription, a transcriptional initiation region (i.e., promoter, particularly a heterologous promoter) operably-linked to one or more polynucleotides of interest, and/or a translation and transcriptional termination region (i.e., termination region) functional in plants. The cassette may additionally contain at least one additional polynucleotide to be introduced into the organism, such as a selectable marker gene. Alternatively, the additional polynucleotide(s) can be provided on multiple expression cassettes. Such an expression cassette is provided with a plurality of restriction sites for insertion of the polynucleotide(s) to be under the transcriptional regulation of the regulatory regions.

"Heterologous" generally refers to the polynucleotide or polypeptide that is not endogenous to the cell or is not endogenous to the location in the native genome in which it is present, and has been added to the cell by infection, transfection, microinjection, electroporation, microprojection, or the like. By "operably linked" is intended a functional linkage between two polynucleotides. For example, when a promoter is operably linked to a DNA sequence, the promoter sequence initiates and mediates transcription of the DNA sequence. It is recognized that operably linked polynucleotides may or may not be contiguous and, where used to reference the joining of two polypeptide coding regions, the polypeptides are expressed in the same reading frame.

The promoter may be any polynucleotide sequence which shows transcriptional activity in the chosen plant cells, plant parts, or plants. The promoter may be native or analogous, or foreign or heterologous, to the plant host and/or to the DNA sequence of the invention. Where the promoter is "native" or "analogous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds (1987) *Nucleic Acids Res.* 15:2343-2361. Also, the location of the promoter relative to the transcription start may be optimized. See, e.g., Roberts et al. (1979) *Proc. Natl. Acad. Sci. USA*, 76:760-764. Many suitable promoters for use in plants are well known in the art.

For instance, suitable constitutive promoters for use in plants include: the promoters from plant viruses, such as the peanut chlorotic streak caulimovirus (PClSV) promoter (U.S. Pat. No. 5,850,019); the 35S promoter from cauliflower mosaic virus (CaMV) (Odell et al. (1985) *Nature* 313:810-812); promoters of Chlorella virus methyltransferase genes (U.S. Pat. No. 5,563,328) and the full-length transcript promoter from figwort mosaic virus (FMV) (U.S. Pat. No. 5,378,619); the promoters from such genes as rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); maize H3 histone (Lepetit et al. (1992) *Mol. Gen. Genet.* 231:276-285 and Atanassova et al. (1992) *Plant J.* 2(3):291-300); *Brassica napus* ALS3 (PCT application WO 97/41228); and promoters of various *Agrobacterium* genes (see U.S. Pat. Nos. 4,771,002; 5,102,796; 5,182,200; and 5,428,147).

Suitable inducible promoters for use in plants include: the promoter from the ACE1 system which responds to copper (Mett et al. (1993) *PNAS* 90:4567-4571); the promoter of the maize In2 gene which responds to benzenesulfonamide herbicide safeners (Hershey et al. (1991) *Mol. Gen. Genetics* 227:229-237 and Gatz et al. (1994) *Mol. Gen. Genetics* 243: 32-38); and the promoter of the Tet repressor from Tn10 (Gatz et al. (1991) *Mol. Gen. Genet.* 227:229-237). Another inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone (Schena et al. (1991) *Proc. Natl. Acad. Sci. USA* 88:10421) or the recent application of a chimeric transcription activator, XVE, for use in an estrogen receptor-based inducible plant expression system activated by estradiol (Zuo et al. (2000) *Plant J.,* 24:265-273). Other inducible promoters for use in plants are described in EP 332104, PCT WO 93/21334 and PCT WO 97/06269 which are herein incorporated by reference in their entirety. Promoters composed of portions of other promoters and partially or totally synthetic promoters can also be used. See, e.g., Ni et al. (1995) *Plant J.* 7:661-676 and PCT WO 95/14098 describing such promoters for use in plants.

The promoter may include, or be modified to include, one or more enhancer elements. In some embodiments, the promoter may include a plurality of enhancer elements. Promoters containing enhancer elements provide for higher levels of transcription as compared to promoters that do not include them. Suitable enhancer elements for use in plants include the PClSV enhancer element (U.S. Pat. No. 5,850,019), the CaMV 35S enhancer element (U.S. Pat. Nos. 5,106,739 and 5,164,316) and the FMV enhancer element (Maiti et al. (1997) *Transgenic Res.* 6:143-156). See also PCT WO 96/23898.

Often, such constructs can contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the construct can be engineered to contain a signal peptide to facilitate transfer of the peptide to the endoplasmic reticulum. By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that, when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a polynucleotide located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a polynucleotide located upstream of a coding sequence.

Other upstream or downstream untranslated elements include enhancers. Enhancers are polynucleotides that act to increase the expression of a promoter region. Enhancers are well known in the art and include, but are not limited to, the SV40 enhancer region and the 35S enhancer element.

The termination region may be native with the transcriptional initiation region, may be native with the sequence of the present invention, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

In one aspect of the invention, synthetic DNA sequences are designed for a given polypeptide, such as the polypeptides of the invention. Expression of the open reading frame of the synthetic DNA sequence in a cell results in production of the polypeptide of the invention. Synthetic DNA sequences can be useful to simply remove unwanted restriction endonuclease sites, to facilitate DNA cloning strategies, to alter or remove any potential codon bias, to alter or improve GC content, to remove or alter alternate reading frames, and/or to alter or remove intron/exon splice recognition sites, polyadenylation sites, Shine-Delgarno sequences, unwanted promoter elements and the like that may be present in a native DNA sequence. It is also possible that synthetic DNA sequences may be utilized to introduce other improvements to a DNA sequence, such as introduction of an intron sequence, creation of a DNA sequence that in expressed as a protein fusion to organelle targeting sequences, such as chloroplast transit peptides, apoplast/vacuolar targeting peptides, or peptide sequences that result in retention of the resulting peptide in the endoplasmic reticulum. Synthetic genes can also be synthesized using host cell-preferred codons for improved expression, or may be synthesized using codons at a host-preferred codon usage frequency. See, for example, Campbell and Gowri (1990) *Plant Physiol.* 92:1-11; U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the polynucleotides of interest are targeted to the chloroplast for expression. In this manner, where the polynucleotide of interest is not directly inserted into the chloroplast, the expression cassette will additionally contain a polynucleotide encoding a transit peptide to direct the nucleotide of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The polynucleotides of interest to be targeted to the chloroplast may be optimized for expression in the chloroplast to account for differences in codon usage between the plant nucleus and this organelle. In this manner, the polynucleotides of interest may be synthesized using chloroplast-preferred codons. See, for example, U.S. Pat. No. 5,380,831, herein incorporated by reference.

This plant expression cassette can be inserted into a plant transformation vector. By "transformation vector" is intended a DNA molecule that allows for the transformation of a cell. Such a molecule may consist of one or more expression cassettes, and may be organized into more than one vector DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a polynucleotide construct designed for transfer between different host cells. "Expression vector" refers to a vector that has the ability to incorporate, integrate and express heterologous DNA sequences or fragments in a foreign cell.

The plant transformation vector comprises one or more DNA vectors for achieving plant transformation. For example, it is a common practice in the art to utilize plant transformation vectors that comprise more than one contiguous DNA segment. These vectors are often referred to in the art as binary vectors. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "polynucleotide of interest" (a polynucleotide engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker sequence and the sequence of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science,* 5:446-451). Several types of *Agrobacterium* strains (e.g., LBA4404, GV3101, EHA101, EHA105, etc.) can be used for plant transformation. The second plasmid vector is not necessary for introduction of polynucleotides into plants by other methods such as microprojection, microinjection, electroporation, polyethylene glycol, etc.

D. Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene and in this case "glyphosate") to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (e.g. "glyphosate"). The shoots are then transferred to a selective rooting medium for recovering rooted shoot or plantlet. The transgenic plantlet then grow into mature plants and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can be used to confirm the presence of the integrated heterologous gene of interest in the genome of transgenic plant.

Generation of transgenic plants may be performed by one of several methods, including, but not limited to, introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

E. Evaluation of Plant Transformation

Following introduction of heterologous foreign DNA into plant cells, the transformation or integration of the heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual* (Cold Spring Harbor Laboratory Press, Cold Spring Harbor, N.Y.)). PCR is carried out using oligonucleotide primers specific to the gene of interest or *Agrobacterium* vector background, etc.

Plant transformation may be confirmed by Southern blot analysis of genomic DNA (Sambrook and Russell (2001) supra). In general, total DNA is extracted from the transformant, digested with appropriate restriction enzymes, fractionated in an agarose gel and transferred to a nitrocellulose or nylon membrane. The membrane or "blot" can then be probed with, for example, radiolabeled $^{32}$P target DNA fragment to confirm the integration of the introduced gene in the plant genome according to standard techniques (Sambrook and Russell, 2001, supra).

In Northern analysis, RNA is isolated from specific tissues of transformant, fractionated in a formaldehyde agarose gel, and blotted onto a nylon filter according to standard procedures that are routinely used in the art (Sambrook and Russell (2001) supra). Expression of RNA encoded by grg sequences of the invention is then tested by hybridizing the filter to a radioactive probe derived from a GDC by methods known in the art (Sambrook and Russell (2001) supra)

Western blot and biochemical assays and the like may be carried out on the transgenic plants to determine the presence of protein encoded by the herbicide resistance gene by standard procedures (Sambrook and Russell (2001) supra) using antibodies that bind to one or more epitopes present on the herbicide resistance protein.

In one aspect of the invention, the grg genes described herein are useful as markers to assess transformation of bacterial or plant cells.

F. Plants and Plant Parts

By "plant" is intended whole plants, plant organs (e.g., leaves, stems, roots, etc.), seeds, plant cells, propagules, embryos and progeny of the same. Plant cells can be differentiated or undifferentiated (e.g., callus, suspension culture cells, protoplasts, leaf cells, root cells, phloem cells, pollen). The present invention may be used for introduction of polynucleotides into any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Crop plants are also of interest, including, for example, maize, sorghum, wheat, sunflower, tomato, crucifers, peppers, potato, cotton, rice, soybean, sugarbeet, sugarcane, tobacco, barley, oilseed rape, etc.

This invention is suitable for any member of the monocot plant family including, but not limited to, maize, rice, barley, oats, wheat, sorghum, rye, sugarcane, pineapple, yams, onion, banana, coconut, and dates.

G. Methods for Increasing Plant Yield

Methods for increasing plant yield are provided. The methods comprise introducing into a plant or plant cell a polynucleotide comprising a grg sequence disclosed herein. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase.

In specific methods, the plant is treated with an effective concentration of an herbicide, where the herbicide application results in enhanced plant yield. By "effective concentration" is intended the concentration which allows the increased yield in the plant. Such effective concentrations for herbicides of interest are generally known in the art. The herbicide may be applied either pre- or post emergence in accordance with usual techniques for herbicide application to fields comprising crops which have been rendered resistant to the herbicide by heterologous expression of a grg gene of the invention.

Methods for conferring herbicide resistance in a plant or plant part are also provided. In such methods, a grg polynucleotide disclosed herein is introduced into the plant, wherein expression of the polynucleotide results in glyphosate tolerance or resistance. Plants produced via this method can be treated with an effective concentration of an herbicide and display an increased tolerance to the herbicide. An "effective concentration" of an herbicide in this application is an amount sufficient to slow or stop the growth of plants or plant parts that are not naturally resistant or rendered resistant to the herbicide.

H. Methods of Controlling Weeds in a Field

Methods for selectively controlling weeds in a field containing a plant are also provided. In one embodiment, the plant seeds or plants are glyphosate resistant as a result of a grg polynucleotide disclosed herein being inserted into the plant seed or plant. In specific methods, the plant is treated with an effective concentration of an herbicide, where the herbicide application results in a selective control of weeds or other untransformed plants. By "effective concentration" is intended the concentration which controls the growth or spread of weeds or other untransformed plants without significantly affecting the glyphosate-resistant plant or plant seed. Such effective concentrations for herbicides of interest are generally known in the art. The herbicide may be applied either pre- or post emergence in accordance with usual techniques for herbicide application to fields comprising plants or plant seeds which have been rendered resistant to the herbicide.

I. Temperature Spectrum

Several studies of glyphosate metabolism in plants have been carried out, and reveal that glyphosate is not metabolized by plants or is metabolized very slowly. Glyphosate penetrates the cuticle rapidly, and is translocated throughout plants over a considerable period of time (reviewed in Kearney and Kaufman, Eds (1988) *Herbicides; Chemistry, Degradation & Mode of Action* Marcel Dekker, Inc., New York, 3:1-70 and Grossbard and Atkinson, Eds. (1985) *The Herbicide Glyphosate* Butterworths, London, p. 25-34). Thus, it is likely that glyphosate tolerance is necessary over a sustained period of time following glyphosate exposure in agronomically-important plants. Where temperatures frequently exceed 30° C. during the growing season, it would be advantageous to employ a glyphosate-tolerance EPSP synthase that maintains activity at elevated temperatures.

In one embodiment of the present invention, the EPSP synthase exhibits thermal stability at a temperature that is higher or lower than ambient environmental temperature. By "thermal stability" is intended that the enzyme is active at a higher or lower temperature than ambient environmental temperature for a longer period of time than an EPSP synthase that is not thermal stable at that temperature. For example, a thermal stable EPSP synthase has enzymatic activity for greater than about 1 hour, greater than about 2 hours, about 3, about 4, about 5, about 6, about 7, about 8, about 9, about 10, about 11, about 12, about 13, about 14, about 15, about 20, about 25 hours, or longer, at a temperature that is higher or lower than ambient environmental temperature. For the purposes of the present invention, "ambient" environmental temperature is about 30° C. In some embodiments, a higher than ambient temperature is a temperature at or above about 32° C., about 34° C., about 37° C., about 40° C., about 45° C., about 50° C., about 55° C., about 60° C., about 65° C., or higher. A lower than ambient temperature is a temperature at or below about 28° C., below about 27° C., about 26° C., about 25° C., about 23° C., about 20° C., about 18° C., about 15° C., about 10° C., at or below about 5° C., or around 0° C. Methods to assay for EPSP synthase activity are discussed in further details elsewhere herein. For the purposes of the present invention, a thermal stable EPSP synthase is considered active when it functions at about 90% to 100%, about 80% to about 90%, about 70% to about 80%, about 60% to about 70% or about 50% to about 60% of the maximum activity level observed at the optimum temperature for that enzyme.

Thus, provided herein are methods and compositions for increasing glyphosate tolerance at temperatures higher than ambient environmental temperatures. In one embodiment, the methods comprise introducing into a plant a nucleotide sequence encoding the glyphosate tolerance EPSP synthase enzyme set forth in SEQ ID NO:8, 10, 14, 28, 30, 32, or 34, and growing the plant at a temperature that is higher than ambient environmental temperature. In specific embodiments, the growing temperature is higher than ambient temperature for an average of at least about 2 hours per day, at least about 3 hours per day, at least about 4 hours per day, at least about 5, about 6, about 7, about 8, about 9, about 10, about 11, about 12, about 14, about 16, about 18, about 20, at least about 22 hours per day, or up to about 24 hours a day during the growing season of the plant.

In another embodiment, the method comprises introducing into a plant a nucleotide sequence encoding the glyphosate tolerant EPSP synthase enzyme set forth in SEQ ID NO:8, 10, 14, 28, 30, 32, or 34, contacting the plant with an herbicidally-effective concentration of glyphosate, and growing the plant at a temperature that exceeds ambient environmental temperature for at least 1 hour, at least about 2 hours, at least about 3, at least about 4, or more hours per day for at least 2, 3, 4, 5, 6, 7, 8, 9, 10, 11, 12, 13, 14, 15, 16, 17, 18, 19, 20 or more days after glyphosate is applied to the plant, wherein the days in which the temperature exceeds ambient environmental temperature occur during the growing season of the plant.

The following examples are offered by way of illustration and not by way of limitation.

EXPERIMENTAL

Example 1 syngrg23 Design and Expression

GRG23 (SEQ ID NO:2) is an EPSP synthase that possesses excellent kinetic values for Km, Ki and Vmax (U.S. Pat. No. 7,674,958). A novel gene sequence encoding the GRG23 protein (U.S. Pat. No. 7,674,958) was designed and synthesized. The resulting sequence is provided herein as SEQ ID NO:6, and is herein designated "syngrg23." The open reading frame was cloned into the expression vector pRSF1b (Invitrogen) by methods known in the art.

The syngrg23 gene encoding GRG23 was cloned into a pUC19 vector to create pAX748. PCR primers that flanked syngrg23 in this vector were used to amplify syngrg23 from pAX748 using the Mutazyme II system (Stratagene) to introduce random mutations into the syngrg23 coding region. The template was diluted 1:50 in the error-prone PCR reaction, and amplification was carried out for 30 cycles. The resulting PCR product was digested with the restriction enzymes BamH I and Sgs I, gel-purified, and ligated into the vector pRSF1b to create a mutagenized syngrg23 library.

The mutagenized syngrg23 libraries were transformed into E. coli strain BL21*DE3 star (Invitrogen). Following transformation, individual colonies were plated on 1×M63 medium containing 150 mM glyphosate to select for clones that had retained enzymatic activity and growth tolerance.

Example 2

Screening for Glyphosate Resistance on Plates

Library ligations were transformed into BL21*DE3 competent E. coli cells (Invitrogen). The transformations were performed according to the manufacturer's instructions with the following modifications. After incubation for 1 hour at 37° C. in SOC medium, the cells were sedimented by centrifugation (5 minutes, 1000×g, 4° C.). The cells were washed with 1 ml M63+, centrifuged again, and the supernatant decanted. The cells were washed a second time with 1 ml M63+ and resuspended in 200 ul M63+.

For selection of mutant GRG23 enzymes conferring glyphosate resistance in E. coli, the cells were plated onto M63+ agar medium plates containing 150 mM glyphosate, 0.05 mM IPTG (isopropyl-beta-D-thiogalactopyranoside), and 50 μg/ml kanamycin. M63+ medium contains 100 mM $KH_2PO_4$, 15 mM $(NH_4)_2SO_4$, 50 μM $CaCl_2$, 1 μM $FeSO_4$, 50 μM $MgCl_2$, 55 mM glucose, 25 mg/liter L-proline, 10 mg/liter thiamine HCl, sufficient NaOH to adjust the pH to 7.0, and 15 g/liter agar. The plates were incubated for 36 hours at 37° C.

Individual colonies were picked and arrayed into 384-well plates. Two 384-well plates were created in this manner. A third plate of 384 clones was picked from colonies that grown on plates lacking glyphosate.

Example 3

Isolation and Analysis of Glyphosate Resistant GRG23 Variants

BL21*DE3 cells transformed with mutagenized syngrg23 and/or grg23 variants were identified by growth on glyphosate plates. Extracts of mutagenized syngrg23 and grgr23 variants were prepared and assayed for improved enzymatic activity. Colonies identified on glyphosate plates were pinned into 96-well blocks containing LB medium and were grown to an O.D. of about 0.6. IPTG was then added (0.5 mM) and the blocks were incubated overnight at 20° C. to induce protein expression. Protein extracts were prepared from the cell pellets using POP culture reagent (Novagen) and Lysonase (Novagen), and the enzymatic activity in the crude lysates was measured after heating the extracts for 30 min at 37° C. Extracts with activity greater than two standard deviations above the mean of a set of extracts containing the appropriate control protein (for example GRG23) were selected for further analysis.

Clones showing increased activity after incubation as crude extracts were grown in 250 mL LB cultures, and protein expression induced with IPTG. Following induction, the mutant GRG23 protein was purified from each culture by affinity chromatography using a cobalt resin (Novagen). The purified proteins were then tested for enzymatic activity following heating for 0, 2, 4, and approximately 16 hours at 37° C.

Example 4

Improved GRG23 Variants

From a DNA library of mutagenized syngrg23, several clones with improved activity at 37° C. were identified. The DNA sequences of the clones corresponding to these extracts was determined. Table 1 shows the amino acid changes identified in six variants of GRG23 that retained glyphosate resistance: grg23(L3P1.B20) (SEQ ID NO:20) encoding the amino acid sequence GRG23(L3P1.B20) (SEQ ID NO:21), grg23(L3P1.B3) (SEQ ID NO:22) encoding the amino acid sequence grg23(L3P1B3) (SEQ ID NO:23); GRG23 (L3P1.F18) (SEQ ID NO:24) encoding the amino acid sequence GRG23(L3P1.F18) (SEQ ID NO:25); and, grg23 (L3P1.O23) (SEQ ID NO:26) encoding the amino acid sequence GRG23(L3P1.O23) (SEQ ID NO:27).

TABLE 1

Mutations identified in glyphosate-resistant GRG23 variants

| Clone | Amino Acid (AA) in GRG23 |
|---|---|
| L3P1B20 | V206→I |
| L3P1B3 | D75→H, E217→K |
| L3P1F18 | T274→I |
| L3P1O23 | R5→H |

The clones were grown in 250 mL LB cultures, and protein expression induced isolated as described above. The purified proteins were then tested for enzymatic activity following heating for 0, 2, 4, and approximately 16 hours at 37° C. One of the clones, termed "M5", was found to retain an increased proportion of its enzymatic activity after prolonged incubation at 37° C. (Table 2). The DNA sequence of this clones was determined, and the gene is designated herein as grg23(ace1) (SEQ ID NO:8). The protein expressed from grg23(ace1) is designated GRG23(ACE1) (SEQ ID NO:9).

TABLE 2

Half-life of GRG23(ACE1) vs GRG23 at elevated temperature

| Protein | Half-life at 37° C. (hours) |
|---|---|
| GRG23 | 7 |
| GRG23(ACE1) | 15.5 |

GRG23(ACE1) contains 2 amino acid substitutions relative to wild-type GRG23 protein: A49→T and S276→T. The pRSF1b vector that contains this gene is designated pAX3801. FIG. 1 shows the relative stability of GRG23 (ACE1) vs GRG23 at elevated temperatures.

Example 5

Determination of EPSPS Activity of GRG-23 Variants

Extracts containing GRG23 variant proteins were assayed for EPSP synthase activity as described in U.S. Pat. No. 7,674,958, herein incorporated by reference in its entirety. Assays were carried out in a final volume of 50 ul containing 0.5 mM shikimate-3-phosphate, 200 uM phosphoenolpyruvate (PEP), 1 U/ml xanthine oxidase, 2 U/ml nucleoside phosphorylase, 2.25 mM inosine, 1 U/ml horseradish peroxidase, 2 mM glyphosate, 50 mM HEPES/KOH pH 7.0, 100 mM KCl, and AMPLEX® Red (Invitrogen) according to the manufacturer's instructions. Extracts were incubated with all assay components except shikimate-3-phosphate for 5 minutes at room temperature, and assays were started by adding shikimate-3-phosphate. EPSP synthase activity was measured using a Spectramax Gemini XPS fluorescence spectrometer (Molecular Dynamics, excitation: 555 nm; emission: 590 nm).

A full determination of kinetic parameters was performed on purified protein as previously described (U.S. Pat. No. 7,674,958), adjusting for the quantity of protein determined by Bradford assay as known in the art. For any one glyphosate concentration, EPSP synthase activity was measured as a function of a broad range of PEP concentrations. The data were fit to the Michaelis-Menten equation using KALEIDAGRAPH® software (Synergy Software) and used to determine the $K_m$ ($K_m$ apparent) of the EPSP synthase at that glyphosate concentration. $K_m$ apparent values were determined at no fewer than four glyphosate concentrations, and the $K_i$ of the EPSPS for glyphosate was calculated from the plot of $K_m$ apparent vs. glyphosate concentration, using the equation (m1*x/(m2+x); m1=1; m2=1) as known in the art.

TABLE 3

Kinetics of GRG23(ACE1) vs GRG23

| | Km (uM) | Ki (uM) | Vmax (nmol/min/ug) |
|---|---|---|---|
| GRG23 | 12.2 | 13,800 | 14.77 |
| GRG23(ACE1) | 9.7 | 14,620 | 13.73 |

Example 6

Identification of grg23 (ace2)

GRG23(ACE1) contains two amino acid changes relative to GRG23. To determine if additional substitutions at these positions could further improve activity, a DNA library was generated that resulted in clones expressing proteins that were substantially mutated at positions 49 and 276 corresponding to GRG23 (SEQ ID NO:2). Clones conferring glyphosate resistance were selected by growth on glyphosate plates, and grown and assayed for kinetic properties as described.

Surprisingly, one clone, herein designated grg23(ace2) (SEQ ID NO:10), encoding the GRG23(ACE2) protein (SEQ ID NO:11) was identified as having improved thermostability. The DNA sequence of grg23(ace2) shows that GRG23 (ACE2) contains a single amino acid change (residue 276 of GRG23 to arginine).

Example 7

Comparison of GRG23 and GRG51, and Mutagenesis of Differing Residues

Two libraries were generated to assess the permutations of amino acid sequences possible from comparison of the amino acid sequences of GRG23 and GRG51. The first library introduced variation from the GRG51 amino acid sequence into a grg23(ace2) coding region. The second library introduced the variation from GRG23(ACE2) amino acid sequence into the grg51 coding region.

Clones of the resulting libraries were assessed for (1) ability to confer glyphosate resistance upon on a cell, and (2) activity after prolonged incubation at 37° C. A total of ten clones was sequenced and analyzed in more detail. One particular clone, herein designated grg51.4 (SEQ ID NO:12), encoding the protein GRG51.4 (SEQ ID NO:13), contains several amino acid changes relative to both GRG23(ACE2) and GRG51. The amino acid changes present in GRG51.4 relative to GRG23(ACE2) were subsequently introduced into the grg23(ace2) gene, to yield grg23(ace3) (SEQ ID NO:14), which encodes the GRG23(ACE3) protein (SEQ ID NO:15). GRG23(ACE3) exhibits superior activity and thermostability relative to GRG23, and GRG23(ACE2).

GRG23(ace1) was mutagenized, and clones were tested to identify clones expressing variants with improved thermostability and/or activity. One clone, grg23(L5P2.J2) (SEQ ID NO:16), encoding GRG23(L5P2.J2) (SEQ ID NO:17), was identified by virtue of its improved kinetic properties. GRG23 (L5P2.J2) contains three amino acid changes relative to GRG23 (ACE1), as shown in the following Table 4.

TABLE 4

Amino Acid changes in GRG23(L5P2.J2)
Amino Acid (AA) in GRG23(L5P2.J2) relative to GRG23(ACE1)

V101→F
A213→S
D284→N

Oligonucleotide mutagenesis was used to modify the grg23(ace3) coding region to contain each of the amino acid changes identified in GRG23(L5P2.J2). A clone with a gene containing these modifications was identified, and found to encode a protein having altered kinetic properties over GRG23(ACE3). This gene was designated grg23(ace4) (SEQ ID NO:18). The protein encoded by grg23(ace4) and designated as GRG23(ACE4) (SEQ ID NO:19) contains a single amino acid change relative to GRG23(ACE3) (Valine 101 to phenylalanine). Based on this result, a separate oligonucleotide mutagenesis was performed to test the kinetics of each possible amino acid substitution at position 101. None of the amino acid changes resulted in further improvement in kinetic properties compared to GRG23(ACE4). See Table 5.

TABLE 5

Kinetics of improved variants

| | Km (µM) | Ki (µM) | Vmax (nmol/min/µg) |
|---|---|---|---|
| GRG23 | 14 | 10,800 | 13 |
| GRG51 | 15 | 21,048 | 13 |
| GRG23(ACE1) | 10 | 14,620 | 14 |
| GRG23(ACE2) | 11 | 18,104 | 15 |
| GRG51.4 | 19 | 26,610 | 17 |
| GRG23(ACE3) | 15 | 20,000 | 17 |
| GRG23(L5P2.J2) | 15 | 2,500 | 23 |
| GRG23(ACE4) | 14 | 5,010 | 24 |

Example 8

Improved Thermostability of GRG23 Variants

The thermostability of GRG23 and several variants were determined by incubation of protein samples at 37'C for a range of times, then determining the residual EPSPS activity as described herein, and comparing the activity to that of a control sample incubated at 4'C. Table 6 shows that the GRG23 variants GRG23(ACE1), GRG23(ACE2), and GRG23(ACE3) have improved thermostability.

TABLE 6

Thermostability of GRG23 and GRG23 variants

| Protein | $t_{1/2}$ at 37° C. |
|---|---|
| GRG23 | 10.1 |
| GRG23(ACE1) | 15.3 |
| GRG23(ACE2) | 34.2 |
| GRG23(ACE3) | 65.4 |

Example 9

Variants of grg23(ace3)

Oligonucleotide mutagenesis was utilized to generate variants of grg23(ace3) that result in expression of proteins with modifications to amino acid residues corresponding to positions 169 to 174 of SEQ ID NO:15. Mutagenesis reactions were carried out using the QuickChange® kit (Stratagene) according to the manufacturer's instructions. Plasmid clones were transformed into E. coli cell line BL21*DE3, and expression of proteins induced by IPTG as known in the art. The proteins were purified by affinity binding to a nickel column (TALON metal affinity resin, Clontech). The native GRG23(ace3) protein was also expressed and purified for use as a control. Following purification of each enzyme, protein concentration was measured by Bradford assay as known in the art.

Example 10

Kinetic Analysis of GRG23(ace3) Variants

GRG23(ace3) variants GRG23(ace3) R173K (SEQ ID NO:29, encoded by SEQ ID NO:28), GRG23(ace3) G169V/L170V (SEQ ID NO:31, encoded by SEQ ID NO:30), GRG23(ace3) R173Q (SEQ ID NO:33, encoded by SEQ ID NO:32), and GRG23(ace3) I174V (SEQ ID NO:35, encoded by SEQ ID NO:34) were characterized by enzymatic assays as described herein, and compared to the native GRG23(ace3) enzyme. For each enzyme the Km(app) was determined at each of several glyphosate concentrations, and a plot of Km(app) vs. glyphosate concentration was used to calculate the Ki for each enzyme. The thermostability for each enzyme was assessed by incubating the enzyme at 37° C. for 16 hours, and then quantifying the enzymatic activity remaining (as Vmax) vs. control enzyme that was incubated at 4° C.

Kinetic analysis reveals that GRG23(ace3)R173K, GRG23(ace3)R173Q, GRG23(ace3)I174V and GRG23(ace3)G169V/L170V are virtually indistinguishable from native GRG23(ace3) and show nearly identical catalytic rate, extremely high resistance to glyphosate, and very good affinity for PEP. The observed $K_m$ for PEP of 19 µM for G169V/L170V (vs 15 µM for GRG23(ace3) may represent a slightly lower binding affinity for PEP relative to GRG23(ace3). Each of the four variants had a thermostability of greater than 95% after 16 hours at 37° C. The kinetic values determined for the GRG23(ace3) variants GRG23(ace3) R173K, GRG23(ace3) R173Q, and GRG23(ace3) I174V are shown in Table 6.

TABLE 7

Kinetics of GRG23(ace3) variants

| | Km (µM) | Ki (mM) | Vmax (nmol/min/µg) |
|---|---|---|---|
| GRG23(ace3) | 16 | 14 | 16 |
| GRG23(ace3) R173K | 16.6 | 14.7 | 17.7 |
| GRG23(ace3) R173Q | 14.3 | 14.2 | 15.8 |
| GRG23(ace3) I174V | 15.5 | 15.0 | 15.5 |

Example 11

Cloning of syngrg23 and grg23 Variants into a Plant Expression Cassette

For syngrg23, and each of the grg23 variants described herein (including, for example, grg23(ace1), grg23(ace2), grg23(ace3), grg23(ace4), grg23(ace3)R173K, grg23(ace3) R173Q, grg23(ace3)I174V, grg23(ace3)G169V/L170V and grg23(L5P2.J2)), the open reading frame (ORF) is amplified by PCR from a full-length DNA template. Hind III restriction sites are added to each end of the ORFs during PCR. Additionally, the nucleotide sequence ACC is added immediately 5' to the start codon of the gene to increase translational efficiency (Kozak (1987) *Nucleic Acids Research* 15:8125-8148; Joshi (1987) *Nucleic Acids Research* 15:6643-6653). The PCR product is cloned and sequenced using techniques well known in the art to ensure that no mutations are introduced during PCR.

The plasmid containing the PCR product is digested with Hind III and the fragment containing the intact ORF is isolated. This fragment is cloned into the Hind III site of a plasmid such as pAX200, a plant expression vector containing the rice actin promoter (McElroy et al. (1991) *Molec. Gen. Genet.* 231:150-160) and the PinII terminator (An et al. (1989) *The Plant Cell* 1:115-122). The promoter-gene-terminator fragment from this intermediate plasmid is then subcloned into plasmid pSB11 (Japan Tobacco, Inc.) to form a final pSB11-based plasmid. In some cases, it may be preferable to generate an alternate construct in which a chloroplast leader sequence is encoded as a fusion to the N-terminus of the syngrg23, grg23(ace1), grg23(ace2), grg23(ace3), grg23 (ace4), grg23(L5P2.J2), grg23(ace3)R173K, grg23(ace3) R173Q, grg23(ace3)I174V, or grg23(ace3)G169V/L170V constructs. These pSB11-based plasmids are typically organized such that the DNA fragment containing the promoter-gene-terminator construct, or promoter-chloroplast leader-gene-terminator construct may be excised by double digestion by restriction enzymes, such as Kpn I and Pme I, and used for transformation into plants by aerosol beam injection. The structure of the resulting pSB11-based clones is verified by restriction digest and gel electrophoresis, and by sequencing across the various cloning junctions.

The plasmid is mobilized into *Agrobacterium tumefaciens* strain LBA4404 which also harbors the plasmid pSB1 (Japan Tobacco, Inc.), using triparental mating procedures well known in the art, and plating on media containing spectinomycin. The pSB11-based plasmid clone carries spectinomycin resistance but is a narrow host range plasmid and cannot replicate in *Agrobacterium*. Spectinomycin resistant colonies arise when pSB11-based plasmids integrate into the broad host range plasmid pSB1 through homologous recombination. The cointegrate product of pSB1 and the pSB11-based plasmid is verified by Southern hybridization. The *Agrobacterium* strain harboring the cointegrate is used to transform maize by methods known in the art, such as, for example, the PureIntro method (Japan Tobacco).

Example 12

Transformation of Plant Cells by *Agrobacterium*-Mediated Transformation

Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 ml/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 ml/L (of 1 mg/ml stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to express the GRG proteins of the present invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials
DN62A5S Media

| Components | per liter | Source |
|---|---|---|
| Chu's N6 Basal Salt Mixture (Prod. No. C 416) | 3.98 g/L | Phytotechnology Labs |
| Chu's N6 Vitamin Solution (Prod. No. C 149) | 1 ml/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 ml/L (of 1 mg/ml Stock) | Sigma |

Adjust the pH of the solution to pH 5.8 with 1N KOH/1N KCl, add Gelrite (Sigma) to 3 g/L, and autoclave. After cooling to 50° C., add 2 ml/L of a 5 mg/ml stock solution of Silver Nitrate (Phytotechnology Labs). Recipe yields about 20 plates.

Example 13

Transformation of EPSP Synthase Enzymes into Maize Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark.

However, it is not necessary per se to incubate the embryos overnight. Embryos are contacted with an *Agrobacterium* strain containing the appropriate vectors having an EPSP synthase enzyme of the present invention for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A recombinant nucleic acid molecule selected from the group consisting of:
   a) a nucleic acid molecule comprising the nucleotide sequence of SEQ ID NO:34; and,
   b) a nucleic acid molecule which encodes a polypeptide comprising the amino acid sequence of SEQ ID NO:35.

2. The recombinant nucleic acid molecule of claim 1, wherein said nucleotide sequence is a synthetic sequence that has been designed for expression in a plant.

3. A vector comprising the nucleic acid molecule of claim 1.

4. The vector of claim 3, further comprising a nucleic acid molecule encoding a heterologous polypeptide.

5. A host cell that contains the recombinant nucleic acid molecule of claim 1.

6. The host cell of claim 5 that is a bacterial host cell.

7. The host cell of claim 5 that is a plant cell.

8. A transgenic plant comprising the host cell of claim 7.

9. The plant of claim 8, wherein said plant is selected from the group consisting of maize, sorghum, wheat, sunflower, tomato, crucifers, peppers, potato, cotton, rice, soybean, sugarbeet, sugarcane, tobacco, barley, and oilseed rape.

10. A transgenic seed comprising the recombinant nucleic acid molecule of claim 1.

11. A method for producing a polypeptide with herbicide resistance activity, comprising culturing the host cell of claim 5 under conditions in which a nucleic acid molecule encoding the polypeptide is expressed.

12. A method for conferring resistance to an herbicide in a plant, said method comprising transforming said plant with a DNA construct, said construct comprising a promoter that drives expression in a plant cell operably linked with the nucleotide sequence of SEQ ID NO:34 or a nucleotide sequence encoding the amino acid sequence set forth in SEQ ID NO:35, and regenerating a transformed plant.

13. The method of claim 12, wherein said herbicide is glyphosate.

14. A plant having stably incorporated into its genome a DNA construct comprising a nucleotide sequence that encodes a protein having herbicide resistance activity, wherein said nucleotide sequence is selected from the group consisting of:
   a) a nucleic acid molecule comprising the nucleotide sequence of SEQ ID NO:34; and,
   b) a nucleic acid molecule which encodes a polypeptide comprising the amino acid sequence of SEQ ID NO:35;
   wherein said nucleotide sequence is operably linked to a promoter that drives expression of a coding sequence in a plant cell.

15. The plant of claim 14, wherein said plant is a plant cell.

16. The plant of claim 14, wherein said plant is a soybean plant.

17. The plant of claim 14, wherein said plant is a corn plant.

18. The plant of claim 14, wherein said plant is selected from the group consisting of maize, sorghum, wheat, sunflower, tomato, crucifers, peppers, potato, cotton, rice, soybean, sugarbeet, sugarcane, tobacco, barley, and oilseed rape.

19. A method for increasing vigor or yield in a plant comprising:
   a) providing a plant or seed thereof comprising the nucleotide sequence set forth in SEQ ID NO:34 or a nucleotide sequence encoding the amino acid sequence set forth in SEQ ID NO:35;
   b) contacting said plant with an effective concentration of glyphosate; and,
   c) growing said plant under conditions wherein the temperature is higher than ambient environmental temperature for at least two consecutive hours per day for at least four days following contact with said glyphosate, wherein said days following contact is within the growing season of the plant,
   wherein the vigor or yield of said plant is higher than the vigor or yield of a plant expressing a glyphosate tolerance EPSP synthase that does not have a temperature optimum higher than ambient environmental temperature.

20. The method of claim 19, wherein the temperature in step (c) is about 32° C. to about 60° C.

21. A method for conferring resistance to glyphosate in a plant comprising:
   a) providing a plant or seed thereof comprising the nucleotide sequence set forth in SEQ ID NO:34 or a nucleotide sequence encoding the amino acid sequence set forth in SEQ ID NO:35;
   b) contacting said plant with an effective concentration of glyphosate; and, c) growing said plant under conditions wherein the temperature is higher than ambient environmental temperature for at least two consecutive hours per day for at least four days following contact with said glyphosate, wherein said days following contact is within the growing season of the plant.

22. The method of claim 21, wherein the temperature in step (c) is about 32° C. to about 60° C.

23. The method of claim 22, wherein the temperature in step (b) is about 37° C.

24. The recombinant nucleic acid sequence of claim 1, wherein said nucleotide sequence is operably linked to a promoter that drives expression of said nucleotide sequence in a plant cell.

* * * * *

SEQUENCE LISTING

```
<160> NUMBER OF SEQ ID NOS: 35

<210> SEQ ID NO 1
<211> LENGTH: 1892
<212> TYPE: DNA
<213> ORGANISM: Arthrobacter globiformis
<220> FEATURE:
<221> NAME/KEY: CDS
<222> LOCATION: (178)...(1417)
<221> NAME/KEY: misc_feature
<222> LOCATION: 1801
<223> OTHER INFORMATION: n = A,T,C or G

<400> SEQUENCE: 1
gggaccacat gctgctcctg atttcagggc tgctgccggt atggaccagg gtttagagag      60
ggacggcacg catccgggcc cttatcggac caacgccaac agcggtcggt ggccttggag     120
cggggccagc acggccgatc acgtagactc tttggagctt cgctcgaaag gatcacc atg    180
                                                                  Met
                                                                   1 gaa act gat cga cta gtg atc cca gga tcg aaa agc atc acc aac cgg       228
Glu Thr Asp Arg Leu Val Ile Pro Gly Ser Lys Ser Ile Thr Asn Arg
          5                  10                  15 gct ttg ctt ttg gct gcc gca gcg aag ggc acg tcg gtc ctg gtg aga       276
Ala Leu Leu Leu Ala Ala Ala Ala Lys Gly Thr Ser Val Leu Val Arg
     20                  25                  30 cca ttg gtc agc gcc gat acc tca gca ttc aaa act gca att cag gcc       324
Pro Leu Val Ser Ala Asp Thr Ser Ala Phe Lys Thr Ala Ile Gln Ala
 35                  40                  45 ctc ggt gcc aac gtc tca gcc gac ggt gac aat tgg gtc gtt gaa ggc       372
Leu Gly Ala Asn Val Ser Ala Asp Gly Asp Asn Trp Val Val Glu Gly
 50                  55                  60                  65 ctg ggt cag gca ccc cac ctc gac gcc gac atc tgg tgc gag gat gca       420
Leu Gly Gln Ala Pro His Leu Asp Ala Asp Ile Trp Cys Glu Asp Ala
                 70                  75                  80 ggt acc gtg gcc cgg ttc ctc cct cca ttc gtc gcc gca gga cag ggg       468
Gly Thr Val Ala Arg Phe Leu Pro Pro Phe Val Ala Ala Gly Gln Gly
             85                  90                  95 aag ttc acc gtc gac gga agc gag cag ctg cgg cgg cgc ccg ctt cgg       516
Lys Phe Thr Val Asp Gly Ser Glu Gln Leu Arg Arg Arg Pro Leu Arg
         100                 105                 110 ccc ctg gtc gac ggc atc cgc cac ctg ggc gcc cgc gtc tcc tcc gag       564
Pro Leu Val Asp Gly Ile Arg His Leu Gly Ala Arg Val Ser Ser Glu
     115                 120                 125 cag ctg ccc cta aca att gaa gcg agc ggg ctg gca ggc ggg gag tac       612
Gln Leu Pro Leu Thr Ile Glu Ala Ser Gly Leu Ala Gly Gly Glu Tyr
130                 135                 140                 145 gaa att gaa gcc cat cag agc agc cag ttc gcc tcc ggc ctg atc atg       660
Glu Ile Glu Ala His Gln Ser Ser Gln Phe Ala Ser Gly Leu Ile Met
                 150                 155                 160 gcc gcc ccg tac gcg cga caa ggc ctg cgt gtg cgg ata cca aat ccc       708
Ala Ala Pro Tyr Ala Arg Gln Gly Leu Arg Val Arg Ile Pro Asn Pro
```

```
                 165                 170                 175
gtg agc cag ccc tac ctc acg atg aca ctg cgg atg atg agg gac ttc       756
Val Ser Gln Pro Tyr Leu Thr Met Thr Leu Arg Met Met Arg Asp Phe
            180                 185                 190 ggc ctt gag acc agc acc gac gga gcc acc gtc agc gtc cct ccc ggg       804
Gly Leu Glu Thr Ser Thr Asp Gly Ala Thr Val Ser Val Pro Pro Gly
195                 200                 205 cgc tac aca gcc cgg cgg tat gaa att gaa ccg gac gcg tca act gcg       852
Arg Tyr Thr Ala Arg Arg Tyr Glu Ile Glu Pro Asp Ala Ser Thr Ala
210                 215                 220                 225 tcg tac ttc gcc gcc gct tcc gcc gtc tct ggc cga agc ttc gaa ttc       900
Ser Tyr Phe Ala Ala Ala Ser Ala Val Ser Gly Arg Ser Phe Glu Phe
            230                 235                 240 cag ggc ctt ggc aca gac agc atc caa ggc gac acg tca ttc ttc aat       948
Gln Gly Leu Gly Thr Asp Ser Ile Gln Gly Asp Thr Ser Phe Phe Asn
            245                 250                 255 gta ctt ggg cgg ctc ggt gca gag gtc cac tgg gca ccc aac tcg gtc       996
Val Leu Gly Arg Leu Gly Ala Glu Val His Trp Ala Pro Asn Ser Val
        260                 265                 270 acc ata tcc gga ccg gaa agg ctg aac ggc gac att gaa gtg gat atg      1044
Thr Ile Ser Gly Pro Glu Arg Leu Asn Gly Asp Ile Glu Val Asp Met
275                 280                 285 ggc gag ata tcg gac acc ttc atg aca ctc gcg gcg att gcc cct cta      1092
Gly Glu Ile Ser Asp Thr Phe Met Thr Leu Ala Ala Ile Ala Pro Leu
290                 295                 300                 305 gcc gat gga ccc atc acg ata acc aac att ggc cat gca cgg ttg aag      1140
Ala Asp Gly Pro Ile Thr Ile Thr Asn Ile Gly His Ala Arg Leu Lys
            310                 315                 320 gaa tcc gac cgc atc tcg gcg atg gaa acc aac ctg cga acg ctc ggt      1188
Glu Ser Asp Arg Ile Ser Ala Met Glu Thr Asn Leu Arg Thr Leu Gly
            325                 330                 335 gta caa acc gac gtc gga cac gac tgg atg cga atc tac ccc tct acc      1236
Val Gln Thr Asp Val Gly His Asp Trp Met Arg Ile Tyr Pro Ser Thr
            340                 345                 350 ccg cac ggc ggc aga gtc aat tgc cac cgg gac cac agg atc gcc atg      1284
Pro His Gly Gly Arg Val Asn Cys His Arg Asp His Arg Ile Ala Met
355                 360                 365 gcg ttt tca atc ctg gga ctg cga gtg gac ggg att acc ctc gac gac      1332
Ala Phe Ser Ile Leu Gly Leu Arg Val Asp Gly Ile Thr Leu Asp Asp
370                 375                 380                 385 cct caa tgt gtc ggg aag acc ttt cct ggc ttc ttc gac tac ctt gga      1380
Pro Gln Cys Val Gly Lys Thr Phe Pro Gly Phe Phe Asp Tyr Leu Gly
            390                 395                 400 cgc ctt ttc ccc gaa aag gcg ctt acg ctc ccc ggc t agtgacttcc         1427
Arg Leu Phe Pro Glu Lys Ala Leu Thr Leu Pro Gly
            405                 410 tctccggcgg acgctaggca tcggaaaacg aatcctgaca tgaccgacct cctcgcgtca    1487
cggcgtgtct gccggtaccc aagcattctg ccttagccgc ttccgcgccc cttatgcttt    1547
tctggttgtc cagattttca tccgggatgt tgcctgacct tgagcagggc aatcagctgt    1607
tcagcactgt caatggtgtg ggccctgaag gcggcttcga tggctgccac gtcggcggct    1667
ctcatcgctg tcacgacacg cagatgcgct tcataggcac gttcaggatc cgccctcgtc    1727
gcctgatcct gagccaaggc aatagttaga tgtgcctccg ttggcggcca gagccgaagc    1787
aataaggagt tttncgaggc cacccagatt ccccgggtgg aaggcgatat gggcttcatg    1847
ctgaactatg gggtccggat ggaagtgact tttcaactct gccca                    1892
```

<210> SEQ ID NO 2

```
<211> LENGTH: 413
<212> TYPE: PRT
<213> ORGANISM: Arthrobacter globiformis

<400> SEQUENCE: 2
```

| | | | | | | | | | | | | | | |
|---|---|---|---|---|---|---|---|---|---|---|---|---|---|---|
| Met | Glu | Thr | Asp | Arg | Leu | Val | Ile | Pro | Gly | Ser | Lys | Ser | Ile | Thr | Asn |
| 1 | | | | 5 | | | | | 10 | | | | | 15 | |

| Arg | Ala | Leu | Leu | Leu | Ala | Ala | Ala | Lys | Gly | Thr | Ser | Val | Leu | Val |
|---|---|---|---|---|---|---|---|---|---|---|---|---|---|---|
| | | | 20 | | | | 25 | | | | 30 | | | |

| Arg | Pro | Leu | Val | Ser | Ala | Asp | Thr | Ser | Ala | Phe | Lys | Thr | Ala | Ile | Gln |
|---|---|---|---|---|---|---|---|---|---|---|---|---|---|---|---|
| | | 35 | | | | | 40 | | | | | 45 | | | |

| Ala | Leu | Gly | Ala | Asn | Val | Ser | Ala | Asp | Gly | Asp | Asn | Trp | Val | Val | Glu |
|---|---|---|---|---|---|---|---|---|---|---|---|---|---|---|---|
| | 50 | | | | | 55 | | | | | 60 | | | | |

| Gly | Leu | Gly | Gln | Ala | Pro | His | Leu | Asp | Ala | Asp | Ile | Trp | Cys | Glu | Asp |
|---|---|---|---|---|---|---|---|---|---|---|---|---|---|---|---|
| 65 | | | | | 70 | | | | | 75 | | | | | 80 |

| Ala | Gly | Thr | Val | Ala | Arg | Phe | Leu | Pro | Pro | Phe | Val | Ala | Ala | Gly | Gln |
|---|---|---|---|---|---|---|---|---|---|---|---|---|---|---|---|
| | | | | 85 | | | | | 90 | | | | | 95 | |

| Gly | Lys | Phe | Thr | Val | Asp | Gly | Ser | Glu | Gln | Leu | Arg | Arg | Pro | Leu |
|---|---|---|---|---|---|---|---|---|---|---|---|---|---|---|
| | | | 100 | | | | | 105 | | | | | 110 | |

| Arg | Pro | Leu | Val | Asp | Gly | Ile | Arg | His | Leu | Gly | Ala | Arg | Val | Ser | Ser |
|---|---|---|---|---|---|---|---|---|---|---|---|---|---|---|---|
| | | 115 | | | | | 120 | | | | | 125 | | | |

| Glu | Gln | Leu | Pro | Leu | Thr | Ile | Glu | Ala | Ser | Gly | Leu | Ala | Gly | Gly | Glu |
|---|---|---|---|---|---|---|---|---|---|---|---|---|---|---|---|
| | 130 | | | | | 135 | | | | | 140 | | | | |

| Tyr | Glu | Ile | Glu | Ala | His | Gln | Ser | Ser | Gln | Phe | Ala | Ser | Gly | Leu | Ile |
|---|---|---|---|---|---|---|---|---|---|---|---|---|---|---|---|
| 145 | | | | | 150 | | | | | 155 | | | | | 160 |

| Met | Ala | Ala | Pro | Tyr | Ala | Arg | Gln | Gly | Leu | Arg | Val | Arg | Ile | Pro | Asn |
|---|---|---|---|---|---|---|---|---|---|---|---|---|---|---|---|
| | | | | 165 | | | | | 170 | | | | | 175 | |

| Pro | Val | Ser | Gln | Pro | Tyr | Leu | Thr | Met | Thr | Leu | Arg | Met | Met | Arg | Asp |
|---|---|---|---|---|---|---|---|---|---|---|---|---|---|---|---|
| | | | 180 | | | | | 185 | | | | | 190 | | |

| Phe | Gly | Leu | Glu | Thr | Ser | Thr | Asp | Gly | Ala | Thr | Val | Ser | Val | Pro | Pro |
|---|---|---|---|---|---|---|---|---|---|---|---|---|---|---|---|
| | | | 195 | | | | | 200 | | | | | 205 | | |

| Gly | Arg | Tyr | Thr | Ala | Arg | Arg | Tyr | Glu | Ile | Glu | Pro | Asp | Ala | Ser | Thr |
|---|---|---|---|---|---|---|---|---|---|---|---|---|---|---|---|
| | 210 | | | | | 215 | | | | | 220 | | | | |

| Ala | Ser | Tyr | Phe | Ala | Ala | Ala | Ser | Ala | Val | Ser | Gly | Arg | Ser | Phe | Glu |
|---|---|---|---|---|---|---|---|---|---|---|---|---|---|---|---|
| 225 | | | | | 230 | | | | | 235 | | | | | 240 |

| Phe | Gln | Gly | Leu | Gly | Thr | Asp | Ser | Ile | Gln | Gly | Asp | Thr | Ser | Phe | Phe |
|---|---|---|---|---|---|---|---|---|---|---|---|---|---|---|---|
| | | | | 245 | | | | | 250 | | | | | 255 | |

| Asn | Val | Leu | Gly | Arg | Leu | Gly | Ala | Glu | Val | His | Trp | Ala | Pro | Asn | Ser |
|---|---|---|---|---|---|---|---|---|---|---|---|---|---|---|---|
| | | | 260 | | | | | 265 | | | | | 270 | | |

| Val | Thr | Ile | Ser | Gly | Pro | Glu | Arg | Leu | Asn | Gly | Asp | Ile | Glu | Val | Asp |
|---|---|---|---|---|---|---|---|---|---|---|---|---|---|---|---|
| | | 275 | | | | | 280 | | | | | 285 | | | |

| Met | Gly | Glu | Ile | Ser | Asp | Thr | Phe | Met | Thr | Leu | Ala | Ala | Ile | Ala | Pro |
|---|---|---|---|---|---|---|---|---|---|---|---|---|---|---|---|
| | 290 | | | | | 295 | | | | | 300 | | | | |

| Leu | Ala | Asp | Gly | Pro | Ile | Thr | Ile | Thr | Asn | Ile | Gly | His | Ala | Arg | Leu |
|---|---|---|---|---|---|---|---|---|---|---|---|---|---|---|---|
| 305 | | | | | 310 | | | | | 315 | | | | | 320 |

| Lys | Glu | Ser | Asp | Arg | Ile | Ser | Ala | Met | Glu | Thr | Asn | Leu | Arg | Thr | Leu |
|---|---|---|---|---|---|---|---|---|---|---|---|---|---|---|---|
| | | | | 325 | | | | | 330 | | | | | 335 | |

| Gly | Val | Gln | Thr | Asp | Val | Gly | His | Asp | Trp | Met | Arg | Ile | Tyr | Pro | Ser |
|---|---|---|---|---|---|---|---|---|---|---|---|---|---|---|---|
| | | | 340 | | | | | 345 | | | | | 350 | | |

| Thr | Pro | His | Gly | Gly | Arg | Val | Asn | Cys | His | Arg | Asp | His | Arg | Ile | Ala |
|---|---|---|---|---|---|---|---|---|---|---|---|---|---|---|---|
| | | | 355 | | | | | 360 | | | | | 365 | | |

| Met | Ala | Phe | Ser | Ile | Leu | Gly | Leu | Arg | Val | Asp | Gly | Ile | Thr | Leu | Asp |
|---|---|---|---|---|---|---|---|---|---|---|---|---|---|---|---|
| | 370 | | | | | 375 | | | | | 380 | | | | |

| Asp | Pro | Gln | Cys | Val | Gly | Lys | Thr | Phe | Pro | Gly | Phe | Phe | Asp | Tyr | Leu |
|---|---|---|---|---|---|---|---|---|---|---|---|---|---|---|---|
| 385 | | | | | 390 | | | | | 395 | | | | | 400 |

```
Gly Arg Leu Phe Pro Glu Lys Ala Leu Thr Leu Pro Gly
            405                 410

<210> SEQ ID NO 3
<211> LENGTH: 436
<212> TYPE: PRT
<213> ORGANISM: Arthrobacter globiformis

<400> SEQUENCE: 3

Met Ala Leu Glu Arg Gly Gln His Gly Arg Ser Arg Leu Phe Gly
 1               5                  10                  15

Ala Ser Leu Glu Arg Ile Thr Met Glu Thr Asp Arg Leu Val Ile Pro
                20                  25                  30

Gly Ser Lys Ser Ile Thr Asn Arg Ala Leu Leu Leu Ala Ala Ala
            35                  40                  45

Lys Gly Thr Ser Val Leu Val Arg Pro Leu Val Ser Ala Asp Thr Ser
     50                  55                  60

Ala Phe Lys Thr Ala Ile Gln Ala Leu Gly Ala Asn Val Ser Ala Asp
 65                  70                  75                  80

Gly Asp Asn Trp Val Val Glu Gly Leu Gly Gln Ala Pro His Leu Asp
                85                  90                  95

Ala Asp Ile Trp Cys Glu Asp Ala Gly Thr Val Ala Arg Phe Leu Pro
                100                 105                 110

Pro Phe Val Ala Ala Gly Gln Gly Lys Phe Thr Val Asp Gly Ser Glu
            115                 120                 125

Gln Leu Arg Arg Arg Pro Leu Arg Pro Leu Val Asp Gly Ile Arg His
            130                 135                 140

Leu Gly Ala Arg Val Ser Ser Glu Gln Leu Pro Leu Thr Ile Glu Ala
145                 150                 155                 160

Ser Gly Leu Ala Gly Gly Glu Tyr Glu Ile Glu Ala His Gln Ser Ser
                165                 170                 175

Gln Phe Ala Ser Gly Leu Ile Met Ala Ala Pro Tyr Ala Arg Gln Gly
            180                 185                 190

Leu Arg Val Arg Ile Pro Asn Pro Val Ser Gln Pro Tyr Leu Thr Met
            195                 200                 205

Thr Leu Arg Met Met Arg Asp Phe Gly Leu Glu Thr Ser Thr Asp Gly
    210                 215                 220

Ala Thr Val Ser Val Pro Pro Gly Arg Tyr Thr Ala Arg Arg Tyr Glu
225                 230                 235                 240

Ile Glu Pro Asp Ala Ser Thr Ala Ser Tyr Phe Ala Ala Ala Ser Ala
                245                 250                 255

Val Ser Gly Arg Ser Phe Glu Phe Gln Gly Leu Gly Thr Asp Ser Ile
            260                 265                 270

Gln Gly Asp Thr Ser Phe Phe Asn Val Leu Gly Arg Leu Gly Ala Glu
            275                 280                 285

Val His Trp Ala Pro Asn Ser Val Thr Ile Ser Gly Pro Glu Arg Leu
    290                 295                 300

Asn Gly Asp Ile Glu Val Asp Met Gly Glu Ile Ser Asp Thr Phe Met
305                 310                 315                 320

Thr Leu Ala Ala Ile Ala Pro Leu Ala Asp Gly Pro Ile Thr Ile
                325                 330                 335

Asn Ile Gly His Ala Arg Leu Lys Glu Ser Asp Arg Ile Ser Ala Met
            340                 345                 350

Glu Thr Asn Leu Arg Thr Leu Gly Val Gln Thr Asp Val Gly His Asp
            355                 360                 365
```

```
Trp Met Arg Ile Tyr Pro Ser Thr Pro His Gly Gly Arg Val Asn Cys
    370                 375                 380

His Arg Asp His Arg Ile Ala Met Ala Phe Ser Ile Leu Gly Leu Arg
385                 390                 395                 400

Val Asp Gly Ile Thr Leu Asp Asp Pro Gln Cys Val Gly Lys Thr Phe
                405                 410                 415

Pro Gly Phe Phe Asp Tyr Leu Gly Arg Leu Phe Pro Glu Lys Ala Leu
            420                 425                 430

Thr Leu Pro Gly
        435

<210> SEQ ID NO 4
<211> LENGTH: 1242
<212> TYPE: DNA
<213> ORGANISM: Unknown
<220> FEATURE:
<223> OTHER INFORMATION: isolated from soil sample
<221> NAME/KEY: CDS
<222> LOCATION: (1)...(1242)

<400> SEQUENCE: 4 atg gaa act gat cga cta gtg atc cca gga tcg aaa agc atc acc aac    48
Met Glu Thr Asp Arg Leu Val Ile Pro Gly Ser Lys Ser Ile Thr Asn
 1               5                  10                  15 cgg gct ttg ctt ttg gct gcc gca gcg aag ggc gcg tcg gtc ctg gtg    96
Arg Ala Leu Leu Leu Ala Ala Ala Ala Lys Gly Ala Ser Val Leu Val
                20                  25                  30 aga cca ttg gtc agc gcc gat acc tca gca ttc aaa act gca att cag   144
Arg Pro Leu Val Ser Ala Asp Thr Ser Ala Phe Lys Thr Ala Ile Gln
            35                  40                  45 gcc ctc ggt gcc aac gtc tca gcg gac ggt gat gat tgg gtc gtt gaa   192
Ala Leu Gly Ala Asn Val Ser Ala Asp Gly Asp Asp Trp Val Val Glu
        50                  55                  60 ggc ctg ggc cag gca ccc aac ctc gac gcc gac atc tgg tgc gag gat   240
Gly Leu Gly Gln Ala Pro Asn Leu Asp Ala Asp Ile Trp Cys Glu Asp
 65                 70                  75                  80 gcc ggt acc gtg gcc cgg ttc ctc cct cca ttc gtc gcc gca gga cag   288
Ala Gly Thr Val Ala Arg Phe Leu Pro Pro Phe Val Ala Ala Gly Gln
                85                  90                  95 ggg aag ttc acc gtc gac gga agc gag cag ctg cgg cgg cgc ccg ctt   336
Gly Lys Phe Thr Val Asp Gly Ser Glu Gln Leu Arg Arg Arg Pro Leu
            100                 105                 110 cgg ccc gtg gtc gac ggc atc cgc cac ctg ggc gcc cgc gtc tcc tcc   384
Arg Pro Val Val Asp Gly Ile Arg His Leu Gly Ala Arg Val Ser Ser
        115                 120                 125 gag cag ctg ccc cta acg att gaa gcg agc ggg ctg gca ggg ggg gag   432
Glu Gln Leu Pro Leu Thr Ile Glu Ala Ser Gly Leu Ala Gly Gly Glu
130                 135                 140 tac gaa att gaa gcc cat cag agc agc cag ttc gcc tcc ggt ctg atc   480
Tyr Glu Ile Glu Ala His Gln Ser Ser Gln Phe Ala Ser Gly Leu Ile
145                 150                 155                 160 atg gcc gcc ccg tac gcg cga caa ggc ctg cgt gtt cgg ata cca aat   528
Met Ala Ala Pro Tyr Ala Arg Gln Gly Leu Arg Val Arg Ile Pro Asn
                165                 170                 175 ccc gtg agc cag ccc tac ctc acg atg aca ctg cgg atg atg agg gac   576
Pro Val Ser Gln Pro Tyr Leu Thr Met Thr Leu Arg Met Met Arg Asp
            180                 185                 190 ttc ggc att gag acc agc acc gac gga gcg acc gtc agc gtt cct ccc   624
Phe Gly Ile Glu Thr Ser Thr Asp Gly Ala Thr Val Ser Val Pro Pro
        195                 200                 205
```

```
ggg cgc tac aca gcg cgg cgg tat gag att gaa ccg gac gcg tca act        672
Gly Arg Tyr Thr Ala Arg Arg Tyr Glu Ile Glu Pro Asp Ala Ser Thr
    210             215                 220 gcg tcg tac ttc gcc gcc gct tcc gcc gtc tct ggc cgg cgc ttc gaa        720
Ala Ser Tyr Phe Ala Ala Ala Ser Ala Val Ser Gly Arg Arg Phe Glu
225             230                 235                 240 ttc cag ggc ctt ggc aca gac agc atc caa ggc gac acg tca ttc ttc        768
Phe Gln Gly Leu Gly Thr Asp Ser Ile Gln Gly Asp Thr Ser Phe Phe
            245                 250                 255 aat gta ctt ggg cgg ctc ggc gca gag gtc cac tgg gca tcc aac tcg        816
Asn Val Leu Gly Arg Leu Gly Ala Glu Val His Trp Ala Ser Asn Ser
        260                 265                 270 gtc acc ata tcc gga ccg gaa agg ctg acc ggc gac att gaa gtg gat        864
Val Thr Ile Ser Gly Pro Glu Arg Leu Thr Gly Asp Ile Glu Val Asp
    275                 280                 285 atg ggc gag ata tcg gac acc ttc atg aca ctg gcg gcg att gcc cct        912
Met Gly Glu Ile Ser Asp Thr Phe Met Thr Leu Ala Ala Ile Ala Pro
290                 295                 300 cta gcc gat gga ccc atc acg ata aca aac att ggc cat gca cgg ttg        960
Leu Ala Asp Gly Pro Ile Thr Ile Thr Asn Ile Gly His Ala Arg Leu
305                 310                 315                 320 aag gaa tcc gac cgc atc tcg gcg atg gaa agc aac ctt cga atg ctc       1008
Lys Glu Ser Asp Arg Ile Ser Ala Met Glu Ser Asn Leu Arg Met Leu
                325                 330                 335 ggt gta caa acc gac gtc gga cac gac tgg atg cga atc tac ccc tct       1056
Gly Val Gln Thr Asp Val Gly His Asp Trp Met Arg Ile Tyr Pro Ser
            340                 345                 350 acc ccg cac ggc ggc aga gtc aat tgc cac cgg gac cac agg atc gcc       1104
Thr Pro His Gly Gly Arg Val Asn Cys His Arg Asp His Arg Ile Ala
        355                 360                 365 atg gcg ttt tca atc ctg gga ctg cga gtg gac ggg att acc ctc gac       1152
Met Ala Phe Ser Ile Leu Gly Leu Arg Val Asp Gly Ile Thr Leu Asp
    370                 375                 380 gac cct caa tgt gtc ggg aag acc ttt cct ggc ttc ttc gac tac ctt       1200
Asp Pro Gln Cys Val Gly Lys Thr Phe Pro Gly Phe Phe Asp Tyr Leu
385                 390                 395                 400 gga cgc ctt ttc ccg gaa aag gcg ctt acg ctc ccc ggc tag               1242
Gly Arg Leu Phe Pro Glu Lys Ala Leu Thr Leu Pro Gly
                405                 410

<210> SEQ ID NO 5
<211> LENGTH: 413
<212> TYPE: PRT
<213> ORGANISM: Unknown
<220> FEATURE:
<223> OTHER INFORMATION: isolated from soil sample

<400> SEQUENCE: 5

Met Glu Thr Asp Arg Leu Val Ile Pro Gly Ser Lys Ser Ile Thr Asn
 1               5                  10                  15

Arg Ala Leu Leu Leu Ala Ala Ala Lys Gly Ala Ser Val Leu Val
                20                  25                  30

Arg Pro Leu Val Ser Ala Asp Thr Ser Ala Phe Lys Thr Ala Ile Gln
            35                  40                  45

Ala Leu Gly Ala Asn Val Ser Ala Asp Gly Asp Trp Val Val Glu
        50                  55                  60

Gly Leu Gly Gln Ala Pro Asn Leu Asp Ala Asp Ile Trp Cys Glu Asp
65                  70                  75                  80

Ala Gly Thr Val Ala Arg Phe Leu Pro Pro Phe Val Ala Ala Gly Gln
                85                  90                  95
```

-continued

```
Gly Lys Phe Thr Val Asp Gly Ser Glu Gln Leu Arg Arg Pro Leu
            100                 105                 110
Arg Pro Val Asp Gly Ile Arg His Leu Gly Ala Arg Val Ser Ser
        115                 120                 125
Glu Gln Leu Pro Leu Thr Ile Glu Ala Ser Gly Leu Ala Gly Gly Glu
    130                 135                 140
Tyr Glu Ile Glu Ala His Gln Ser Ser Gln Phe Ala Ser Gly Leu Ile
145                 150                 155                 160
Met Ala Ala Pro Tyr Ala Arg Gln Gly Leu Arg Val Arg Ile Pro Asn
                165                 170                 175
Pro Val Ser Gln Pro Tyr Leu Thr Met Thr Leu Arg Met Met Arg Asp
            180                 185                 190
Phe Gly Ile Glu Thr Ser Thr Asp Gly Ala Thr Val Ser Val Pro Pro
        195                 200                 205
Gly Arg Tyr Thr Ala Arg Arg Tyr Glu Ile Glu Pro Asp Ala Ser Thr
    210                 215                 220
Ala Ser Tyr Phe Ala Ala Ser Ala Val Ser Gly Arg Arg Phe Glu
225                 230                 235                 240
Phe Gln Gly Leu Gly Thr Asp Ser Ile Gln Gly Asp Thr Ser Phe Phe
                245                 250                 255
Asn Val Leu Gly Arg Leu Gly Ala Glu Val His Trp Ala Ser Asn Ser
            260                 265                 270
Val Thr Ile Ser Gly Pro Glu Arg Leu Thr Gly Asp Ile Glu Val Asp
        275                 280                 285
Met Gly Glu Ile Ser Asp Thr Phe Met Thr Leu Ala Ala Ile Ala Pro
    290                 295                 300
Leu Ala Asp Gly Pro Ile Thr Ile Thr Asn Ile Gly His Ala Arg Leu
305                 310                 315                 320
Lys Glu Ser Asp Arg Ile Ser Ala Met Glu Ser Asn Leu Arg Met Leu
                325                 330                 335
Gly Val Gln Thr Asp Val Gly His Asp Trp Met Arg Ile Tyr Pro Ser
            340                 345                 350
Thr Pro His Gly Arg Val Asn Cys His Arg Asp His Arg Ile Ala
        355                 360                 365
Met Ala Phe Ser Ile Leu Gly Leu Arg Val Asp Gly Ile Thr Leu Asp
    370                 375                 380
Asp Pro Gln Cys Val Gly Lys Thr Phe Pro Gly Phe Phe Asp Tyr Leu
385                 390                 395                 400
Gly Arg Leu Phe Pro Glu Lys Ala Leu Thr Leu Pro Gly
                405                 410
```

<210> SEQ ID NO 6
<211> LENGTH: 1242
<212> TYPE: DNA
<213> ORGANISM: Artificial Sequence
<220> FEATURE:
<223> OTHER INFORMATION: synthetic grg23
<221> NAME/KEY: CDS
<222> LOCATION: (1)...(1242)

<400> SEQUENCE: 6

```
atg gaa act gat cgc ctt gtg atc cca gga tcg aaa agc atc acc aac    48
Met Glu Thr Asp Arg Leu Val Ile Pro Gly Ser Lys Ser Ile Thr Asn
  1               5                  10                  15 cgg gct ttg ctt ttg gct gcc gca gcg aag ggc acg tcg gtc ctg gtg    96
Arg Ala Leu Leu Leu Ala Ala Ala Ala Lys Gly Thr Ser Val Leu Val
                 20                  25                  30
```

```
aga cca ttg gtc agc gcc gat acc tca gca ttc aaa act gca atc cag      144
Arg Pro Leu Val Ser Ala Asp Thr Ser Ala Phe Lys Thr Ala Ile Gln
        35                  40                  45 gcc ctc ggt gcc aac gtc tca gcc gac ggt gac aat tgg gtc gtt gaa      192
Ala Leu Gly Ala Asn Val Ser Ala Asp Gly Asp Asn Trp Val Val Glu
 50                  55                  60 ggc ctg ggt cag gca ccc cac ctc gac gcc gac atc tgg tgc gag gac      240
Gly Leu Gly Gln Ala Pro His Leu Asp Ala Asp Ile Trp Cys Glu Asp
 65                  70                  75                  80 gca ggt act gtg gcc cgg ttc ctc cct cca ttc gta gcc gca ggt cag      288
Ala Gly Thr Val Ala Arg Phe Leu Pro Pro Phe Val Ala Ala Gly Gln
                 85                  90                  95 ggg aag ttc acc gtc gac gga tca gag cag ctg cgg cgg cgc ccg ctt      336
Gly Lys Phe Thr Val Asp Gly Ser Glu Gln Leu Arg Arg Arg Pro Leu
            100                 105                 110 cgg ccc ctg gtc gac ggc atc cgc cac ctg ggc gcc cgc gtc tcc tcc      384
Arg Pro Leu Val Asp Gly Ile Arg His Leu Gly Ala Arg Val Ser Ser
        115                 120                 125 gag cag ctg ccc ctt aca att gaa gcg agc ggg ctg gca ggc ggg gag      432
Glu Gln Leu Pro Leu Thr Ile Glu Ala Ser Gly Leu Ala Gly Gly Glu
130                 135                 140 tac gaa att gaa gcc cat cag agc agc cag ttc gcc tcc ggc ctg atc      480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat      528
Met Ala Ala Pro Tyr Ala Arg Gln Gly Leu Arg Val Arg Ile Pro Asn
                165                 170                 175 ccc gtg tca cag ccc tac ctc acg atg aca ctg cgg atg atg agg gac      576
Pro Val Ser Gln Pro Tyr Leu Thr Met Thr Leu Arg Met Met Arg Asp
            180                 185                 190 ttc ggc ctt gag acc agc acc gac gga gcc acc gtc agc gtc cct cca      624
Phe Gly Leu Glu Thr Ser Thr Asp Gly Ala Thr Val Ser Val Pro Pro
        195                 200                 205 ggg cgc tac aca gcc cgg cgg tat gaa ata gaa ccg gat gcg tca act      672
Gly Arg Tyr Thr Ala Arg Arg Tyr Glu Ile Glu Pro Asp Ala Ser Thr
210                 215                 220 gcg tcg tac ttc gcc gcc gct tcc gcc gtc tct ggc agg agc ttc gaa      720
Ala Ser Tyr Phe Ala Ala Ala Ser Ala Val Ser Gly Arg Ser Phe Glu
225                 230                 235                 240 ttt caa ggc ctt ggc aca gac agc atc caa ggc gac acg tca ttc ttc      768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca ccc aac tcg      816
Asn Val Leu Gly Arg Leu Gly Ala Glu Val His Trp Ala Pro Asn Ser
            260                 265                 270 gtc acc ata tct gga ccg gaa agg ctg aac ggc gac att gaa gtg gat      864
Val Thr Ile Ser Gly Pro Glu Arg Leu Asn Gly Asp Ile Glu Val Asp
        275                 280                 285 atg ggc gag att tcg gac acc ttc atg aca ctc gcg gcg att gcc cct      912
Met Gly Glu Ile Ser Asp Thr Phe Met Thr Leu Ala Ala Ile Ala Pro
290                 295                 300 ttg gcc gat gga ccc atc acg ata acc aac att ggt cat gca cgg ttg      960
Leu Ala Asp Gly Pro Ile Thr Ile Thr Asn Ile Gly His Ala Arg Leu
305                 310                 315                 320 aag gaa tcc gac cgc atc tca gcg atg gaa acc aac ctg cgc acg ctc     1008
Lys Glu Ser Asp Arg Ile Ser Ala Met Glu Thr Asn Leu Arg Thr Leu
                325                 330                 335 ggt gta caa acc gac gtc gga cac gac tgg atg aga atc tac ccc tct     1056
Gly Val Gln Thr Asp Val Gly His Asp Trp Met Arg Ile Tyr Pro Ser
            340                 345                 350
```

```
acc  ccg  cac  ggc  ggt  aga  gtg  aat  tgc  cac  cgg  gac  cac  agg  atc  gct    1104
Thr  Pro  His  Gly  Gly  Arg  Val  Asn  Cys  His  Arg  Asp  His  Arg  Ile  Ala
          355                 360                 365 atg  gcg  ttt  tca  atc  ctg  gga  ctg  aga  gtg  gac  ggg  att  acc  ctc  gac    1152
Met  Ala  Phe  Ser  Ile  Leu  Gly  Leu  Arg  Val  Asp  Gly  Ile  Thr  Leu  Asp
     370                 375                 380 gac  cct  caa  tgc  gtc  ggg  aag  acc  ttt  cct  ggc  ttc  ttc  gac  tac  ctt    1200
Asp  Pro  Gln  Cys  Val  Gly  Lys  Thr  Phe  Pro  Gly  Phe  Phe  Asp  Tyr  Leu
385                 390                 395                           400 gga  cgc  ctt  ttc  ccc  gaa  aag  gcg  ctt  acg  ctc  ccc  ggc  tag              1242
Gly  Arg  Leu  Phe  Pro  Glu  Lys  Ala  Leu  Thr  Leu  Pro  Gly
               405                 410
```

<210> SEQ ID NO 7
<211> LENGTH: 413
<212> TYPE: PRT
<213> ORGANISM: Artificial Sequence
<220> FEATURE:
<223> OTHER INFORMATION: synthetic GRG23

<400> SEQUENCE: 7

```
Met Glu Thr Asp Arg Leu Val Ile Pro Gly Ser Lys Ser Ile Thr Asn
 1               5                  10                  15

Arg Ala Leu Leu Leu Ala Ala Ala Lys Gly Thr Ser Val Leu Val
                 20                  25                  30

Arg Pro Leu Val Ser Ala Asp Thr Ser Ala Phe Lys Thr Ala Ile Gln
             35                  40                  45

Ala Leu Gly Ala Asn Val Ser Ala Asp Gly Asp Asn Trp Val Val Glu
         50                  55                  60

Gly Leu Gly Gln Ala Pro His Leu Asp Ala Asp Ile Trp Cys Glu Asp
 65                  70                  75                  80

Ala Gly Thr Val Ala Arg Phe Leu Pro Pro Phe Val Ala Ala Gly Gln
                 85                  90                  95

Gly Lys Phe Thr Val Asp Gly Ser Glu Gln Leu Arg Arg Arg Pro Leu
            100                 105                 110

Arg Pro Leu Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Leu Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ser Ala Val Ser Gly Arg Ser Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Pro Asn Ser
            260                 265                 270

Val Thr Ile Ser Gly Pro Glu Arg Leu Asn Gly Asp Ile Glu Val Asp
        275                 280                 285
```

```
Met Gly Glu Ile Ser Asp Thr Phe Met Thr Leu Ala Ala Ile Ala Pro
        290                 295                 300
Leu Ala Asp Gly Pro Ile Thr Ile Thr Asn Ile Gly His Ala Arg Leu
305                 310                 315                 320
Lys Glu Ser Asp Arg Ile Ser Ala Met Glu Thr Asn Leu Arg Thr Leu
                    325                 330                 335
Gly Val Gln Thr Asp Val Gly His Asp Trp Met Arg Ile Tyr Pro Ser
                340                 345                 350
Thr Pro His Gly Gly Arg Val Asn Cys His Arg Asp His Arg Ile Ala
            355                 360                 365
Met Ala Phe Ser Ile Leu Gly Leu Arg Val Asp Gly Ile Thr Leu Asp
        370                 375                 380
Asp Pro Gln Cys Val Gly Lys Thr Phe Pro Gly Phe Phe Asp Tyr Leu
385                 390                 395                 400
Gly Arg Leu Phe Pro Glu Lys Ala Leu Thr Leu Pro Gly
                405                 410
```

<210> SEQ ID NO 8
<211> LENGTH: 1242
<212> TYPE: DNA
<213> ORGANISM: Artificial Sequence
<220> FEATURE:
<223> OTHER INFORMATION: grg23(ace1)
<221> NAME/KEY: CDS
<222> LOCATION: (1)...(1242)

<400> SEQUENCE: 8

```
atg gaa act gat cgc ctt gtg atc cca gga tcg aaa agc atc acc aac    48
Met Glu Thr Asp Arg Leu Val Ile Pro Gly Ser Lys Ser Ile Thr Asn
  1               5                  10                  15 cgg gct ttg ctt ttg gct gcc gca gcg aag ggc acg tcg gtc ctg gtg    96
Arg Ala Leu Leu Leu Ala Ala Ala Ala Lys Gly Thr Ser Val Leu Val
             20                  25                  30 aga cca ttg gtc agc gcc gat acc tca gca ttc aaa act gca atc cag   144
Arg Pro Leu Val Ser Ala Asp Thr Ser Ala Phe Lys Thr Ala Ile Gln
         35                  40                  45 acc ctc ggt gcc aac gtc tca gcc gac ggt gac aat tgg gtc gtt gaa   192
Thr Leu Gly Ala Asn Val Ser Ala Asp Gly Asp Asn Trp Val Val Glu
 50                  55                  60 ggc ctg ggt cag gca ccc cac ctc gac gcc gac atc tgg tgc gag gac   240
Gly Leu Gly Gln Ala Pro His Leu Asp Ala Asp Ile Trp Cys Glu Asp
 65                  70                  75                  80 gca ggt act gtg gcc cgg ttc ctc cct cca ttc gta gcc gca ggt cag   288
Ala Gly Thr Val Ala Arg Phe Leu Pro Pro Phe Val Ala Ala Gly Gln
                 85                  90                  95 ggg aag ttc acc gtc gac gga tca gag cag ctg cgg cgg cgc ccg ctt   336
Gly Lys Phe Thr Val Asp Gly Ser Glu Gln Leu Arg Arg Arg Pro Leu
            100                 105                 110 cgg ccc ctg gtc gac ggc atc cgc cac ctg ggc gcc cgc gtc tcc tcc   384
Arg Pro Leu Val Asp Gly Ile Arg His Leu Gly Ala Arg Val Ser Ser
        115                 120                 125 gag cag ctg ccc ctt aca att gaa gcg agc ggg ctg gca ggg ggg gag   432
Glu Gln Leu Pro Leu Thr Ile Glu Ala Ser Gly Leu Ala Gly Gly Glu
    130                 135                 140 tac gaa att gaa gcc cat cag agc agc cag ttc gcc tcc ggc ctg atc   480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat   528
Met Ala Ala Pro Tyr Ala Arg Gln Gly Leu Arg Val Arg Ile Pro Asn
                165                 170                 175
```

```
ccc gtg tca cag ccc tac ctc acg atg aca ctg cgg atg atg agg gac      576
Pro Val Ser Gln Pro Tyr Leu Thr Met Thr Leu Arg Met Met Arg Asp
            180                 185                 190 ttc ggc ctt gag acc agc acc gac gga gcc acc gtc agc gtc cct cca      624
Phe Gly Leu Glu Thr Ser Thr Asp Gly Ala Thr Val Ser Val Pro Pro
                195                 200                 205 ggg cgc tac aca gcc cgg cgg tat gaa ata gaa ccg gat gcg tca act      672
Gly Arg Tyr Thr Ala Arg Arg Tyr Glu Ile Glu Pro Asp Ala Ser Thr
            210                 215                 220 gcg tcg tac ttc gcc gcc gct tcc gcc gtc tct ggc agg agc ttc gaa      720
Ala Ser Tyr Phe Ala Ala Ala Ser Ala Val Ser Gly Arg Ser Phe Glu
225                 230                 235                 240 ttt caa ggc ctt ggc aca gac agc atc caa ggc gac acg tca ttc ttc      768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca ccc aac tcg      816
Asn Val Leu Gly Arg Leu Gly Ala Glu Val His Trp Ala Pro Asn Ser
            260                 265                 270 gtc acc ata act gga ccg gaa agg ctg aac ggc gac att gaa gtg gat      864
Val Thr Ile Thr Gly Pro Glu Arg Leu Asn Gly Asp Ile Glu Val Asp
                275                 280                 285 atg ggc gag att tcg gac acc ttc atg aca ctc gcg gcg att gcc cct      912
Met Gly Glu Ile Ser Asp Thr Phe Met Thr Leu Ala Ala Ile Ala Pro
            290                 295                 300 ttg gcc gat gga ccc atc acg ata acc aac att ggt cat gca cgg ttg      960
Leu Ala Asp Gly Pro Ile Thr Ile Thr Asn Ile Gly His Ala Arg Leu
305                 310                 315                 320 aag gaa tcc gac cgc atc tca gcg atg gaa acc aac ctg cgc acg ctc     1008
Lys Glu Ser Asp Arg Ile Ser Ala Met Glu Thr Asn Leu Arg Thr Leu
                325                 330                 335 ggt gta caa acc gac gtc gga cac gac tgg atg aga atc tac ccc tct     1056
Gly Val Gln Thr Asp Val Gly His Asp Trp Met Arg Ile Tyr Pro Ser
            340                 345                 350 acc ccg cac ggc ggt aga gtg aat tgc cac cgg gac cac agg atc gct     1104
Thr Pro His Gly Gly Arg Val Asn Cys His Arg Asp His Arg Ile Ala
                355                 360                 365 atg gcg ttt tca atc ctg gga ctg aga gtg gac ggg att acc ctc gac     1152
Met Ala Phe Ser Ile Leu Gly Leu Arg Val Asp Gly Ile Thr Leu Asp
            370                 375                 380 gac cct caa tgc gtc ggg aag acc ttt cct ggc ttc ttc gac tac ctt     1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag             1242
Gly Arg Leu Phe Pro Glu Lys Ala Leu Thr Leu Pro Gly
                405                 410

<210> SEQ ID NO 9
<211> LENGTH: 413
<212> TYPE: PRT
<213> ORGANISM: Artificial Sequence
<220> FEATURE:
<223> OTHER INFORMATION: GRG23(ACE1)

<400> SEQUENCE: 9

Met Glu Thr Asp Arg Leu Val Ile Pro Gly Ser Lys Ser Ile Thr Asn
1               5                   10                  15

Arg Ala Leu Leu Leu Ala Ala Ala Ala Lys Gly Thr Ser Val Leu Val
                20                  25                  30

Arg Pro Leu Val Ser Ala Asp Thr Ser Ala Phe Lys Thr Ala Ile Gln
            35                  40                  45

Thr Leu Gly Ala Asn Val Ser Ala Asp Gly Asp Asn Trp Val Val Glu
```

```
              50                  55                  60
Gly Leu Gly Gln Ala Pro His Leu Asp Ala Asp Ile Trp Cys Glu Asp
 65                  70                  75                  80

Ala Gly Thr Val Ala Arg Phe Leu Pro Pro Phe Val Ala Ala Gly Gln
                 85                  90                  95

Gly Lys Phe Thr Val Asp Gly Ser Glu Gln Leu Arg Arg Arg Pro Leu
            100                 105                 110

Arg Pro Leu Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Leu Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ser Ala Val Ser Gly Arg Ser Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Pro Asn Ser
            260                 265                 270

Val Thr Ile Thr Gly Pro Glu Arg Leu Asn Gly Asp Ile Glu Val Asp
        275                 280                 285

Met Gly Glu Ile Ser Asp Thr Phe Met Thr Leu Ala Ala Ile Ala Pro
    290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Thr Asn Leu Arg Thr Leu
                325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
        355                 360                 365

Met Ala Phe Ser Ile Leu Gly Leu Arg Val Asp Gly Ile Thr Leu Asp
    370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410

<210> SEQ ID NO 10
<211> LENGTH: 1242
<212> TYPE: DNA
<213> ORGANISM: Artificial Sequence
<220> FEATURE:
<223> OTHER INFORMATION: grg23(ace2)
<221> NAME/KEY: CDS
<222> LOCATION: (1)...(1242)

<400> SEQUENCE: 10
```

```
atg gaa act gat cgc ctt gtg atc cca gga tcg aaa agc atc acc aac      48
Met Glu Thr Asp Arg Leu Val Ile Pro Gly Ser Lys Ser Ile Thr Asn
1               5                   10                  15 cgg gct ttg ctt ttg gct gcc gca gcg aag ggc acg tcg gtc ctg gtg      96
Arg Ala Leu Leu Leu Ala Ala Ala Ala Lys Gly Thr Ser Val Leu Val
            20                  25                  30 aga cca ttg gtc agc gcc gat acc tca gca ttc aaa act gca atc cag     144
Arg Pro Leu Val Ser Ala Asp Thr Ser Ala Phe Lys Thr Ala Ile Gln
        35                  40                  45 gcc ctc ggt gcc aac gtc tca gcc gac ggt gac aat tgg gtc gtt gaa     192
Ala Leu Gly Ala Asn Val Ser Ala Asp Gly Asp Asn Trp Val Val Glu
    50                  55                  60 ggc ctg ggt cag gca ccc cac ctc gac gcc gac atc tgg tgc gag gac     240
Gly Leu Gly Gln Ala Pro His Leu Asp Ala Asp Ile Trp Cys Glu Asp
65                  70                  75                  80 gca ggt act gtg gcc cgg ttc ctc cct cca ttc gta gcc gca ggt cag     288
Ala Gly Thr Val Ala Arg Phe Leu Pro Pro Phe Val Ala Ala Gly Gln
                85                  90                  95 ggg aag ttc acc gtc gac gga tca gag cag ctg cgg cgg cgc ccg ctt     336
Gly Lys Phe Thr Val Asp Gly Ser Glu Gln Leu Arg Arg Arg Pro Leu
            100                 105                 110 cgg ccc ctg gtc gac ggc atc cgc cac ctg ggc gcc cgc gtc tcc tcc     384
Arg Pro Leu Val Asp Gly Ile Arg His Leu Gly Ala Arg Val Ser Ser
        115                 120                 125 gag cag ctg ccc ctt aca att gaa gcg agc ggg ctg gca ggc ggg gag     432
Glu Gln Leu Pro Leu Thr Ile Glu Ala Ser Gly Leu Ala Gly Gly Glu
    130                 135                 140 tac gaa att gaa gcc cat cag agc agc cag ttc gcc tcc ggc ctg atc     480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat     528
Met Ala Ala Pro Tyr Ala Arg Gln Gly Leu Arg Val Arg Ile Pro Asn
                165                 170                 175 ccc gtg tca cag ccc tac ctc acg atg aca ctg cgg atg atg agg gac     576
Pro Val Ser Gln Pro Tyr Leu Thr Met Thr Leu Arg Met Met Arg Asp
            180                 185                 190 ttc ggc ctt gag acc agc acc gac gga gcc acc gtc agc gtc cct cca     624
Phe Gly Leu Glu Thr Ser Thr Asp Gly Ala Thr Val Ser Val Pro Pro
        195                 200                 205 ggg cgc tac aca gcc cgg cgg tat gaa ata gaa ccg gat gcg tca act     672
Gly Arg Tyr Thr Ala Arg Arg Tyr Glu Ile Glu Pro Asp Ala Ser Thr
    210                 215                 220 gcg tcg tac ttc gcc gcc gct tcc gcc gtc tct ggc agg agc ttc gaa     720
Ala Ser Tyr Phe Ala Ala Ala Ser Ala Val Ser Gly Arg Ser Phe Glu
225                 230                 235                 240 ttt caa ggc ctt ggc aca gac agc atc caa ggc gac acg tca ttc ttc     768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca ccc aac tcg     816
Asn Val Leu Gly Arg Leu Gly Ala Glu Val His Trp Ala Pro Asn Ser
            260                 265                 270 gtc acc ata cgg gga ccg gaa agg ctg aac ggc gac att gaa gtg gat     864
Val Thr Ile Arg Gly Pro Glu Arg Leu Asn Gly Asp Ile Glu Val Asp
        275                 280                 285 atg ggc gag att tcg gac acc ttc atg aca ctc gcg gcg att gcc cct     912
Met Gly Glu Ile Ser Asp Thr Phe Met Thr Leu Ala Ala Ile Ala Pro
    290                 295                 300 ttg gcc gat gga ccc atc acg ata acc aac att ggt cat gca cgg ttg     960
Leu Ala Asp Gly Pro Ile Thr Ile Thr Asn Ile Gly His Ala Arg Leu
305                 310                 315                 320
```

```
aag gaa tcc gac cgc atc tca gcg atg gaa acc aac ctg cgc acg ctc      1008
Lys Glu Ser Asp Arg Ile Ser Ala Met Glu Thr Asn Leu Arg Thr Leu
                325                 330                 335 ggt gta caa acc gac gtc gga cac gac tgg atg aga atc tac ccc tct      1056
Gly Val Gln Thr Asp Val Gly His Asp Trp Met Arg Ile Tyr Pro Ser
            340                 345                 350 acc ccg cac ggc ggt aga gtg aat tgc cac cgg gac cac agg atc gct      1104
Thr Pro His Gly Gly Arg Val Asn Cys His Arg Asp His Arg Ile Ala
        355                 360                 365 atg gcg ttt tca atc ctg gga ctg aga gtg gac ggg att acc ctc gac      1152
Met Ala Phe Ser Ile Leu Gly Leu Arg Val Asp Gly Ile Thr Leu Asp
    370                 375                 380 gac cct caa tgc gtc ggg aag acc ttt cct ggc ttc ttc gac tac ctt      1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag              1242
Gly Arg Leu Phe Pro Glu Lys Ala Leu Thr Leu Pro Gly
                405                 410

<210> SEQ ID NO 11
<211> LENGTH: 413
<212> TYPE: PRT
<213> ORGANISM: Artificial Sequence
<220> FEATURE:
<223> OTHER INFORMATION: GRG23(ACE2)

<400> SEQUENCE: 11

Met Glu Thr Asp Arg Leu Val Ile Pro Gly Ser Lys Ser Ile Thr Asn
1               5                   10                  15

Arg Ala Leu Leu Leu Ala Ala Ala Lys Gly Thr Ser Val Leu Val
            20                  25                  30

Arg Pro Leu Val Ser Ala Asp Thr Ser Ala Phe Lys Thr Ala Ile Gln
        35                  40                  45

Ala Leu Gly Ala Asn Val Ser Ala Asp Gly Asp Asn Trp Val Val Glu
    50                  55                  60

Gly Leu Gly Gln Ala Pro His Leu Asp Ala Asp Ile Trp Cys Glu Asp
65                  70                  75                  80

Ala Gly Thr Val Ala Arg Phe Leu Pro Pro Phe Val Ala Ala Gly Gln
                85                  90                  95

Gly Lys Phe Thr Val Asp Gly Ser Glu Gln Leu Arg Arg Pro Leu
            100                 105                 110

Arg Pro Leu Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Leu Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ala Ser Ala Val Ser Gly Arg Ser Phe Glu
225                 230                 235                 240

Phe Gln Gly Leu Gly Thr Asp Ser Ile Gln Gly Asp Thr Ser Phe Phe
```

```
                245                 250                 255
Asn Val Leu Gly Arg Leu Gly Ala Glu Val His Trp Ala Pro Asn Ser
            260                 265                 270

Val Thr Ile Arg Gly Pro Glu Arg Leu Asn Gly Asp Ile Glu Val Asp
            275                 280                 285

Met Gly Glu Ile Ser Asp Thr Phe Met Thr Leu Ala Ala Ile Ala Pro
            290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Thr Asn Leu Arg Thr Leu
                325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
            355                 360                 365

Met Ala Phe Ser Ile Leu Gly Leu Arg Val Asp Gly Ile Thr Leu Asp
            370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410

<210> SEQ ID NO 12
<211> LENGTH: 1242
<212> TYPE: DNA
<213> ORGANISM: Artificial Sequence
<220> FEATURE:
<223> OTHER INFORMATION: grg51.4
<221> NAME/KEY: CDS
<222> LOCATION: (1)...(1242)

<400> SEQUENCE: 12 atg gaa act gat cga cta gtg atc cca gga tcg aaa agc atc acc aac      48
Met Glu Thr Asp Arg Leu Val Ile Pro Gly Ser Lys Ser Ile Thr Asn
 1               5                  10                  15 cgg gct ttg ctt ttg gct gcc gca gcg aag ggc acg tcg gtc ctg gtg      96
Arg Ala Leu Leu Leu Ala Ala Ala Lys Gly Thr Ser Val Leu Val
            20                  25                  30 aga cca ttg gtc agc gcc gat acc tca gca ttc aaa act gca att cag     144
Arg Pro Leu Val Ser Ala Asp Thr Ser Ala Phe Lys Thr Ala Ile Gln
        35                  40                  45 gcc ctc ggt gcc aac gtc tca gcg gac ggt gat gat tgg gtc gtt gaa     192
Ala Leu Gly Ala Asn Val Ser Ala Asp Gly Asp Asp Trp Val Val Glu
    50                  55                  60 ggc ctg ggc cag gca ccc aac ctc gac gcc gac atc tgg tgc gag gat     240
Gly Leu Gly Gln Ala Pro Asn Leu Asp Ala Asp Ile Trp Cys Glu Asp
65                  70                  75                  80 gcc ggt acc gtg gcc cgg ttc ctc cct cca ttc gtc gcc gca gga cag     288
Ala Gly Thr Val Ala Arg Phe Leu Pro Pro Phe Val Ala Ala Gly Gln
                85                  90                  95 ggg aag ttc acc gtc gac gga agc gag cag ctg cgg cgg cgc ccg ctt     336
Gly Lys Phe Thr Val Asp Gly Ser Glu Gln Leu Arg Arg Arg Pro Leu
            100                 105                 110 cgg ccc gtg gtc gac ggc atc cgc cac ctg ggc gcc cgc gtc tcc tcc     384
Arg Pro Val Val Asp Gly Ile Arg His Leu Gly Ala Arg Val Ser Ser
        115                 120                 125 gag cag ctg ccc cta acg att gaa gcg agc ggg ctg gca ggc ggg gag     432
Glu Gln Leu Pro Leu Thr Ile Glu Ala Ser Gly Leu Ala Gly Gly Glu
    130                 135                 140
```

```
tac gaa att gaa gcc cat cag agc agc cag ttc gcc tcc ggt ctg atc      480
Tyr Glu Ile Glu Ala His Gln Ser Ser Gln Phe Ala Ser Gly Leu Ile
145                 150                 155                 160 atg gcc gcc ccg tac gcg cga caa ggc ctg cgt gtt cgg ata cca aat      528
Met Ala Ala Pro Tyr Ala Arg Gln Gly Leu Arg Val Arg Ile Pro Asn
                165                 170                 175 ccc gtg agc cag ccc tac ctc acg atg aca ctg cgg atg atg agg gac      576
Pro Val Ser Gln Pro Tyr Leu Thr Met Thr Leu Arg Met Met Arg Asp
            180                 185                 190 ttc ggc att gag acc agc acc gac gga gcg acc gtc agc gtt cct ccc      624
Phe Gly Ile Glu Thr Ser Thr Asp Gly Ala Thr Val Ser Val Pro Pro
        195                 200                 205 ggg cgc tac aca gcg cgg cgg tat gag att gaa ccg gac gcg tca act      672
Gly Arg Tyr Thr Ala Arg Arg Tyr Glu Ile Glu Pro Asp Ala Ser Thr
    210                 215                 220 gcg tcg tac ttc gcc gcc gct tcc gcc gtc tct ggc cgg cgc ttc gaa      720
Ala Ser Tyr Phe Ala Ala Ala Ser Ala Val Ser Gly Arg Arg Phe Glu
225                 230                 235                 240 ttc cag ggc ctt ggc aca gac agc atc caa ggc gac acg tca ttc ttc      768
Phe Gln Gly Leu Gly Thr Asp Ser Ile Gln Gly Asp Thr Ser Phe Phe
                245                 250                 255 aat gta ctt ggg cgg ctc ggc gca gag gtc cac tgg gca tcc aac tcg      816
Asn Val Leu Gly Arg Leu Gly Ala Glu Val His Trp Ala Ser Asn Ser
            260                 265                 270 gtc acc ata cgc gga ccg gaa agg ctg acc ggc gac att gaa gtg gat      864
Val Thr Ile Arg Gly Pro Glu Arg Leu Thr Gly Asp Ile Glu Val Asp
        275                 280                 285 atg ggc gag ata tcg gac acc ttc atg aca ctg gcg gcg att gcc cct      912
Met Gly Glu Ile Ser Asp Thr Phe Met Thr Leu Ala Ala Ile Ala Pro
    290                 295                 300 cta gcc gat gga ccc atc acg ata aca aac att ggc cat gca cgg ttg      960
Leu Ala Asp Gly Pro Ile Thr Ile Thr Asn Ile Gly His Ala Arg Leu
305                 310                 315                 320 aag gaa tcc gac cgc atc tcg gcg atg gaa agc aac ctt cga acg ctc     1008
Lys Glu Ser Asp Arg Ile Ser Ala Met Glu Ser Asn Leu Arg Thr Leu
                325                 330                 335 ggt gta caa acc gac gtc gga cac gac tgg atg cga atc tac ccc tct     1056
Gly Val Gln Thr Asp Val Gly His Asp Trp Met Arg Ile Tyr Pro Ser
            340                 345                 350 acc ccg cac ggc ggc aga gtc aat tgc cac cgg gac cac agg atc gcc     1104
Thr Pro His Gly Gly Arg Val Asn Cys His Arg Asp His Arg Ile Ala
        355                 360                 365 atg gcg ttt tca atc ctg gga ctg cga gtg gac ggg att acc ctc gac     1152
Met Ala Phe Ser Ile Leu Gly Leu Arg Val Asp Gly Ile Thr Leu Asp
    370                 375                 380 gac cct caa tgt gtc ggg aag acc ttt cct ggc ttc ttc gac tac ctt     1200
Asp Pro Gln Cys Val Gly Lys Thr Phe Pro Gly Phe Phe Asp Tyr Leu
385                 390                 395                 400 gga cgc ctt ttc ccg gaa aag gcg ctt acg ctc ccc ggc tag             1242
Gly Arg Leu Phe Pro Glu Lys Ala Leu Thr Leu Pro Gly
                405                 410

<210> SEQ ID NO 13
<211> LENGTH: 413
<212> TYPE: PRT
<213> ORGANISM: Artificial Sequence
<220> FEATURE:
<223> OTHER INFORMATION: GRG51.4

<400> SEQUENCE: 13

Met Glu Thr Asp Arg Leu Val Ile Pro Gly Ser Lys Ser Ile Thr Asn
1               5                   10                  15
```

```
Arg Ala Leu Leu Leu Ala Ala Ala Lys Gly Thr Ser Val Leu Val
         20                  25                  30

Arg Pro Leu Val Ser Ala Asp Thr Ser Ala Phe Lys Thr Ala Ile Gln
             35                  40                  45

Ala Leu Gly Ala Asn Val Ser Ala Asp Gly Asp Trp Val Val Glu
 50                  55                  60

Gly Leu Gly Gln Ala Pro Asn Leu Asp Ala Asp Ile Trp Cys Glu Asp
 65                  70                  75                  80

Ala Gly Thr Val Ala Arg Phe Leu Pro Pro Phe Val Ala Gly Gln
             85                  90                  95

Gly Lys Phe Thr Val Asp Gly Ser Glu Gln Leu Arg Arg Pro Leu
            100                 105                 110

Arg Pro Val Val Asp Gly Ile Arg His Leu Gly Ala Arg Val Ser Ser
            115                 120                 125

Glu Gln Leu Pro Leu Thr Ile Glu Ala Ser Gly Leu Ala Gly Gly Glu
130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Ile Glu Thr Ser Thr Asp Gly Ala Thr Val Ser Val Pro Pro
            195                 200                 205

Gly Arg Tyr Thr Ala Arg Arg Tyr Glu Ile Glu Pro Asp Ala Ser Thr
210                 215                 220

Ala Ser Tyr Phe Ala Ala Ser Ala Val Ser Gly Arg Phe Glu
225                 230                 235                 240

Phe Gln Gly Leu Gly Thr Asp Ser Ile Gln Gly Asp Thr Ser Phe Phe
            245                 250                 255

Asn Val Leu Gly Arg Leu Gly Ala Glu Val His Trp Ala Ser Asn Ser
            260                 265                 270

Val Thr Ile Arg Gly Pro Glu Arg Leu Thr Gly Asp Ile Glu Val Asp
            275                 280                 285

Met Gly Glu Ile Ser Asp Thr Phe Met Thr Leu Ala Ala Ile Ala Pro
290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Ser Asn Leu Arg Thr Leu
                325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
            355                 360                 365

Met Ala Phe Ser Ile Leu Gly Leu Arg Val Asp Gly Ile Thr Leu Asp
370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410
```

<210> SEQ ID NO 14
<211> LENGTH: 1242
<212> TYPE: DNA

<213> ORGANISM: Artificial Sequence
<220> FEATURE:
<223> OTHER INFORMATION: grg23(ace3)
<221> NAME/KEY: CDS
<222> LOCATION: (1)...(1242)

<400> SEQUENCE: 14

```
atg gaa act gat cgc ctt gtg atc cca gga tcg aaa agc atc acc aac        48
Met Glu Thr Asp Arg Leu Val Ile Pro Gly Ser Lys Ser Ile Thr Asn
1               5                   10                  15 cgg gct ttg ctt ttg gct gcc gca gcg aag ggc acg tcg gtc ctg gtg        96
Arg Ala Leu Leu Leu Ala Ala Ala Ala Lys Gly Thr Ser Val Leu Val
            20                  25                  30 aga cca ttg gtc agc gcc gat acc tca gca ttc aaa act gca atc cag       144
Arg Pro Leu Val Ser Ala Asp Thr Ser Ala Phe Lys Thr Ala Ile Gln
        35                  40                  45 gcc ctc ggt gcc aac gtc tca gcc gac ggt gac gat tgg gtc gtt gaa       192
Ala Leu Gly Ala Asn Val Ser Ala Asp Gly Asp Asp Trp Val Val Glu
    50                  55                  60 ggc ctg ggt cag gca ccc aac ctc gac gcc gac atc tgg tgc gag gac       240
Gly Leu Gly Gln Ala Pro Asn Leu Asp Ala Asp Ile Trp Cys Glu Asp
65                  70                  75                  80 gca ggt act gtg gcc cgg ttc ctc cct cca ttc gta gcc gca ggt cag       288
Ala Gly Thr Val Ala Arg Phe Leu Pro Pro Phe Val Ala Ala Gly Gln
                85                  90                  95 ggg aag ttc acc gtc gac gga tca gag cag ctg cgg cgg cgc ccg ctt       336
Gly Lys Phe Thr Val Asp Gly Ser Glu Gln Leu Arg Arg Arg Pro Leu
            100                 105                 110 cgg ccc gtg gtc gac ggc atc cgc cac ctg ggc gcc cgc gtc tcc tcc       384
Arg Pro Val Val Asp Gly Ile Arg His Leu Gly Ala Arg Val Ser Ser
        115                 120                 125 gag cag ctg ccc ctt aca att gaa gcg agc ggg ctg gca ggc ggg gag       432
Glu Gln Leu Pro Leu Thr Ile Glu Ala Ser Gly Leu Ala Gly Gly Glu
    130                 135                 140 tac gaa att gaa gcc cat cag agc agc cag ttc gcc tcc ggc ctg atc       480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat       528
Met Ala Ala Pro Tyr Ala Arg Gln Gly Leu Arg Val Arg Ile Pro Asn
                165                 170                 175 ccc gtg tca cag ccc tac ctc acg atg aca ctg cgg atg atg agg gac       576
Pro Val Ser Gln Pro Tyr Leu Thr Met Thr Leu Arg Met Met Arg Asp
            180                 185                 190 ttc ggc att gag acc agc acc gac gga gcc acc gtc agc gtc cct cca       624
Phe Gly Ile Glu Thr Ser Thr Asp Gly Ala Thr Val Ser Val Pro Pro
        195                 200                 205 ggg cgc tac aca gcc cgg cgg tat gaa ata gaa ccg gat gcg tca act       672
Gly Arg Tyr Thr Ala Arg Arg Tyr Glu Ile Glu Pro Asp Ala Ser Thr
    210                 215                 220 gcg tcg tac ttc gcc gcc gct tcc gcc gtc tct ggc agg cgc ttc gaa       720
Ala Ser Tyr Phe Ala Ala Ala Ser Ala Val Ser Gly Arg Arg Phe Glu
225                 230                 235                 240 ttt caa ggc ctt ggc aca gac agc atc caa ggc gac acg tca ttc ttc       768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca tcc aac tcg       816
Asn Val Leu Gly Arg Leu Gly Ala Glu Val His Trp Ala Ser Asn Ser
            260                 265                 270 gtc acc ata cgt gga ccg gaa agg ctg acc ggc gac att gaa gtg gat       864
Val Thr Ile Arg Gly Pro Glu Arg Leu Thr Gly Asp Ile Glu Val Asp
        275                 280                 285
```

```
atg ggc gag att tcg gac acc ttc atg aca ctc gcg gcg att gcc cct      912
Met Gly Glu Ile Ser Asp Thr Phe Met Thr Leu Ala Ala Ile Ala Pro
290                 295                 300 ttg gcc gat gga ccc atc acg ata acc aac att ggt cat gca cgg ttg      960
Leu Ala Asp Gly Pro Ile Thr Ile Thr Asn Ile Gly His Ala Arg Leu
305                 310                 315                 320 aag gaa tcc gac cgc atc tca gcg atg gaa agc aac ctg cgc acg ctc     1008
Lys Glu Ser Asp Arg Ile Ser Ala Met Glu Ser Asn Leu Arg Thr Leu
            325                 330                 335 ggt gta caa acc gac gtc gga cac gac tgg atg aga atc tac ccc tct     1056
Gly Val Gln Thr Asp Val Gly His Asp Trp Met Arg Ile Tyr Pro Ser
        340                 345                 350 acc ccg cac ggc ggt aga gtg aat tgc cac cgg gac cac agg atc gct     1104
Thr Pro His Gly Gly Arg Val Asn Cys His Arg Asp His Arg Ile Ala
    355                 360                 365 atg gcg ttt tca atc ctg gga ctg aga gtg gac ggg att acc ctc gac     1152
Met Ala Phe Ser Ile Leu Gly Leu Arg Val Asp Gly Ile Thr Leu Asp
370                 375                 380 gac cct caa tgc gtc ggg aag acc ttt cct ggc ttc ttc gac tac ctt     1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag             1242
Gly Arg Leu Phe Pro Glu Lys Ala Leu Thr Leu Pro Gly
            405                 410
```

<210> SEQ ID NO 15
<211> LENGTH: 413
<212> TYPE: PRT
<213> ORGANISM: Artificial Sequence
<220> FEATURE:
<223> OTHER INFORMATION: GRG23(ACE3)

<400> SEQUENCE: 15

```
Met Glu Thr Asp Arg Leu Val Ile Pro Gly Ser Lys Ser Ile Thr Asn
1               5                   10                  15

Arg Ala Leu Leu Leu Ala Ala Ala Lys Gly Thr Ser Val Leu Val
            20                  25                  30

Arg Pro Leu Val Ser Ala Asp Thr Ser Ala Phe Lys Thr Ala Ile Gln
        35                  40                  45

Ala Leu Gly Ala Asn Val Ser Ala Asp Gly Asp Asp Trp Val Val Glu
    50                  55                  60

Gly Leu Gly Gln Ala Pro Asn Leu Asp Ala Asp Ile Trp Cys Glu Asp
65                  70                  75                  80

Ala Gly Thr Val Ala Arg Phe Leu Pro Pro Phe Val Ala Ala Gly Gln
                85                  90                  95

Gly Lys Phe Thr Val Asp Gly Ser Glu Gln Leu Arg Arg Arg Pro Leu
            100                 105                 110

Arg Pro Val Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Ile Glu Thr Ser Thr Asp Gly Ala Thr Val Ser Val Pro Pro
        195                 200                 205
```

```
Gly Arg Tyr Thr Ala Arg Arg Tyr Glu Ile Glu Pro Asp Ala Ser Thr
    210                 215                 220
Ala Ser Tyr Phe Ala Ala Ser Ala Val Ser Gly Arg Arg Phe Glu
225                 230                 235                 240
Phe Gln Gly Leu Gly Thr Asp Ser Ile Gln Gly Asp Thr Ser Phe Phe
                245                 250                 255
Asn Val Leu Gly Arg Leu Gly Ala Glu Val His Trp Ala Ser Asn Ser
                260                 265                 270
Val Thr Ile Arg Gly Pro Glu Arg Leu Thr Gly Asp Ile Glu Val Asp
            275                 280                 285
Met Gly Glu Ile Ser Asp Thr Phe Met Thr Leu Ala Ala Ile Ala Pro
        290                 295                 300
Leu Ala Asp Gly Pro Ile Thr Ile Thr Asn Ile Gly His Ala Arg Leu
305                 310                 315                 320
Lys Glu Ser Asp Arg Ile Ser Ala Met Glu Ser Asn Leu Arg Thr Leu
                325                 330                 335
Gly Val Gln Thr Asp Val Gly His Asp Trp Met Arg Ile Tyr Pro Ser
                340                 345                 350
Thr Pro His Gly Gly Arg Val Asn Cys His Arg Asp His Arg Ile Ala
            355                 360                 365
Met Ala Phe Ser Ile Leu Gly Leu Arg Val Asp Gly Ile Thr Leu Asp
        370                 375                 380
Asp Pro Gln Cys Val Gly Lys Thr Phe Pro Gly Phe Phe Asp Tyr Leu
385                 390                 395                 400
Gly Arg Leu Phe Pro Glu Lys Ala Leu Thr Leu Pro Gly
                405                 410

<210> SEQ ID NO 16
<211> LENGTH: 1242
<212> TYPE: DNA
<213> ORGANISM: Artificial Sequence
<220> FEATURE:
<223> OTHER INFORMATION: grg23(L5P2.J2)
<221> NAME/KEY: CDS
<222> LOCATION: (1)...(1242)

<400> SEQUENCE: 16 atg gaa act gat cgc ctt gtg atc cca gga tcg aaa agc atc acc aac      48
Met Glu Thr Asp Arg Leu Val Ile Pro Gly Ser Lys Ser Ile Thr Asn
1               5                   10                  15 cgg gct ttg ctt ttg gct gcc gca gcg aag ggc acg tcg gtc ctg gtg      96
Arg Ala Leu Leu Leu Ala Ala Ala Ala Lys Gly Thr Ser Val Leu Val
                20                  25                  30 aga cca ttg gtc agc gcc gat acc tca gca ttc aaa act gca atc cag     144
Arg Pro Leu Val Ser Ala Asp Thr Ser Ala Phe Lys Thr Ala Ile Gln
            35                  40                  45 acc ctc ggt gcc aac gtc tca gcc gac ggt gac aat tgg gtc gtt gaa     192
Thr Leu Gly Ala Asn Val Ser Ala Asp Gly Asp Asn Trp Val Val Glu
        50                  55                  60 ggc ctg ggt cag gca ccc cac ctc gac gcc gac atc tgg tgc gag gac     240
Gly Leu Gly Gln Ala Pro His Leu Asp Ala Asp Ile Trp Cys Glu Asp
65                  70                  75                  80 gca ggt act gtg gcc cgg ttc ctc cct cca ttc gta gcc gca ggt cag     288
Ala Gly Thr Val Ala Arg Phe Leu Pro Pro Phe Val Ala Ala Gly Gln
                85                  90                  95 ggg aag ttc acc ttc gac gga tca gag cag ctg cgg cgg cgc ccg ctt     336
Gly Lys Phe Thr Phe Asp Gly Ser Glu Gln Leu Arg Arg Arg Pro Leu
                100                 105                 110
```

```
cgg ccc ctg gtc gac ggc atc cgc cac ctg ggc gcc cgc gtc tcc tcc      384
Arg Pro Leu Val Asp Gly Ile Arg His Leu Gly Ala Arg Val Ser Ser
        115                 120                 125 gag cag ctg ccc ctt aca att gaa gcg agt ggg ctg gca ggc ggg gag      432
Glu Gln Leu Pro Leu Thr Ile Glu Ala Ser Gly Leu Ala Gly Gly Glu
    130                 135                 140 tac gaa att gaa gcc cat cag agc agc cag ttc gcc tcc ggc ctg atc      480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat      528
Met Ala Ala Pro Tyr Ala Arg Gln Gly Leu Arg Val Arg Ile Pro Asn
                165                 170                 175 ccc gtg tca cag ccc tac ctc acg atg aca ctg cgg atg atg agg gac      576
Pro Val Ser Gln Pro Tyr Leu Thr Met Thr Leu Arg Met Met Arg Asp
            180                 185                 190 ttc ggc ctt gag acc agc acc gac gga gcc acc gtc agc gtc cct cca      624
Phe Gly Leu Glu Thr Ser Thr Asp Gly Ala Thr Val Ser Val Pro Pro
        195                 200                 205 ggg cgc tac aca tcc cgg cgg tat gaa ata gaa ccg gat gcg tca act      672
Gly Arg Tyr Thr Ser Arg Arg Tyr Glu Ile Glu Pro Asp Ala Ser Thr
    210                 215                 220 gcg tcg tac ttc gcc gcc gct tcc gcc gtc tct ggc agg agc ttc gaa      720
Ala Ser Tyr Phe Ala Ala Ala Ser Ala Val Ser Gly Arg Ser Phe Glu
225                 230                 235                 240 ttt caa ggc ctt ggc aca gac agc atc caa ggc gac acg tca ttc ttc      768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca ccc aac tcg      816
Asn Val Leu Gly Arg Leu Gly Ala Glu Val His Trp Ala Pro Asn Ser
            260                 265                 270 gtc acc ata act gga ccg gaa agg ctg aac ggc aac att gaa gtg gat      864
Val Thr Ile Thr Gly Pro Glu Arg Leu Asn Gly Asn Ile Glu Val Asp
        275                 280                 285 atg ggc gag att tcg gac acc ttc atg aca ctc gcg gcg att gcc cct      912
Met Gly Glu Ile Ser Asp Thr Phe Met Thr Leu Ala Ala Ile Ala Pro
    290                 295                 300 ttg gcc gat gga ccc atc acg ata acc aac att ggt cat gca cgg ttg      960
Leu Ala Asp Gly Pro Ile Thr Ile Thr Asn Ile Gly His Ala Arg Leu
305                 310                 315                 320 aag gaa tcc gac cgc atc tca gcg atg gaa acc aac ctg cgc acg ctc     1008
Lys Glu Ser Asp Arg Ile Ser Ala Met Glu Thr Asn Leu Arg Thr Leu
                325                 330                 335 ggt gta caa acc gac gtc gga cac gac tgg atg aga atc tac ccc tct     1056
Gly Val Gln Thr Asp Val Gly His Asp Trp Met Arg Ile Tyr Pro Ser
            340                 345                 350 acc ccg cac ggc ggt aga gtg aat tgc cac cgg gac cac agg atc gct     1104
Thr Pro His Gly Gly Arg Val Asn Cys His Arg Asp His Arg Ile Ala
        355                 360                 365 atg gcg ttt tca atc ctg gga ctg aga gtg gac ggg att acc ctc gac     1152
Met Ala Phe Ser Ile Leu Gly Leu Arg Val Asp Gly Ile Thr Leu Asp
    370                 375                 380 gac cct caa tgc gtc ggg aag acc ttt cct ggc ttc ttc gac tac ctt     1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag              1242
Gly Arg Leu Phe Pro Glu Lys Ala Leu Thr Leu Pro Gly
                405                 410

<210> SEQ ID NO 17
<211> LENGTH: 413
<212> TYPE: PRT
```

<213> ORGANISM: Artificial Sequence
<220> FEATURE:
<223> OTHER INFORMATION: GRG23(L5P2.J2)

<400> SEQUENCE: 17

```
Met Glu Thr Asp Arg Leu Val Ile Pro Gly Ser Lys Ser Ile Thr Asn
 1               5                  10                  15

Arg Ala Leu Leu Leu Ala Ala Ala Lys Gly Thr Ser Val Leu Val
            20                  25                  30

Arg Pro Leu Val Ser Ala Asp Thr Ser Ala Phe Lys Thr Ala Ile Gln
            35                  40                  45

Thr Leu Gly Ala Asn Val Ser Ala Asp Gly Asp Asn Trp Val Val Glu
50                  55                  60

Gly Leu Gly Gln Ala Pro His Leu Asp Ala Asp Ile Trp Cys Glu Asp
65                  70                  75                  80

Ala Gly Thr Val Ala Arg Phe Leu Pro Pro Phe Val Ala Ala Gly Gln
                85                  90                  95

Gly Lys Phe Thr Phe Asp Gly Ser Glu Gln Leu Arg Arg Pro Leu
            100                 105                 110

Arg Pro Leu Val Asp Gly Ile Arg His Leu Gly Ala Arg Val Ser Ser
            115                 120                 125

Glu Gln Leu Pro Leu Thr Ile Glu Ala Ser Gly Leu Ala Gly Gly Glu
130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Leu Glu Thr Ser Thr Asp Gly Ala Thr Val Ser Val Pro Pro
            195                 200                 205

Gly Arg Tyr Thr Ser Arg Arg Tyr Glu Ile Glu Pro Asp Ala Ser Thr
210                 215                 220

Ala Ser Tyr Phe Ala Ala Ser Ala Val Ser Gly Arg Ser Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Pro Asn Ser
            260                 265                 270

Val Thr Ile Thr Gly Pro Glu Arg Leu Asn Gly Asn Ile Glu Val Asp
            275                 280                 285

Met Gly Glu Ile Ser Asp Thr Phe Met Thr Leu Ala Ala Ile Ala Pro
290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Thr Asn Leu Arg Thr Leu
                325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
            355                 360                 365

Met Ala Phe Ser Ile Leu Gly Leu Arg Val Asp Gly Ile Thr Leu Asp
370                 375                 380

Asp Pro Gln Cys Val Gly Lys Thr Phe Pro Gly Phe Phe Asp Tyr Leu
385                 390                 395                 400
```

```
Gly Arg Leu Phe Pro Glu Lys Ala Leu Thr Leu Pro Gly
            405                 410

<210> SEQ ID NO 18
<211> LENGTH: 1242
<212> TYPE: DNA
<213> ORGANISM: Artificial Sequence
<220> FEATURE:
<223> OTHER INFORMATION: grg23(ace4)
<221> NAME/KEY: CDS
<222> LOCATION: (1)...(1242)

<400> SEQUENCE: 18 atg gaa act gat cgc ctt gtg atc cca gga tcg aaa agc atc acc aac      48
Met Glu Thr Asp Arg Leu Val Ile Pro Gly Ser Lys Ser Ile Thr Asn
 1               5                  10                  15 cgg gct ttg ctt ttg gct gcc gca gcg aag ggc acg tcg gtc ctg gtg      96
Arg Ala Leu Leu Leu Ala Ala Ala Ala Lys Gly Thr Ser Val Leu Val
                20                  25                  30 aga cca ttg gtc agc gcc gat acc tca gca ttc aaa act gca atc cag     144
Arg Pro Leu Val Ser Ala Asp Thr Ser Ala Phe Lys Thr Ala Ile Gln
            35                  40                  45 gcc ctc ggt gcc aac gtc tca gcc gac ggt gac gat tgg gtc gtt gaa     192
Ala Leu Gly Ala Asn Val Ser Ala Asp Gly Asp Asp Trp Val Val Glu
        50                  55                  60 ggc ctg ggt cag gca ccc aac ctc gac gcc gac atc tgg tgc gag gac     240
Gly Leu Gly Gln Ala Pro Asn Leu Asp Ala Asp Ile Trp Cys Glu Asp
 65                  70                  75                  80 gca ggt act gtg gcc cgg ttc ctc cct cca ttc gta gcc gca ggt cag     288
Ala Gly Thr Val Ala Arg Phe Leu Pro Pro Phe Val Ala Ala Gly Gln
                 85                  90                  95 ggg aag ttc acc ttc gac gga tca gag cag ctg cgg cgg cgc ccg ctt     336
Gly Lys Phe Thr Phe Asp Gly Ser Glu Gln Leu Arg Arg Arg Pro Leu
                100                 105                 110 cgg ccc gtg gtc gac ggc atc cgc cac ctg ggc gcc cgc gtc tcc tcc     384
Arg Pro Val Val Asp Gly Ile Arg His Leu Gly Ala Arg Val Ser Ser
            115                 120                 125 gag cag ctg ccc ctt aca att gaa gcg agc ggg ctg gca ggc ggg gag     432
Glu Gln Leu Pro Leu Thr Ile Glu Ala Ser Gly Leu Ala Gly Gly Glu
        130                 135                 140 tac gaa att gaa gcc cat cag agc agc cag ttc gcc tcc ggc ctg atc     480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat     528
Met Ala Ala Pro Tyr Ala Arg Gln Gly Leu Arg Val Arg Ile Pro Asn
                165                 170                 175 ccc gtg tca cag ccc tac ctc acg atg aca ctg cgg atg atg agg gac     576
Pro Val Ser Gln Pro Tyr Leu Thr Met Thr Leu Arg Met Met Arg Asp
                180                 185                 190 ttc ggc att gag acc agc acc gac gga gcc acc gtc agc gtc cct cca     624
Phe Gly Ile Glu Thr Ser Thr Asp Gly Ala Thr Val Ser Val Pro Pro
            195                 200                 205 ggg cgc tac aca gcc cgg cgg tat gaa ata gaa ccg gat gcg tca act     672
Gly Arg Tyr Thr Ala Arg Arg Tyr Glu Ile Glu Pro Asp Ala Ser Thr
        210                 215                 220 gcg tcg tac ttc gcc gcc gct tcc gcc gtc tct ggc agg cgc ttc gaa     720
Ala Ser Tyr Phe Ala Ala Ala Ser Ala Val Ser Gly Arg Arg Phe Glu
225                 230                 235                 240 ttt caa ggc ctt ggc aca gac agc atc caa ggc gac acg tca ttc ttc     768
Phe Gln Gly Leu Gly Thr Asp Ser Ile Gln Gly Asp Thr Ser Phe Phe
                245                 250                 255
```

```
aat gta ctt ggg cgg ctc ggt gcg gag gtc cac tgg gca tcc aac tcg     816
Asn Val Leu Gly Arg Leu Gly Ala Glu Val His Trp Ala Ser Asn Ser
        260                 265                 270 gtc acc ata cgg gga ccg gaa agg ctg acc ggc gac att gaa gtg gat     864
Val Thr Ile Arg Gly Pro Glu Arg Leu Thr Gly Asp Ile Glu Val Asp
    275                 280                 285 atg ggc gag att tcg gac acc ttc atg aca ctc gcg gcg att gcc cct     912
Met Gly Glu Ile Ser Asp Thr Phe Met Thr Leu Ala Ala Ile Ala Pro
290                 295                 300 ttg gcc gat gga ccc atc acg ata acc aac att ggt cat gca cgg ttg     960
Leu Ala Asp Gly Pro Ile Thr Ile Thr Asn Ile Gly His Ala Arg Leu
305                 310                 315                 320 aag gaa tcc gac cgc atc tca gcg atg gaa agc aac ctg cgc acg ctc    1008
Lys Glu Ser Asp Arg Ile Ser Ala Met Glu Ser Asn Leu Arg Thr Leu
                325                 330                 335 ggt gta caa acc gac gtc gga cac gac tgg atg aga atc tac ccc tct    1056
Gly Val Gln Thr Asp Val Gly His Asp Trp Met Arg Ile Tyr Pro Ser
            340                 345                 350 acc ccg cac ggc ggt aga gtg aat tgc cac cgg gac cac agg atc gct    1104
Thr Pro His Gly Gly Arg Val Asn Cys His Arg Asp His Arg Ile Ala
        355                 360                 365 atg gcg ttt tca atc ctg gga ctg aga gtg gac ggg att acc ctc gac    1152
Met Ala Phe Ser Ile Leu Gly Leu Arg Val Asp Gly Ile Thr Leu Asp
370                 375                 380 gac cct caa tgc gtc ggg aag acc ttt cct ggc ttc ttc gac tac ctt    1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag            1242
Gly Arg Leu Phe Pro Glu Lys Ala Leu Thr Leu Pro Gly
                405                 410

<210> SEQ ID NO 19
<211> LENGTH: 413
<212> TYPE: PRT
<213> ORGANISM: Artificial Sequence
<220> FEATURE:
<223> OTHER INFORMATION: GRG23(ACE4)

<400> SEQUENCE: 19

Met Glu Thr Asp Arg Leu Val Ile Pro Gly Ser Lys Ser Ile Thr Asn
1               5                   10                  15

Arg Ala Leu Leu Leu Ala Ala Ala Lys Gly Thr Ser Val Leu Val
            20                  25                  30

Arg Pro Leu Val Ser Ala Asp Thr Ser Ala Phe Lys Thr Ala Ile Gln
        35                  40                  45

Ala Leu Gly Ala Asn Val Ser Ala Asp Gly Asp Asp Trp Val Val Glu
    50                  55                  60

Gly Leu Gly Gln Ala Pro Asn Leu Asp Ala Asp Ile Trp Cys Glu Asp
65                  70                  75                  80

Ala Gly Thr Val Ala Arg Phe Leu Pro Pro Phe Val Ala Ala Gly Gln
                85                  90                  95

Gly Lys Phe Thr Phe Asp Gly Ser Glu Gln Leu Arg Arg Arg Pro Leu
            100                 105                 110

Arg Pro Val Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160
```

```
Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Ile Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ala Ser Ala Val Ser Gly Arg Arg Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Ser Asn Ser
            260                 265                 270

Val Thr Ile Arg Gly Pro Glu Arg Leu Thr Gly Asp Ile Glu Val Asp
        275                 280                 285

Met Gly Glu Ile Ser Asp Thr Phe Met Thr Leu Ala Ala Ile Ala Pro
    290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Ser Asn Leu Arg Thr Leu
                325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
        355                 360                 365

Met Ala Phe Ser Ile Leu Gly Leu Arg Val Asp Gly Ile Thr Leu Asp
    370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410
```

<210> SEQ ID NO 20
<211> LENGTH: 1244
<212> TYPE: DNA
<213> ORGANISM: Artificial Sequence
<220> FEATURE:
<223> OTHER INFORMATION: grg23(L3P1.B20)
<221> NAME/KEY: CDS
<222> LOCATION: (1)...(1242)

<400> SEQUENCE: 20

```
atg gaa act gat cgc ctt gtg atc cca gga tcg aaa agc atc acc aac    48
Met Glu Thr Asp Arg Leu Val Ile Pro Gly Ser Lys Ser Ile Thr Asn
1               5                   10                  15 cgg gct ttg ctt ttg gct gcc gca gcg aag ggc acg tcg gtc ctg gtg    96
Arg Ala Leu Leu Leu Ala Ala Ala Ala Lys Gly Thr Ser Val Leu Val
                20                  25                  30 aga cca ttg gtc agc gcc gat acc tca gca ttc aaa act gca atc cag   144
Arg Pro Leu Val Ser Ala Asp Thr Ser Ala Phe Lys Thr Ala Ile Gln
            35                  40                  45 gcc ctc ggt gcc aac gtc tca gcc gac ggt gac aat tgg gtc gtt gaa   192
Ala Leu Gly Ala Asn Val Ser Ala Asp Gly Asp Asn Trp Val Val Glu
        50                  55                  60 ggc ctg ggt cag gca ccc cac ctc gac gcc gac atc tgg tgc gag gac   240
Gly Leu Gly Gln Ala Pro His Leu Asp Ala Asp Ile Trp Cys Glu Asp
65                  70                  75                  80
```

```
gca ggt act gtg gcc cgg ttc ctc cct cca ttc gta gcc gca ggt cag        288
Ala Gly Thr Val Ala Arg Phe Leu Pro Pro Phe Val Ala Ala Gly Gln
                85                  90                  95 ggg aag ttc acc gtc gac gga tca gag cag ttg cgg cgc cgc ccg ctt        336
Gly Lys Phe Thr Val Asp Gly Ser Glu Gln Leu Arg Arg Arg Pro Leu
            100                 105                 110 cgg ccc ctg gtt gac ggc atc cgc cac ctg ggc gcc cgc gtc tcc tcc        384
Arg Pro Leu Val Asp Gly Ile Arg His Leu Gly Ala Arg Val Ser Ser
        115                 120                 125 gag cag ctg ccc ctt aca att gaa gcg agc ggg ctg gca ggc ggg gag        432
Glu Gln Leu Pro Leu Thr Ile Glu Ala Ser Gly Leu Ala Gly Gly Glu
    130                 135                 140 tac gaa att gaa gcc cat cag agc agc cag ttc gcc tcc ggc ctg atc        480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat        528
Met Ala Ala Pro Tyr Ala Arg Gln Gly Leu Arg Val Arg Ile Pro Asn
                165                 170                 175 ccc gtg tca cag ccc tac ctc acg atg aca ctg cgg atg atg agg gac        576
Pro Val Ser Gln Pro Tyr Leu Thr Met Thr Leu Arg Met Met Arg Asp
            180                 185                 190 ttc ggc ctt gag acc agc acc gac gga gcc acc gtc agc atc cct cca        624
Phe Gly Leu Glu Thr Ser Thr Asp Gly Ala Thr Val Ser Ile Pro Pro
        195                 200                 205 ggg cgc tac aca gcc cgg cgg tat gaa ata gaa ccg gat gcg tca act        672
Gly Arg Tyr Thr Ala Arg Arg Tyr Glu Ile Glu Pro Asp Ala Ser Thr
    210                 215                 220 gcg tcg tac ttc gcc gcc gct tcc gcc gtc tct ggc agg agc ttc gaa        720
Ala Ser Tyr Phe Ala Ala Ala Ser Ala Val Ser Gly Arg Ser Phe Glu
225                 230                 235                 240 ttt caa ggc ctt ggc aca gac agc atc caa ggc gac acg tca ttc ttc        768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca ccc aac tcg        816
Asn Val Leu Gly Arg Leu Gly Ala Glu Val His Trp Ala Pro Asn Ser
            260                 265                 270 gtc acc ata tct gga ccg gaa agg ctg aac ggc gac att gaa gtg gat        864
Val Thr Ile Ser Gly Pro Glu Arg Leu Asn Gly Asp Ile Glu Val Asp
        275                 280                 285 atg ggc gag att tcg gac acc ttc atg aca ctc gcg gcg att gcc cct        912
Met Gly Glu Ile Ser Asp Thr Phe Met Thr Leu Ala Ala Ile Ala Pro
    290                 295                 300 ttg gcc gat gga ccc atc acg ata acc aac att ggt cat gca cgg ttg        960
Leu Ala Asp Gly Pro Ile Thr Ile Thr Asn Ile Gly His Ala Arg Leu
305                 310                 315                 320 aag gaa tcc gac cgc atc tca gcg atg gaa acc aac ctg cgc acg ctc       1008
Lys Glu Ser Asp Arg Ile Ser Ala Met Glu Thr Asn Leu Arg Thr Leu
                325                 330                 335 ggt gta caa acc gac gtc gga cac gac tgg atg aga atc tac ccc tct       1056
Gly Val Gln Thr Asp Val Gly His Asp Trp Met Arg Ile Tyr Pro Ser
            340                 345                 350 acc ccg cac ggc ggt aga gtg aat tgc cac cgg gac cac agg atc gct       1104
Thr Pro His Gly Gly Arg Val Asn Cys His Arg Asp His Arg Ile Ala
        355                 360                 365 atg gcg ttt tca atc ctg gga ctg aga gtg gac ggg att acc ctc gac       1152
Met Ala Phe Ser Ile Leu Gly Leu Arg Val Asp Gly Ile Thr Leu Asp
    370                 375                 380 gac cct caa tgc gtc ggg aag acc ttt cct ggc ttc ttc gac tac ctt       1200
Asp Pro Gln Cys Val Gly Lys Thr Phe Pro Gly Phe Phe Asp Tyr Leu
385                 390                 395                 400
```

```
gga cgc ctt ttc ccc gaa aag gcg ctt acg ctc ccc ggc tag        1242
Gly Arg Leu Phe Pro Glu Lys Ala Leu Thr Leu Pro Gly
            405                 410 gg                                                             1244
```

<210> SEQ ID NO 21
<211> LENGTH: 413
<212> TYPE: PRT
<213> ORGANISM: Artificial Sequence
<220> FEATURE:
<223> OTHER INFORMATION: GRG23(L3P1.B20)

<400> SEQUENCE: 21

```
Met Glu Thr Asp Arg Leu Val Ile Pro Gly Ser Lys Ser Ile Thr Asn
  1               5                  10                  15

Arg Ala Leu Leu Leu Ala Ala Ala Lys Gly Thr Ser Val Leu Val
             20                  25                  30

Arg Pro Leu Val Ser Ala Asp Thr Ser Ala Phe Lys Thr Ala Ile Gln
         35                  40                  45

Ala Leu Gly Ala Asn Val Ser Ala Asp Gly Asp Asn Trp Val Val Glu
     50                  55                  60

Gly Leu Gly Gln Ala Pro His Leu Asp Ala Asp Ile Trp Cys Glu Asp
 65                  70                  75                  80

Ala Gly Thr Val Ala Arg Phe Leu Pro Pro Phe Val Ala Gly Gln
             85                  90                  95

Gly Lys Phe Thr Val Asp Gly Ser Glu Gln Leu Arg Arg Pro Leu
            100                 105                 110

Arg Pro Leu Val Asp Gly Ile Arg His Leu Gly Ala Arg Val Ser Ser
            115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Leu Glu Thr Ser Thr Asp Gly Ala Thr Val Ser Ile Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ala Ser Ala Val Ser Gly Arg Ser Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Pro Asn Ser
            260                 265                 270

Val Thr Ile Ser Gly Pro Glu Arg Leu Asn Gly Asp Ile Glu Val Asp
        275                 280                 285

Met Gly Glu Ile Ser Asp Thr Phe Met Thr Leu Ala Ala Ile Ala Pro
    290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Thr Asn Leu Arg Thr Leu
                325                 330                 335

Gly Val Gln Thr Asp Val Gly His Asp Trp Met Arg Ile Tyr Pro Ser
```

```
                    340                 345                 350
Thr Pro His Gly Gly Arg Val Asn Cys His Arg Asp His Arg Ile Ala
        355                 360                 365

Met Ala Phe Ser Ile Leu Gly Leu Arg Val Asp Gly Ile Thr Leu Asp
    370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410

<210> SEQ ID NO 22
<211> LENGTH: 1244
<212> TYPE: DNA
<213> ORGANISM: Artificial Sequence
<220> FEATURE:
<223> OTHER INFORMATION: grg23(L3P1.B3)
<221> NAME/KEY: CDS
<222> LOCATION: (1)...(1242)

<400> SEQUENCE: 22 atg gaa act gat cgc ctt gtg atc cca gga tcg aaa agc atc acc aac      48
Met Glu Thr Asp Arg Leu Val Ile Pro Gly Ser Lys Ser Ile Thr Asn
1               5                   10                  15 cgg gct ttg ctt ttg gct gcc gca gcg aag ggc acg tcg gtc ctg gtg      96
Arg Ala Leu Leu Leu Ala Ala Ala Ala Lys Gly Thr Ser Val Leu Val
                20                  25                  30 aga cca ttg gtc agc gcc gat acc tca gca ttc aaa act gca atc cag     144
Arg Pro Leu Val Ser Ala Asp Thr Ser Ala Phe Lys Thr Ala Ile Gln
            35                  40                  45 gcc ctc ggt gcc aac gtc tca gcc gac ggt gac aat tgg gtc gtt gaa     192
Ala Leu Gly Ala Asn Val Ser Ala Asp Gly Asp Asn Trp Val Val Glu
        50                  55                  60 ggc ctg ggt cag gca ccc cac ctc gac gcc cac atc tgg tgc gag gac     240
Gly Leu Gly Gln Ala Pro His Leu Asp Ala His Ile Trp Cys Glu Asp
65                  70                  75                  80 gca ggt act gtg gcc cgg ttc ctc cct cca ttc gta gcc gca ggt cag     288
Ala Gly Thr Val Ala Arg Phe Leu Pro Pro Phe Val Ala Ala Gly Gln
                85                  90                  95 ggg aag ttc acc gtc gac gga tca gag cag ctg cgg cgg cgc ccg ctt     336
Gly Lys Phe Thr Val Asp Gly Ser Glu Gln Leu Arg Arg Arg Pro Leu
            100                 105                 110 cgg ccc ctg gtc gac ggc atc cgc cac ctg ggc gcc cgc gtc tcc tcc     384
Arg Pro Leu Val Asp Gly Ile Arg His Leu Gly Ala Arg Val Ser Ser
        115                 120                 125 gag cag ctg ccc ctt aca att gaa gcg agc ggg ctg gca ggc ggg gag     432
Glu Gln Leu Pro Leu Thr Ile Glu Ala Ser Gly Leu Ala Gly Gly Glu
    130                 135                 140 tac gaa att gaa gcc cat cag agc agc cag ttc gcc tcc ggc ctg atc     480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat     528
Met Ala Ala Pro Tyr Ala Arg Gln Gly Leu Arg Val Arg Ile Pro Asn
                165                 170                 175 ccc gtg tca cag ccc tac ctc acg atg aca ctg cgg atg atg agg gac     576
Pro Val Ser Gln Pro Tyr Leu Thr Met Thr Leu Arg Met Met Arg Asp
            180                 185                 190 ttc ggc ctt gag acc agc acc gac gga gcc acc gtc agc gtc cct cca     624
Phe Gly Leu Glu Thr Ser Thr Asp Gly Ala Thr Val Ser Val Pro Pro
        195                 200                 205 ggg cgc tac aca gcc cgg cgg tat aaa ata gaa ccg gat gcg tca act     672
Gly Arg Tyr Thr Ala Arg Arg Tyr Lys Ile Glu Pro Asp Ala Ser Thr
```

```
     210                 215                 220
gcg tcg tac ttc gcc gcc gct tcc gcc gtc tct ggc agg agc ttc gaa      720
Ala Ser Tyr Phe Ala Ala Ala Ser Ala Val Ser Gly Arg Ser Phe Glu
225                 230                 235                 240 ttt caa ggc ctt ggc aca gac agc atc caa ggc gac acg tca ttc ttc      768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca ccc aac tcg      816
Asn Val Leu Gly Arg Leu Gly Ala Glu Val His Trp Ala Pro Asn Ser
            260                 265                 270 gtc acc ata tct gga ccg gaa agg ctg aac ggc gac att gaa gtg gat      864
Val Thr Ile Ser Gly Pro Glu Arg Leu Asn Gly Asp Ile Glu Val Asp
        275                 280                 285 atg ggc gag att tcg gac acc ttc atg aca ctc gcg gcg att gcc cct      912
Met Gly Glu Ile Ser Asp Thr Phe Met Thr Leu Ala Ala Ile Ala Pro
290                 295                 300 ttg gcc gat gga ccc atc acg ata acc aac att ggt cat gca cgg ttg      960
Leu Ala Asp Gly Pro Ile Thr Ile Thr Asn Ile Gly His Ala Arg Leu
305                 310                 315                 320 aag gaa tcc gac cgc atc tca gcg atg gaa acc aac ctg cgc acg ctc     1008
Lys Glu Ser Asp Arg Ile Ser Ala Met Glu Thr Asn Leu Arg Thr Leu
                325                 330                 335 ggt gta caa acc gac gtc gga cac gac tgg atg aga atc tac ccc tct     1056
Gly Val Gln Thr Asp Val Gly His Asp Trp Met Arg Ile Tyr Pro Ser
            340                 345                 350 acc ccg cac ggc ggt aga gtg aat tgc cac cga gac cac agg atc gct     1104
Thr Pro His Gly Gly Arg Val Asn Cys His Arg Asp His Arg Ile Ala
        355                 360                 365 atg gcg ttt tca atc ctg gga ctg aga gtg gac ggg att acc ctc gac     1152
Met Ala Phe Ser Ile Leu Gly Leu Arg Val Asp Gly Ile Thr Leu Asp
370                 375                 380 gac cct caa tgc gtc ggg aag acc ttt cct ggc ttc ttc gac tac ctt     1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag             1242
Gly Arg Leu Phe Pro Glu Lys Ala Leu Thr Leu Pro Gly
                405                 410 gg                                                                  1244

<210> SEQ ID NO 23
<211> LENGTH: 413
<212> TYPE: PRT
<213> ORGANISM: Artificial Sequence
<220> FEATURE:
<223> OTHER INFORMATION: GRG23(L3P1.B3)

<400> SEQUENCE: 23

Met Glu Thr Asp Arg Leu Val Ile Pro Gly Ser Lys Ser Ile Thr Asn
1               5                   10                  15

Arg Ala Leu Leu Leu Ala Ala Ala Lys Gly Thr Ser Val Leu Val
            20                  25                  30

Arg Pro Leu Val Ser Ala Asp Thr Ser Ala Phe Lys Thr Ala Ile Gln
        35                  40                  45

Ala Leu Gly Ala Asn Val Ser Ala Asp Gly Asp Asn Trp Val Val Glu
    50                  55                  60

Gly Leu Gly Gln Ala Pro His Leu Asp Ala His Ile Trp Cys Glu Asp
65                  70                  75                  80

Ala Gly Thr Val Ala Arg Phe Leu Pro Pro Phe Val Ala Ala Gly Gln
                85                  90                  95
```

```
Gly Lys Phe Thr Val Asp Gly Ser Glu Gln Leu Arg Arg Pro Leu
            100                 105                 110
Arg Pro Leu Val Asp Gly Ile Arg His Leu Gly Ala Arg Val Ser Ser
        115                 120                 125
Glu Gln Leu Pro Leu Thr Ile Glu Ala Ser Gly Leu Ala Gly Gly Glu
    130                 135                 140
Tyr Glu Ile Glu Ala His Gln Ser Ser Gln Phe Ala Ser Gly Leu Ile
145                 150                 155                 160
Met Ala Ala Pro Tyr Ala Arg Gln Gly Leu Arg Val Arg Ile Pro Asn
                165                 170                 175
Pro Val Ser Gln Pro Tyr Leu Thr Met Thr Leu Arg Met Met Arg Asp
            180                 185                 190
Phe Gly Leu Glu Thr Ser Thr Asp Gly Ala Thr Val Ser Val Pro Pro
        195                 200                 205
Gly Arg Tyr Thr Ala Arg Arg Tyr Lys Ile Glu Pro Asp Ala Ser Thr
    210                 215                 220
Ala Ser Tyr Phe Ala Ala Ser Ala Val Ser Gly Arg Ser Phe Glu
225                 230                 235                 240
Phe Gln Gly Leu Gly Thr Asp Ser Ile Gln Gly Asp Thr Ser Phe Phe
                245                 250                 255
Asn Val Leu Gly Arg Leu Gly Ala Glu Val His Trp Ala Pro Asn Ser
            260                 265                 270
Val Thr Ile Ser Gly Pro Glu Arg Leu Asn Gly Asp Ile Glu Val Asp
        275                 280                 285
Met Gly Glu Ile Ser Asp Thr Phe Met Thr Leu Ala Ala Ile Ala Pro
    290                 295                 300
Leu Ala Asp Gly Pro Ile Thr Ile Thr Asn Ile Gly His Ala Arg Leu
305                 310                 315                 320
Lys Glu Ser Asp Arg Ile Ser Ala Met Glu Thr Asn Leu Arg Thr Leu
                325                 330                 335
Gly Val Gln Thr Asp Val Gly His Asp Trp Met Arg Ile Tyr Pro Ser
            340                 345                 350
Thr Pro His Gly Gly Arg Val Asn Cys His Arg Asp His Arg Ile Ala
        355                 360                 365
Met Ala Phe Ser Ile Leu Gly Leu Arg Val Asp Gly Ile Thr Leu Asp
    370                 375                 380
Asp Pro Gln Cys Val Gly Lys Thr Phe Pro Gly Phe Phe Asp Tyr Leu
385                 390                 395                 400
Gly Arg Leu Phe Pro Glu Lys Ala Leu Thr Leu Pro Gly
                405                 410

<210> SEQ ID NO 24
<211> LENGTH: 1244
<212> TYPE: DNA
<213> ORGANISM: Artificial Sequence
<220> FEATURE:
<223> OTHER INFORMATION: grg23(L3P1.F18)
<221> NAME/KEY: CDS
<222> LOCATION: (1)...(1242)

<400> SEQUENCE: 24 atg gaa act gat cgc ctt gtg atc cca gga tcg aaa agc atc acc aac    48
Met Glu Thr Asp Arg Leu Val Ile Pro Gly Ser Lys Ser Ile Thr Asn
 1               5                  10                  15 cgg gct ttg ctt ttg gct gcc gca gcg aag ggc acg tcg gtc ctg gtg    96
Arg Ala Leu Leu Leu Ala Ala Ala Ala Lys Gly Thr Ser Val Leu Val
            20                  25                  30
```

```
aga cca ttg gtc agc gcc gat acc tca gca ttc aaa act gca atc cag      144
Arg Pro Leu Val Ser Ala Asp Thr Ser Ala Phe Lys Thr Ala Ile Gln
         35                  40                  45 gcc ctc ggt gcc aac gtc tca gcc gac ggt gac aat tgg gtc gtt gaa      192
Ala Leu Gly Ala Asn Val Ser Ala Asp Gly Asp Asn Trp Val Val Glu
     50                  55                  60 ggc ctg ggt cag gca ccc cac ctc gac gcc gac atc tgg tgc gag gac      240
Gly Leu Gly Gln Ala Pro His Leu Asp Ala Asp Ile Trp Cys Glu Asp
 65                  70                  75                  80 gca ggt act gtg gcc cgg ttc ctc cct cca ttc gta gcc gca ggt cag      288
Ala Gly Thr Val Ala Arg Phe Leu Pro Pro Phe Val Ala Ala Gly Gln
                 85                  90                  95 ggg aag ttc acc gtc gac gga tca gag cag ctg cgg cgg cgc ccg ctt      336
Gly Lys Phe Thr Val Asp Gly Ser Glu Gln Leu Arg Arg Arg Pro Leu
            100                 105                 110 cgg ccc ctg gtc gac ggc atc cgc cac ctg ggc gcc cgc gtc tcc tcc      384
Arg Pro Leu Val Asp Gly Ile Arg His Leu Gly Ala Arg Val Ser Ser
        115                 120                 125 gag cag ctg ccc ctt aca att gaa gcg agc ggg ctg gca ggc ggg gag      432
Glu Gln Leu Pro Leu Thr Ile Glu Ala Ser Gly Leu Ala Gly Gly Glu
    130                 135                 140 tac gaa att gaa gcc cat cag agc agc cag ttc gcc tcc ggc ctg atc      480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat      528
Met Ala Ala Pro Tyr Ala Arg Gln Gly Leu Arg Val Arg Ile Pro Asn
                165                 170                 175 ccc gtg tca cag ccc tac ctc acg atg aca ctg cgg atg atg agg gac      576
Pro Val Ser Gln Pro Tyr Leu Thr Met Thr Leu Arg Met Met Arg Asp
            180                 185                 190 ttc ggc ctt gag acc agc acc gac gga gcc acc gtc agc gtc cct cca      624
Phe Gly Leu Glu Thr Ser Thr Asp Gly Ala Thr Val Ser Val Pro Pro
        195                 200                 205 ggg cgc tac aca gcc cgg cgg tat gaa ata gaa ccg gat gcg tca act      672
Gly Arg Tyr Thr Ala Arg Arg Tyr Glu Ile Glu Pro Asp Ala Ser Thr
    210                 215                 220 gcg tcg tac ttc gcc gcc gct tcc gcc gtc tct ggc agg agc ttc gaa      720
Ala Ser Tyr Phe Ala Ala Ala Ser Ala Val Ser Gly Arg Ser Phe Glu
225                 230                 235                 240 ttt caa ggc ctt ggc aca gac agc atc caa ggc gac acg tca ttc ttc      768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca ccc aac tcg      816
Asn Val Leu Gly Arg Leu Gly Ala Glu Val His Trp Ala Pro Asn Ser
            260                 265                 270 gtc atc ata tct gga ccg gaa agg ctg aac ggc gac att gaa gtg gat      864
Val Ile Ile Ser Gly Pro Glu Arg Leu Asn Gly Asp Ile Glu Val Asp
        275                 280                 285 atg ggc gag att tcg gac acc ttc atg aca ctc gcg gcg att gcc cct      912
Met Gly Glu Ile Ser Asp Thr Phe Met Thr Leu Ala Ala Ile Ala Pro
    290                 295                 300 ttg gcc gat gga ccc atc acg ata acc aac att ggt cat gca cgg ttg      960
Leu Ala Asp Gly Pro Ile Thr Ile Thr Asn Ile Gly His Ala Arg Leu
305                 310                 315                 320 aag gaa tcc gac cgc atc tca gcg atg gaa acc aac ctg cgc acg ctc     1008
Lys Glu Ser Asp Arg Ile Ser Ala Met Glu Thr Asn Leu Arg Thr Leu
                325                 330                 335 ggt gta caa acc gac gtc gga cac gac tgg atg aga atc tac ccc tct     1056
Gly Val Gln Thr Asp Val Gly His Asp Trp Met Arg Ile Tyr Pro Ser
            340                 345                 350
```

```
acc ccg cac ggc ggt aga gtg aat tgc cac cgg gac cac agg atc gct    1104
Thr Pro His Gly Gly Arg Val Asn Cys His Arg Asp His Arg Ile Ala
        355                 360                 365 atg gcg ttt tca atc ctg gga ctg aga gtg gac ggg att acc ctc gac    1152
Met Ala Phe Ser Ile Leu Gly Leu Arg Val Asp Gly Ile Thr Leu Asp
370                 375                 380 gac cct caa tgc gtc ggg aag acc ttt cct ggc ttc ttc gac tac ctt    1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag            1242
Gly Arg Leu Phe Pro Glu Lys Ala Leu Thr Leu Pro Gly
                405                 410 gg                                                                 1244

<210> SEQ ID NO 25
<211> LENGTH: 413
<212> TYPE: PRT
<213> ORGANISM: Artificial Sequence
<220> FEATURE:
<223> OTHER INFORMATION: GRG23(L3P1.F18)

<400> SEQUENCE: 25

Met Glu Thr Asp Arg Leu Val Ile Pro Gly Ser Lys Ser Ile Thr Asn
1               5                   10                  15

Arg Ala Leu Leu Leu Ala Ala Ala Ala Lys Gly Thr Ser Val Leu Val
            20                  25                  30

Arg Pro Leu Val Ser Ala Asp Thr Ser Ala Phe Lys Thr Ala Ile Gln
        35                  40                  45

Ala Leu Gly Ala Asn Val Ser Ala Asp Gly Asp Asn Trp Val Val Glu
    50                  55                  60

Gly Leu Gly Gln Ala Pro His Leu Asp Ala Asp Ile Trp Cys Glu Asp
65                  70                  75                  80

Ala Gly Thr Val Ala Arg Phe Leu Pro Pro Phe Val Ala Ala Gly Gln
                85                  90                  95

Gly Lys Phe Thr Val Asp Gly Ser Glu Gln Leu Arg Arg Arg Pro Leu
            100                 105                 110

Arg Pro Leu Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Leu Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ala Ser Ala Val Ser Gly Arg Ser Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Pro Asn Ser
            260                 265                 270

Val Ile Ile Ser Gly Pro Glu Arg Leu Asn Gly Asp Ile Glu Val Asp
```

```
                275                 280                 285
Met Gly Glu Ile Ser Asp Thr Phe Met Thr Leu Ala Ala Ile Ala Pro
            290                 295                 300
Leu Ala Asp Gly Pro Ile Thr Ile Thr Asn Ile Gly His Ala Arg Leu
305                 310                 315                 320
Lys Glu Ser Asp Arg Ile Ser Ala Met Glu Thr Asn Leu Arg Thr Leu
                325                 330                 335
Gly Val Gln Thr Asp Val Gly His Asp Trp Met Arg Ile Tyr Pro Ser
                340                 345                 350
Thr Pro His Gly Gly Arg Val Asn Cys His Arg Asp His Arg Ile Ala
                355                 360                 365
Met Ala Phe Ser Ile Leu Gly Leu Arg Val Asp Gly Ile Thr Leu Asp
            370                 375                 380
Asp Pro Gln Cys Val Gly Lys Thr Phe Pro Gly Phe Phe Asp Tyr Leu
385                 390                 395                 400
Gly Arg Leu Phe Pro Glu Lys Ala Leu Thr Leu Pro Gly
                405                 410

<210> SEQ ID NO 26
<211> LENGTH: 1244
<212> TYPE: DNA
<213> ORGANISM: Artificial Sequence
<220> FEATURE:
<223> OTHER INFORMATION: grg23(L3P1.O23)
<221> NAME/KEY: CDS
<222> LOCATION: (1)...(1242)

<400> SEQUENCE: 26 atg gaa act gat cac ctt gtg atc cca gga tcg aaa agc atc acc aac      48
Met Glu Thr Asp His Leu Val Ile Pro Gly Ser Lys Ser Ile Thr Asn
 1               5                  10                  15 cgg gcg ttg ctt ttg gct gcc gca gcg aag ggc acg tcg gtc ctg gtg      96
Arg Ala Leu Leu Leu Ala Ala Ala Ala Lys Gly Thr Ser Val Leu Val
                20                  25                  30 aga cca ttg gtc agc gcc gat acc tca gca ttc aaa act gca atc cag     144
Arg Pro Leu Val Ser Ala Asp Thr Ser Ala Phe Lys Thr Ala Ile Gln
            35                  40                  45 gcc ctc ggt gcc aac gtc tca gcc gac ggt gac aat tgg gtc gtt gaa     192
Ala Leu Gly Ala Asn Val Ser Ala Asp Gly Asp Asn Trp Val Val Glu
        50                  55                  60 ggc ttg ggt cag gca ccc cac ctc gac gcc gac atc tgg tgc gag gac     240
Gly Leu Gly Gln Ala Pro His Leu Asp Ala Asp Ile Trp Cys Glu Asp
 65                  70                  75                  80 gca ggt act gtg gcc cgg ttc ctc cct cca ttc gta gcc gca ggt cag     288
Ala Gly Thr Val Ala Arg Phe Leu Pro Pro Phe Val Ala Ala Gly Gln
                 85                  90                  95 ggg aag ttc acc gtc gac gga tca gag cag ctg cgg cgg cgc ccg ctt     336
Gly Lys Phe Thr Val Asp Gly Ser Glu Gln Leu Arg Arg Arg Pro Leu
            100                 105                 110 cgg ccc ctg gtc gac ggc atc cgc cac ctg ggc gcc cgc gtc tcc tcc     384
Arg Pro Leu Val Asp Gly Ile Arg His Leu Gly Ala Arg Val Ser Ser
        115                 120                 125 gag cag ctg ccc ctt aca att gaa gcg agc ggg ctg gca ggc ggg gag     432
Glu Gln Leu Pro Leu Thr Ile Glu Ala Ser Gly Leu Ala Gly Gly Glu
    130                 135                 140 tac gaa att gaa gcc cat cag agc agc cag ttc gcc tcc ggc ctg atc     480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat     528
Met Ala Ala Pro Tyr Ala Arg Gln Gly Leu Arg Val Arg Ile Pro Asn
```

|  |  |  |  |  |  |  |  |  |  |  |  |  |  |  |  |
|---|---|---|---|---|---|---|---|---|---|---|---|---|---|---|---|
|  |  |  |  | 165 |  |  |  | 170 |  |  |  | 175 |  |  |  |
| ccc | gtg | tca | cag | ccc | tac | ctc | acg | atg | aca | ctg | cgg | atg | atg | agg | gac | 576 |
| Pro | Val | Ser | Gln | Pro | Tyr | Leu | Thr | Met | Thr | Leu | Arg | Met | Met | Arg | Asp |  |
|  |  |  | 180 |  |  |  |  | 185 |  |  |  |  | 190 |  |  |  |
| ttc | ggc | ctt | gag | acc | agc | acc | gac | gga | gcc | acc | gtc | agc | gtc | cct | cca | 624 |
| Phe | Gly | Leu | Glu | Thr | Ser | Thr | Asp | Gly | Ala | Thr | Val | Ser | Val | Pro | Pro |  |
|  |  | 195 |  |  |  |  | 200 |  |  |  |  | 205 |  |  |  |  |
| ggg | cgc | tac | aca | gcc | cgg | cgg | tat | gaa | ata | gaa | ccg | gat | gcg | tca | act | 672 |
| Gly | Arg | Tyr | Thr | Ala | Arg | Arg | Tyr | Glu | Ile | Glu | Pro | Asp | Ala | Ser | Thr |  |
| 210 |  |  |  |  | 215 |  |  |  |  | 220 |  |  |  |  |  |  |
| gcg | tcg | tac | ttc | gcc | gcc | gct | tcc | gcc | gtc | tct | ggc | agg | agc | ttc | gaa | 720 |
| Ala | Ser | Tyr | Phe | Ala | Ala | Ala | Ser | Ala | Val | Ser | Gly | Arg | Ser | Phe | Glu |  |
| 225 |  |  |  | 230 |  |  |  |  | 235 |  |  |  |  | 240 |  |  |
| ttt | caa | ggc | ctt | ggc | aca | gac | agc | atc | caa | ggc | gac | acg | tca | ttt | ttc | 768 |
| Phe | Gln | Gly | Leu | Gly | Thr | Asp | Ser | Ile | Gln | Gly | Asp | Thr | Ser | Phe | Phe |  |
|  |  |  | 245 |  |  |  |  | 250 |  |  |  |  | 255 |  |  |  |
| aat | gta | ctt | ggg | cgg | ctc | ggt | gcg | gag | gtc | cac | tgg | gca | ccc | aac | tcg | 816 |
| Asn | Val | Leu | Gly | Arg | Leu | Gly | Ala | Glu | Val | His | Trp | Ala | Pro | Asn | Ser |  |
|  |  | 260 |  |  |  |  | 265 |  |  |  |  | 270 |  |  |  |  |
| gtc | acc | ata | tct | gga | ccg | gaa | agg | ctg | aac | ggc | gac | att | gaa | gtg | gat | 864 |
| Val | Thr | Ile | Ser | Gly | Pro | Glu | Arg | Leu | Asn | Gly | Asp | Ile | Glu | Val | Asp |  |
|  | 275 |  |  |  |  | 280 |  |  |  |  | 285 |  |  |  |  |  |
| atg | ggc | gag | att | tcg | gac | acc | ttc | atg | aca | ctc | gcg | gcg | att | gcc | cct | 912 |
| Met | Gly | Glu | Ile | Ser | Asp | Thr | Phe | Met | Thr | Leu | Ala | Ala | Ile | Ala | Pro |  |
| 290 |  |  |  |  | 295 |  |  |  |  | 300 |  |  |  |  |  |  |
| ttg | gcc | gat | gga | ccc | atc | acg | ata | acc | aac | att | ggt | cat | gca | cgg | ttg | 960 |
| Leu | Ala | Asp | Gly | Pro | Ile | Thr | Ile | Thr | Asn | Ile | Gly | His | Ala | Arg | Leu |  |
| 305 |  |  |  | 310 |  |  |  |  | 315 |  |  |  |  | 320 |  |  |
| aag | gaa | tcc | gac | cgc | atc | tca | gcg | atg | gaa | acc | aac | ctg | cgc | acg | ctc | 1008 |
| Lys | Glu | Ser | Asp | Arg | Ile | Ser | Ala | Met | Glu | Thr | Asn | Leu | Arg | Thr | Leu |  |
|  |  |  | 325 |  |  |  |  | 330 |  |  |  |  | 335 |  |  |  |
| ggt | gta | caa | acc | gac | gtc | gga | cac | gac | tgg | atg | aga | atc | tac | ccc | tct | 1056 |
| Gly | Val | Gln | Thr | Asp | Val | Gly | His | Asp | Trp | Met | Arg | Ile | Tyr | Pro | Ser |  |
|  |  | 340 |  |  |  |  | 345 |  |  |  |  | 350 |  |  |  |  |
| acc | ccg | cac | ggc | ggt | aga | gtg | aat | tgc | cac | cgg | gac | cac | agg | atc | gct | 1104 |
| Thr | Pro | His | Gly | Gly | Arg | Val | Asn | Cys | His | Arg | Asp | His | Arg | Ile | Ala |  |
|  | 355 |  |  |  |  | 360 |  |  |  |  | 365 |  |  |  |  |  |
| atg | gcg | ttt | tca | atc | ctg | gga | ctg | aga | gtg | gac | ggg | att | acc | ctc | gac | 1152 |
| Met | Ala | Phe | Ser | Ile | Leu | Gly | Leu | Arg | Val | Asp | Gly | Ile | Thr | Leu | Asp |  |
| 370 |  |  |  |  | 375 |  |  |  |  | 380 |  |  |  |  |  |  |
| gac | cct | caa | tgc | gtc | ggg | aag | acc | ttt | cct | ggc | ttc | ttc | gac | tac | ctt | 1200 |
| Asp | Pro | Gln | Cys | Val | Gly | Lys | Thr | Phe | Pro | Gly | Phe | Phe | Asp | Tyr | Leu |  |
| 385 |  |  |  | 390 |  |  |  |  | 395 |  |  |  |  | 400 |  |  |
| gga | cgc | ctt | ttc | ccc | gaa | aag | gcg | ctt | acg | ctt | ccc | ggc | tag |  |  | 1242 |
| Gly | Arg | Leu | Phe | Pro | Glu | Lys | Ala | Leu | Thr | Leu | Pro | Gly |  |  |  |  |
|  |  |  | 405 |  |  |  |  | 410 |  |  |  |  |  |  |  |  |
| gg |  |  |  |  |  |  |  |  |  |  |  |  |  |  |  | 1244 |

<210> SEQ ID NO 27
<211> LENGTH: 413
<212> TYPE: PRT
<213> ORGANISM: Artificial Sequence
<220> FEATURE:
<223> OTHER INFORMATION: GRG23(L3P1.O23)

<400> SEQUENCE: 27

Met Glu Thr Asp His Leu Val Ile Pro Gly Ser Lys Ser Ile Thr Asn
 1               5                  10                  15

Arg Ala Leu Leu Leu Ala Ala Ala Lys Gly Thr Ser Val Leu Val
            20                  25                  30

```
Arg Pro Leu Val Ser Ala Asp Thr Ser Ala Phe Lys Thr Ala Ile Gln
         35                  40                  45

Ala Leu Gly Ala Asn Val Ser Ala Asp Gly Asp Asn Trp Val Val Glu
 50                  55                  60

Gly Leu Gly Gln Ala Pro His Leu Asp Ala Asp Ile Trp Cys Glu Asp
 65                  70                  75                  80

Ala Gly Thr Val Ala Arg Phe Leu Pro Pro Phe Val Ala Ala Gly Gln
                 85                  90                  95

Gly Lys Phe Thr Val Asp Gly Ser Glu Gln Leu Arg Arg Arg Pro Leu
             100                 105                 110

Arg Pro Leu Val Asp Gly Ile Arg His Leu Gly Ala Arg Val Ser Ser
         115                 120                 125

Glu Gln Leu Pro Leu Thr Ile Glu Ala Ser Gly Leu Ala Gly Gly Glu
130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                 165                 170                 175

Pro Val Ser Gln Pro Tyr Leu Thr Met Thr Leu Arg Met Met Arg Asp
             180                 185                 190

Phe Gly Leu Glu Thr Ser Thr Asp Gly Ala Thr Val Ser Val Pro Pro
         195                 200                 205

Gly Arg Tyr Thr Ala Arg Arg Tyr Glu Ile Glu Pro Asp Ala Ser Thr
210                 215                 220

Ala Ser Tyr Phe Ala Ala Ser Ala Val Ser Gly Arg Ser Phe Glu
225                 230                 235                 240

Phe Gln Gly Leu Gly Thr Asp Ser Ile Gln Gly Asp Thr Ser Phe Phe
                 245                 250                 255

Asn Val Leu Gly Arg Leu Gly Ala Glu Val His Trp Ala Pro Asn Ser
             260                 265                 270

Val Thr Ile Ser Gly Pro Glu Arg Leu Asn Gly Asp Ile Glu Val Asp
         275                 280                 285

Met Gly Glu Ile Ser Asp Thr Phe Met Thr Leu Ala Ala Ile Ala Pro
290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Thr Asn Leu Arg Thr Leu
                 325                 330                 335

Gly Val Gln Thr Asp Val Gly His Asp Trp Met Arg Ile Tyr Pro Ser
             340                 345                 350

Thr Pro His Gly Gly Arg Val Asn Cys His Arg Asp His Arg Ile Ala
         355                 360                 365

Met Ala Phe Ser Ile Leu Gly Leu Arg Val Asp Gly Ile Thr Leu Asp
370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                 405                 410

<210> SEQ ID NO 28
<211> LENGTH: 1244
<212> TYPE: DNA
<213> ORGANISM: Artificial Sequence
<220> FEATURE:
<223> OTHER INFORMATION: grg23(ace3) variant sequence (grg23(ace3)
      R173K)
```

<221> NAME/KEY: CDS
<222> LOCATION: (1)...(1242)

<400> SEQUENCE: 28

```
atg gaa act gat cgc ctt gtg atc cca gga tcg aaa agc atc acc aac      48
Met Glu Thr Asp Arg Leu Val Ile Pro Gly Ser Lys Ser Ile Thr Asn
 1               5                  10                  15 cgg gct ttg ctt ttg gct gcc gca gcg aag ggc acg tcg gtc ctg gtg      96
Arg Ala Leu Leu Leu Ala Ala Ala Ala Lys Gly Thr Ser Val Leu Val
             20                  25                  30 aga cca ttg gtc agc gcc gat acc tca gca ttc aaa act gca atc cag     144
Arg Pro Leu Val Ser Ala Asp Thr Ser Ala Phe Lys Thr Ala Ile Gln
         35                  40                  45 gcc ctc ggt gcc aac gtc tca gcc gac ggt gac gat tgg gtc gtt gaa     192
Ala Leu Gly Ala Asn Val Ser Ala Asp Gly Asp Asp Trp Val Val Glu
     50                  55                  60 ggc ctg ggt cag gca ccc aac ctc gac gcc gac atc tgg tgc gag gac     240
Gly Leu Gly Gln Ala Pro Asn Leu Asp Ala Asp Ile Trp Cys Glu Asp
 65                  70                  75                  80 gca ggt act gtg gcc cgg ttc ctc cct cca ttc gta gcc gca ggt cag     288
Ala Gly Thr Val Ala Arg Phe Leu Pro Pro Phe Val Ala Ala Gly Gln
                 85                  90                  95 ggg aag ttc acc gtc gac gga tca gag cag ctg cgc cgg cgc ccg ctt     336
Gly Lys Phe Thr Val Asp Gly Ser Glu Gln Leu Arg Arg Arg Pro Leu
            100                 105                 110 cgg ccc gtg gtc gac ggc atc cgc cac ctg ggc gcc cgc gtc tcc tcc     384
Arg Pro Val Val Asp Gly Ile Arg His Leu Gly Ala Arg Val Ser Ser
        115                 120                 125 gag cag ctg ccc ctt aca att gaa gcg agc ggg ctg gca ggc ggg gag     432
Glu Gln Leu Pro Leu Thr Ile Glu Ala Ser Gly Leu Ala Gly Gly Glu
    130                 135                 140 tac gaa att gaa gcc cat cag agc agc cag ttc gcc tcc ggc ctg atc     480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg aag ata cca aat     528
Met Ala Ala Pro Tyr Ala Arg Gln Gly Leu Arg Val Lys Ile Pro Asn
                165                 170                 175 ccc gtg tca cag ccc tac ctc acg atg aca ctg cgg atg atg agg gac     576
Pro Val Ser Gln Pro Tyr Leu Thr Met Thr Leu Arg Met Met Arg Asp
            180                 185                 190 ttc ggc att gag acc agc acc gac gga gcc acc gtc agc gtc cct cca     624
Phe Gly Ile Glu Thr Ser Thr Asp Gly Ala Thr Val Ser Val Pro Pro
        195                 200                 205 ggg cgc tac aca gcc cgg cgg tat gaa ata gaa ccg gat gcg tca act     672
Gly Arg Tyr Thr Ala Arg Arg Tyr Glu Ile Glu Pro Asp Ala Ser Thr
    210                 215                 220 gcg tcg tac ttc gcc gcc gct tcc gcc gtc tct ggc agg cgc ttc gaa     720
Ala Ser Tyr Phe Ala Ala Ala Ser Ala Val Ser Gly Arg Arg Phe Glu
225                 230                 235                 240 ttt caa ggc ctt ggc aca gac agc atc caa ggc gac acg tca ttc ttc     768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca tcc aac tcg     816
Asn Val Leu Gly Arg Leu Gly Ala Glu Val His Trp Ala Ser Asn Ser
            260                 265                 270 gtc acc ata cgg gga ccg gaa agg ctg acc ggc gac att gaa gtg gat     864
Val Thr Ile Arg Gly Pro Glu Arg Leu Thr Gly Asp Ile Glu Val Asp
        275                 280                 285 atg ggc gag att tcg gac acc ttc atg aca ctc gcg gcg att gcc cct     912
Met Gly Glu Ile Ser Asp Thr Phe Met Thr Leu Ala Ala Ile Ala Pro
    290                 295                 300
```

| | | | | | | | | | | | | | | | |
|---|---|---|---|---|---|---|---|---|---|---|---|---|---|---|---|
| ttg | gcc | gat | gga | ccc | atc | acg | ata | acc | aac | att | ggt | cat | gca | cgg | ttg | 960 |
| Leu | Ala | Asp | Gly | Pro | Ile | Thr | Ile | Thr | Asn | Ile | Gly | His | Ala | Arg | Leu | |
| 305 | | | | 310 | | | | | 315 | | | | | 320 | | |

| aag | gaa | tcc | gac | cgc | atc | tca | gcg | atg | gaa | agc | aac | ctg | cgc | acg | ctc | 1008 |
|---|---|---|---|---|---|---|---|---|---|---|---|---|---|---|---|---|
| Lys | Glu | Ser | Asp | Arg | Ile | Ser | Ala | Met | Glu | Ser | Asn | Leu | Arg | Thr | Leu | |
| | | | | 325 | | | | | 330 | | | | | 335 | | |

| ggt | gta | caa | acc | gac | gtc | gga | cac | gac | tgg | atg | aga | atc | tac | ccc | tct | 1056 |
|---|---|---|---|---|---|---|---|---|---|---|---|---|---|---|---|---|
| Gly | Val | Gln | Thr | Asp | Val | Gly | His | Asp | Trp | Met | Arg | Ile | Tyr | Pro | Ser | |
| | | | 340 | | | | | 345 | | | | | 350 | | | |

| acc | ccg | cac | ggc | ggt | aga | gtg | aat | tgc | cac | cgg | gac | cac | agg | atc | gct | 1104 |
|---|---|---|---|---|---|---|---|---|---|---|---|---|---|---|---|---|
| Thr | Pro | His | Gly | Gly | Arg | Val | Asn | Cys | His | Arg | Asp | His | Arg | Ile | Ala | |
| | | | 355 | | | | | 360 | | | | | 365 | | | |

| atg | gcg | ttt | tca | atc | ctg | gga | ctg | aga | gtg | gac | ggg | att | acc | ctc | gac | 1152 |
|---|---|---|---|---|---|---|---|---|---|---|---|---|---|---|---|---|
| Met | Ala | Phe | Ser | Ile | Leu | Gly | Leu | Arg | Val | Asp | Gly | Ile | Thr | Leu | Asp | |
| 370 | | | | | 375 | | | | | 380 | | | | | | |

| gac | cct | caa | tgc | gtc | ggg | aag | acc | ttt | cct | ggc | ttc | ttc | gac | tac | ctt | 1200 |
|---|---|---|---|---|---|---|---|---|---|---|---|---|---|---|---|---|
| Asp | Pro | Gln | Cys | Val | Gly | Lys | Thr | Phe | Pro | Gly | Phe | Phe | Asp | Tyr | Leu | |
| 385 | | | | 390 | | | | | 395 | | | | | 400 | | |

| gga | cgc | ctt | ttc | ccc | gaa | aag | gcg | ctt | acg | ctc | ccc | ggc | tag | | | 1242 |
|---|---|---|---|---|---|---|---|---|---|---|---|---|---|---|---|---|
| Gly | Arg | Leu | Phe | Pro | Glu | Lys | Ala | Leu | Thr | Leu | Pro | Gly | | | | |
| | | | | 405 | | | | | 410 | | | | | | | |

| gg | | | | | | | | | | | | | | | | 1244 |
|---|---|---|---|---|---|---|---|---|---|---|---|---|---|---|---|---|

<210> SEQ ID NO 29
<211> LENGTH: 413
<212> TYPE: PRT
<213> ORGANISM: Artificial Sequence
<220> FEATURE:
<223> OTHER INFORMATION: GRG23(ace3) variant sequence (GRG23(ace3) R173K)

<400> SEQUENCE: 29

Met Glu Thr Asp Arg Leu Val Ile Pro Gly Ser Lys Ser Ile Thr Asn
1               5                   10                  15

Arg Ala Leu Leu Leu Ala Ala Ala Lys Gly Thr Ser Val Leu Val
            20                  25                  30

Arg Pro Leu Val Ser Ala Asp Thr Ser Ala Phe Lys Thr Ala Ile Gln
        35                  40                  45

Ala Leu Gly Ala Asn Val Ser Ala Asp Gly Asp Asp Trp Val Val Glu
    50                  55                  60

Gly Leu Gly Gln Ala Pro Asn Leu Asp Ala Asp Ile Trp Cys Glu Asp
65                  70                  75                  80

Ala Gly Thr Val Ala Arg Phe Leu Pro Pro Phe Val Ala Ala Gly Gln
                85                  90                  95

Gly Lys Phe Thr Val Asp Gly Ser Glu Gln Leu Arg Arg Pro Leu
                100                 105                 110

Arg Pro Val Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Lys Ile Pro Asn
                165                 170                 175

Pro Val Ser Gln Pro Tyr Leu Thr Met Thr Leu Arg Met Met Arg Asp
            180                 185                 190

Phe Gly Ile Glu Thr Ser Thr Asp Gly Ala Thr Val Ser Val Pro Pro
        195                 200                 205

```
Gly Arg Tyr Thr Ala Arg Arg Tyr Glu Ile Glu Pro Asp Ala Ser Thr
    210                 215                 220

Ala Ser Tyr Phe Ala Ala Ser Ala Val Ser Gly Arg Arg Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Ser Asn Ser
                260                 265                 270

Val Thr Ile Arg Gly Pro Glu Arg Leu Thr Gly Asp Ile Glu Val Asp
            275                 280                 285

Met Gly Glu Ile Ser Asp Thr Phe Met Thr Leu Ala Ala Ile Ala Pro
    290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Ser Asn Leu Arg Thr Leu
                325                 330                 335

Gly Val Gln Thr Asp Val Gly His Asp Trp Met Arg Ile Tyr Pro Ser
                340                 345                 350

Thr Pro His Gly Gly Arg Val Asn Cys His Arg Asp His Arg Ile Ala
            355                 360                 365

Met Ala Phe Ser Ile Leu Gly Leu Arg Val Asp Gly Ile Thr Leu Asp
    370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410
```

<210> SEQ ID NO 30
<211> LENGTH: 1244
<212> TYPE: DNA
<213> ORGANISM: Artificial Sequence
<220> FEATURE:
<223> OTHER INFORMATION: grg23(ace3) variant sequence (grg23(ace3) G169V/L170V)
<221> NAME/KEY: CDS
<222> LOCATION: (1)...(1242)

<400> SEQUENCE: 30

```
atg gaa act gat cgc ctt gtg atc cca gga tcg aaa agc atc acc aac      48
Met Glu Thr Asp Arg Leu Val Ile Pro Gly Ser Lys Ser Ile Thr Asn
1               5                   10                  15 cgg gct ttg ctt ttg gct gcc gca gcg aag ggc acg tcg gtc ctg gtg      96
Arg Ala Leu Leu Leu Ala Ala Ala Ala Lys Gly Thr Ser Val Leu Val
                20                  25                  30 aga cca ttg gtc agc gcc gat acc tca gca ttc aaa act gca atc cag     144
Arg Pro Leu Val Ser Ala Asp Thr Ser Ala Phe Lys Thr Ala Ile Gln
            35                  40                  45 gcc ctc ggt gcc aac gtc tca gcc gac ggt gac gat tgg gtc gtt gaa     192
Ala Leu Gly Ala Asn Val Ser Ala Asp Gly Asp Asp Trp Val Val Glu
        50                  55                  60 ggc ctg ggt cag gca ccc aac ctc gac gcc gac atc tgg tgc gag gac     240
Gly Leu Gly Gln Ala Pro Asn Leu Asp Ala Asp Ile Trp Cys Glu Asp
65                  70                  75                  80 gca ggt act gtg gcc cgg ttc ctc cct cca ttc gta gcc gca ggt cag     288
Ala Gly Thr Val Ala Arg Phe Leu Pro Pro Phe Val Ala Ala Gly Gln
                85                  90                  95 ggg aag ttc acc gtc gac gga tca gag cag ctg cgg cgg cgc ccg ctt     336
Gly Lys Phe Thr Val Asp Gly Ser Glu Gln Leu Arg Arg Arg Pro Leu
                100                 105                 110
```

```
cgg ccc gtg gtc gac ggc atc cgc cac ctg ggc gcc cgc gtc tcc tcc      384
Arg Pro Val Val Asp Gly Ile Arg His Leu Gly Ala Arg Val Ser Ser
        115                 120                 125 gag cag ctg ccc ctt aca att gaa gcg agc ggg ctg gca ggc ggg gag      432
Glu Gln Leu Pro Leu Thr Ile Glu Ala Ser Gly Leu Ala Gly Gly Glu
130                 135                 140 tac gaa att gaa gcc cat cag agc agc cag ttc gcc tcc ggc ctg atc      480
Tyr Glu Ile Glu Ala His Gln Ser Ser Gln Phe Ala Ser Gly Leu Ile
145                 150                 155                 160 atg gcc gcc ccg tac gcg aga caa gtc gtg cgt gtg aag ata cca aat      528
Met Ala Ala Pro Tyr Ala Arg Gln Val Val Arg Val Lys Ile Pro Asn
                165                 170                 175 ccc gtg tca cag ccc tac ctc acg atg aca ctg cgg atg atg agg gac      576
Pro Val Ser Gln Pro Tyr Leu Thr Met Thr Leu Arg Met Met Arg Asp
            180                 185                 190 ttc ggc att gag acc agc acc gac gga gcc acc gtc agc gtc cct cca      624
Phe Gly Ile Glu Thr Ser Thr Asp Gly Ala Thr Val Ser Val Pro Pro
        195                 200                 205 ggg cgc tac aca gcc cgg cgg tat gaa ata gaa ccg gat gcg tca act      672
Gly Arg Tyr Thr Ala Arg Arg Tyr Glu Ile Glu Pro Asp Ala Ser Thr
210                 215                 220 gcg tcg tac ttc gcc gcc gct tcc gcc gtc tct ggc agg cgc ttc gaa      720
Ala Ser Tyr Phe Ala Ala Ala Ser Ala Val Ser Gly Arg Arg Phe Glu
225                 230                 235                 240 ttt caa ggc ctt ggc aca gac agc atc caa ggc gac acg tca ttc ttc      768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca tcc aac tcg      816
Asn Val Leu Gly Arg Leu Gly Ala Glu Val His Trp Ala Ser Asn Ser
            260                 265                 270 gtc acc ata cgg gga ccg gaa agg ctg acc ggc gac att gaa gtg gat      864
Val Thr Ile Arg Gly Pro Glu Arg Leu Thr Gly Asp Ile Glu Val Asp
        275                 280                 285 atg ggc gag att tcg gac acc ttc atg aca ctc gcg gcg att gcc cct      912
Met Gly Glu Ile Ser Asp Thr Phe Met Thr Leu Ala Ala Ile Ala Pro
    290                 295                 300 ttg gcc gat gga ccc atc acg ata acc aac att ggt cat gca cgg ttg      960
Leu Ala Asp Gly Pro Ile Thr Ile Thr Asn Ile Gly His Ala Arg Leu
305                 310                 315                 320 aag gaa tcc gac cgc atc tca gcg atg gaa agc aac ctg cgc acg ctc     1008
Lys Glu Ser Asp Arg Ile Ser Ala Met Glu Ser Asn Leu Arg Thr Leu
                325                 330                 335 ggt gta caa acc gac gtc gga cac gac tgg atg aga atc tac ccc tct     1056
Gly Val Gln Thr Asp Val Gly His Asp Trp Met Arg Ile Tyr Pro Ser
            340                 345                 350 acc ccg cac ggc ggt aga gtg aat tgc cac cgg gac cac agg atc gct     1104
Thr Pro His Gly Gly Arg Val Asn Cys His Arg Asp His Arg Ile Ala
        355                 360                 365 atg gcg ttt tca atc ctg gga ctg aga gtg gac ggg att acc ctc gac     1152
Met Ala Phe Ser Ile Leu Gly Leu Arg Val Asp Gly Ile Thr Leu Asp
    370                 375                 380 gac cct caa tgc gtc ggg aag acc ttt cct ggc ttc ttc gac tac ctt     1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag             1242
Gly Arg Leu Phe Pro Glu Lys Ala Leu Thr Leu Pro Gly
                405                 410 gg                                                                  1244
```

-continued

```
<210> SEQ ID NO 31
<211> LENGTH: 413
<212> TYPE: PRT
<213> ORGANISM: Artificial Sequence
<220> FEATURE:
<223> OTHER INFORMATION: GRG23(ace3) variant sequence (GRG23(ace3)
      G169V/L170V)

<400> SEQUENCE: 31
```

Met Glu Thr Asp Arg Leu Val Ile Pro Gly Ser Lys Ser Ile Thr Asn
 1               5                  10                  15

Arg Ala Leu Leu Leu Ala Ala Ala Lys Gly Thr Ser Val Leu Val
             20                  25                  30

Arg Pro Leu Val Ser Ala Asp Thr Ser Ala Phe Lys Thr Ala Ile Gln
         35                  40                  45

Ala Leu Gly Ala Asn Val Ser Asp Gly Asp Trp Val Val Glu
     50                  55                  60

Gly Leu Gly Gln Ala Pro Asn Leu Asp Ala Asp Ile Trp Cys Glu Asp
 65                  70                  75                  80

Ala Gly Thr Val Ala Arg Phe Leu Pro Pro Phe Val Ala Ala Gly Gln
                 85                  90                  95

Gly Lys Phe Thr Val Asp Gly Ser Glu Gln Leu Arg Arg Pro Leu
            100                 105                 110

Arg Pro Val Val Asp Gly Ile Arg His Leu Gly Ala Arg Val Ser Ser
            115                 120                 125

Glu Gln Leu Pro Leu Thr Ile Glu Ala Ser Gly Leu Ala Gly Gly Glu
130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Val Val Arg Val Lys Ile Pro Asn
                165                 170                 175

Pro Val Ser Gln Pro Tyr Leu Thr Met Thr Leu Arg Met Met Arg Asp
            180                 185                 190

Phe Gly Ile Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ala Ser Ala Val Ser Gly Arg Arg Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Ser Asn Ser
            260                 265                 270

Val Thr Ile Arg Gly Pro Glu Arg Leu Thr Gly Asp Ile Glu Val Asp
        275                 280                 285

Met Gly Glu Ile Ser Asp Thr Phe Met Thr Leu Ala Ala Ile Ala Pro
    290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Ser Asn Leu Arg Thr Leu
                325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
        355                 360                 365

Met Ala Phe Ser Ile Leu Gly Leu Arg Val Asp Gly Ile Thr Leu Asp

```
                     370                 375                 380
Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410

<210> SEQ ID NO 32
<211> LENGTH: 1244
<212> TYPE: DNA
<213> ORGANISM: Artificial Sequence
<220> FEATURE:
<223> OTHER INFORMATION: grg23(ace3) variant sequence (grg23(ace3)
      R173Q)
<221> NAME/KEY: CDS
<222> LOCATION: (1)...(1242)

<400> SEQUENCE: 32 atg gaa act gat cgc ctt gtg atc cca gga tcg aaa agc atc acc aac     48
Met Glu Thr Asp Arg Leu Val Ile Pro Gly Ser Lys Ser Ile Thr Asn
 1               5                  10                  15 cgg gct ttg ctt ttg gct gcc gca gcg aag ggc acg tcg gtc ctg gtg     96
Arg Ala Leu Leu Leu Ala Ala Ala Ala Lys Gly Thr Ser Val Leu Val
                20                  25                  30 aga cca ttg gtc agc gcc gat acc tca gca ttc aaa act gca atc cag    144
Arg Pro Leu Val Ser Ala Asp Thr Ser Ala Phe Lys Thr Ala Ile Gln
            35                  40                  45 gcc ctc ggt gcc aac gtc tca gcc gac ggt gac gat tgg gtc gtt gaa    192
Ala Leu Gly Ala Asn Val Ser Ala Asp Gly Asp Asp Trp Val Val Glu
        50                  55                  60 ggc ctg ggt cag gca ccc aac ctc gac gcc gac atc tgg tgc gag gac    240
Gly Leu Gly Gln Ala Pro Asn Leu Asp Ala Asp Ile Trp Cys Glu Asp
 65                  70                  75                  80 gca ggt act gtg gcc cgg ttc ctc cct cca ttc gta gcc gca ggt cag    288
Ala Gly Thr Val Ala Arg Phe Leu Pro Pro Phe Val Ala Ala Gly Gln
                85                  90                  95 ggg aag ttc acc gtc gac gga tca gag cag ctg cgg cgg cgc ccg ctt    336
Gly Lys Phe Thr Val Asp Gly Ser Glu Gln Leu Arg Arg Arg Pro Leu
            100                 105                 110 cgg ccc gtg gtc gac ggc atc cgc cac ctg ggc gcc cgc gtc tcc tcc    384
Arg Pro Val Val Asp Gly Ile Arg His Leu Gly Ala Arg Val Ser Ser
        115                 120                 125 gag cag ctg ccc ctt aca att gaa gcg agc ggg ctg gca ggc ggg gag    432
Glu Gln Leu Pro Leu Thr Ile Glu Ala Ser Gly Leu Ala Gly Gly Glu
130                 135                 140 tac gaa att gaa gcc cat cag agc agc cag ttc gcc tcc ggc ctg atc    480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg caa ata cca aat    528
Met Ala Ala Pro Tyr Ala Arg Gln Gly Leu Arg Val Gln Ile Pro Asn
                165                 170                 175 ccc gtg tca cag ccc tac ctc acg atg aca ctg cgg atg atg agg gac    576
Pro Val Ser Gln Pro Tyr Leu Thr Met Thr Leu Arg Met Met Arg Asp
            180                 185                 190 ttc ggc att gag acc agc acc gac gga gcc acc gtc agc gtc cct cca    624
Phe Gly Ile Glu Thr Ser Thr Asp Gly Ala Thr Val Ser Val Pro Pro
        195                 200                 205 ggg cgc tac aca gcc cgg cgg tat gaa ata gaa ccg gat gcg tca act    672
Gly Arg Tyr Thr Ala Arg Arg Tyr Glu Ile Glu Pro Asp Ala Ser Thr
    210                 215                 220 gcg tcg tac ttc gcc gcc gct tcc gcc gtc tct ggc agg cgc ttc gaa    720
Ala Ser Tyr Phe Ala Ala Ala Ser Ala Val Ser Gly Arg Arg Phe Glu
225                 230                 235                 240
```

```
ttt caa ggc ctt ggc aca gac agc atc caa ggc gac acg tca ttc ttc    768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca tcc aac tcg    816
Asn Val Leu Gly Arg Leu Gly Ala Glu Val His Trp Ala Ser Asn Ser
            260                 265                 270 gtc acc ata cgg gga ccg gaa agg ctg acc ggc gac att gaa gtg gat    864
Val Thr Ile Arg Gly Pro Glu Arg Leu Thr Gly Asp Ile Glu Val Asp
        275                 280                 285 atg ggc gag att tcg gac acc ttc atg aca ctc gcg gcg att gcc cct    912
Met Gly Glu Ile Ser Asp Thr Phe Met Thr Leu Ala Ala Ile Ala Pro
    290                 295                 300 ttg gcc gat gga ccc atc acg ata acc aac att ggt cat gca cgg ttg    960
Leu Ala Asp Gly Pro Ile Thr Ile Thr Asn Ile Gly His Ala Arg Leu
305                 310                 315                 320 aag gaa tcc gac cgc atc tca gcg atg gaa agc aac ctg cgc acg ctc   1008
Lys Glu Ser Asp Arg Ile Ser Ala Met Glu Ser Asn Leu Arg Thr Leu
                325                 330                 335 ggt gta caa acc gac gtc gga cac gac tgg atg aga atc tac ccc tct   1056
Gly Val Gln Thr Asp Val Gly His Asp Trp Met Arg Ile Tyr Pro Ser
            340                 345                 350 acc ccg cac ggc ggt aga gtg aat tgc cac cgg gac cac agg atc gct   1104
Thr Pro His Gly Gly Arg Val Asn Cys His Arg Asp His Arg Ile Ala
        355                 360                 365 atg gcg ttt tca atc ctg gga ctg aga gtg gac ggg att acc ctc gac   1152
Met Ala Phe Ser Ile Leu Gly Leu Arg Val Asp Gly Ile Thr Leu Asp
    370                 375                 380 gac cct caa tgc gtc ggg aag acc ttt cct ggc ttc ttc gac tac ctt   1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag           1242
Gly Arg Leu Phe Pro Glu Lys Ala Leu Thr Leu Pro Gly
                405                 410 gg                                                                1244
```

<210> SEQ ID NO 33
<211> LENGTH: 413
<212> TYPE: PRT
<213> ORGANISM: Artificial Sequence
<220> FEATURE:
<223> OTHER INFORMATION: GRG23(ace3) variant sequence (GRG23(ace3) R173Q)

<400> SEQUENCE: 33

```
Met Glu Thr Asp Arg Leu Val Ile Pro Gly Ser Lys Ser Ile Thr Asn
 1               5                  10                  15

Arg Ala Leu Leu Leu Ala Ala Ala Lys Gly Thr Ser Val Leu Val
                20                  25                  30

Arg Pro Leu Val Ser Ala Asp Thr Ser Ala Phe Lys Thr Ala Ile Gln
            35                  40                  45

Ala Leu Gly Ala Asn Val Ser Ala Asp Gly Asp Trp Val Val Glu
        50                  55                  60

Gly Leu Gly Gln Ala Pro Asn Leu Asp Ala Asp Ile Trp Cys Glu Asp
65                  70                  75                  80

Ala Gly Thr Val Ala Arg Phe Leu Pro Pro Phe Val Ala Ala Gly Gln
                85                  90                  95

Gly Lys Phe Thr Val Asp Gly Ser Glu Gln Leu Arg Arg Arg Pro Leu
            100                 105                 110

Arg Pro Val Val Asp Gly Ile Arg His Leu Gly Ala Arg Val Ser Ser
```

```
                    115                 120                 125
Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Gln Ile Pro Asn
                165                 170                 175

Pro Val Ser Gln Pro Tyr Leu Thr Met Thr Leu Arg Met Met Arg Asp
            180                 185                 190

Phe Gly Ile Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ser Ala Val Ser Gly Arg Arg Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Ser Asn Ser
            260                 265                 270

Val Thr Ile Arg Gly Pro Glu Arg Leu Thr Gly Asp Ile Glu Val Asp
        275                 280                 285

Met Gly Glu Ile Ser Asp Thr Phe Met Thr Leu Ala Ala Ile Ala Pro
    290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Ser Asn Leu Arg Thr Leu
                325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
        355                 360                 365

Met Ala Phe Ser Ile Leu Gly Leu Arg Val Asp Gly Ile Thr Leu Asp
    370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410

<210> SEQ ID NO 34
<211> LENGTH: 1244
<212> TYPE: DNA
<213> ORGANISM: Artificial Sequence
<220> FEATURE:
<223> OTHER INFORMATION: grg23(ace3) variant sequence (grg23(ace3)
      I174V)
<221> NAME/KEY: CDS
<222> LOCATION: (1)...(1242)

<400> SEQUENCE: 34 atg gaa act gat cgc ctt gtg atc cca gga tcg aaa agc atc acc aac      48
Met Glu Thr Asp Arg Leu Val Ile Pro Gly Ser Lys Ser Ile Thr Asn
 1               5                  10                  15 cgg gct ttg ctt ttg gct gcc gca gcg aag ggc acg tcg gtc ctg gtg      96
Arg Ala Leu Leu Leu Ala Ala Ala Ala Lys Gly Thr Ser Val Leu Val
                20                  25                  30 aga cca ttg gtc agc gcc gat acc tca gca ttc aaa act gca atc cag     144
Arg Pro Leu Val Ser Ala Asp Thr Ser Ala Phe Lys Thr Ala Ile Gln
            35                  40                  45
```

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| gcc   | ctc   | ggt   | gcc   | aac   | gtc   | tca   | gcc   | gac   | ggt   | gac   | gat   | tgg   | gtc   | gtt   | gaa   | 192  |
| Ala   | Leu   | Gly   | Ala   | Asn   | Val   | Ser   | Ala   | Asp   | Gly   | Asp   | Asp   | Trp   | Val   | Val   | Glu   |      |
|       | 50    |       |       |       | 55    |       |       |       | 60    |       |       |       |       |       |       |      | ggc ctg ggt cag gca ccc aac ctc gac gcc gac atc tgg tgc gag gac   240
Gly Leu Gly Gln Ala Pro Asn Leu Asp Ala Asp Ile Trp Cys Glu Asp
 65              70                  75                  80 gca ggt act gtg gcc cgg ttc ctc cct cca ttc gta gcc gca ggt cag   288
Ala Gly Thr Val Ala Arg Phe Leu Pro Pro Phe Val Ala Ala Gly Gln
                 85                  90                  95 ggg aag ttc acc gtc gac gga tca gag cag ctg cgg cgc ccg ctt       336
Gly Lys Phe Thr Val Asp Gly Ser Glu Gln Leu Arg Arg Pro Leu
             100                 105                 110 cgg ccc gtg gtc gac ggc atc cgc cac ctg ggc gcc cgc gtc tcc tcc   384
Arg Pro Val Val Asp Gly Ile Arg His Leu Gly Ala Arg Val Ser Ser
             115                 120                 125 gag cag ctg ccc ctt aca att gaa gcg agc ggg ctg gca ggc ggg gag   432
Glu Gln Leu Pro Leu Thr Ile Glu Ala Ser Gly Leu Ala Gly Gly Glu
130                 135                 140 tac gaa att gaa gcc cat cag agc agc cag ttc gcc tcc ggc ctg atc   480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg gtc cca aat   528
Met Ala Ala Pro Tyr Ala Arg Gln Gly Leu Arg Val Arg Val Pro Asn
                 165                 170                 175 ccc gtg tca cag ccc tac ctc acg atg aca ctg cgg atg atg agg gac   576
Pro Val Ser Gln Pro Tyr Leu Thr Met Thr Leu Arg Met Met Arg Asp
             180                 185                 190 ttc ggc att gag acc agc acc gac gga gcc acc gtc agc gtc cct cca   624
Phe Gly Ile Glu Thr Ser Thr Asp Gly Ala Thr Val Ser Val Pro Pro
             195                 200                 205 ggg cgc tac aca gcc cgg cgg tat gaa ata gaa ccg gat gcg tca act   672
Gly Arg Tyr Thr Ala Arg Arg Tyr Glu Ile Glu Pro Asp Ala Ser Thr
210                 215                 220 gcg tcg tac ttc gcc gcc gct tcc gcc gtc tct ggc agg cgc ttc gaa   720
Ala Ser Tyr Phe Ala Ala Ala Ser Ala Val Ser Gly Arg Arg Phe Glu
225                 230                 235                 240 ttt caa ggc ctt ggc aca gac agc atc caa ggc gac acg tca ttc ttc   768
Phe Gln Gly Leu Gly Thr Asp Ser Ile Gln Gly Asp Thr Ser Phe Phe
                 245                 250                 255 aat gta ctt ggg cgg ctc ggt gcg gag gtc cac tgg gca tcc aac tcg   816
Asn Val Leu Gly Arg Leu Gly Ala Glu Val His Trp Ala Ser Asn Ser
             260                 265                 270 gtc acc ata cgg gga ccg gaa agg ctg acc ggc gac att gaa gtg gat   864
Val Thr Ile Arg Gly Pro Glu Arg Leu Thr Gly Asp Ile Glu Val Asp
             275                 280                 285 atg ggc gag att tcg gac acc ttc atg aca ctc gcg gcg att gcc cct   912
Met Gly Glu Ile Ser Asp Thr Phe Met Thr Leu Ala Ala Ile Ala Pro
             290                 295                 300 ttg gcc gat gga ccc atc acg ata acc aac att ggt cat gca cgg ttg   960
Leu Ala Asp Gly Pro Ile Thr Ile Thr Asn Ile Gly His Ala Arg Leu
305                 310                 315                 320 aag gaa tcc gac cgc atc tca gcg atg gaa agc aac ctg cgc acg ctc  1008
Lys Glu Ser Asp Arg Ile Ser Ala Met Glu Ser Asn Leu Arg Thr Leu
                 325                 330                 335 ggt gta caa acc gac gtc gga cac gac tgg atg aga atc tac ccc tct  1056
Gly Val Gln Thr Asp Val Gly His Asp Trp Met Arg Ile Tyr Pro Ser
             340                 345                 350 acc ccg cac ggc ggt aga gtg aat tgc cac cgg gac cac agg atc gct  1104
Thr Pro His Gly Gly Arg Val Asn Cys His Arg Asp His Arg Ile Ala
             355                 360                 365

```
atg gcg ttt tca atc ctg gga ctg aga gtg gac ggg att acc ctc gac    1152
Met Ala Phe Ser Ile Leu Gly Leu Arg Val Asp Gly Ile Thr Leu Asp
370                 375                 380 gac cct caa tgc gtc ggg aag acc ttt cct ggc ttc ttc gac tac ctt    1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag            1242
Gly Arg Leu Phe Pro Glu Lys Ala Leu Thr Leu Pro Gly
                405                 410 gg                                                                  1244

<210> SEQ ID NO 35
<211> LENGTH: 413
<212> TYPE: PRT
<213> ORGANISM: Artificial Sequence
<220> FEATURE:
<223> OTHER INFORMATION: GRG23(ace3) variant sequence (GRG23(ace3)
      I174V)

<400> SEQUENCE: 35

Met Glu Thr Asp Arg Leu Val Ile Pro Gly Ser Lys Ser Ile Thr Asn
1               5                   10                  15

Arg Ala Leu Leu Leu Ala Ala Ala Lys Gly Thr Ser Val Leu Val
            20                  25                  30

Arg Pro Leu Val Ser Ala Asp Thr Ser Ala Phe Lys Thr Ala Ile Gln
            35                  40                  45

Ala Leu Gly Ala Asn Val Ser Ala Asp Gly Asp Asp Trp Val Val Glu
        50                  55                  60

Gly Leu Gly Gln Ala Pro Asn Leu Asp Ala Asp Ile Trp Cys Glu Asp
65                  70                  75                  80

Ala Gly Thr Val Ala Arg Phe Leu Pro Pro Phe Val Ala Ala Gly Gln
                85                  90                  95

Gly Lys Phe Thr Val Asp Gly Ser Glu Gln Leu Arg Arg Arg Pro Leu
            100                 105                 110

Arg Pro Val Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Val Pro Asn
                165                 170                 175

Pro Val Ser Gln Pro Tyr Leu Thr Met Thr Leu Arg Met Met Arg Asp
            180                 185                 190

Phe Gly Ile Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ala Ser Ala Val Ser Gly Arg Arg Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Ser Asn Ser
            260                 265                 270

Val Thr Ile Arg Gly Pro Glu Arg Leu Thr Gly Asp Ile Glu Val Asp
        275                 280                 285
```

```
Met Gly Glu Ile Ser Asp Thr Phe Met Thr Leu Ala Ala Ile Ala Pro
    290             295             300
Leu Ala Asp Gly Pro Ile Thr Ile Thr Asn Ile Gly His Ala Arg Leu
305                 310             315                 320
Lys Glu Ser Asp Arg Ile Ser Ala Met Glu Ser Asn Leu Arg Thr Leu
            325             330                 335
Gly Val Gln Thr Asp Val Gly His Asp Trp Met Arg Ile Tyr Pro Ser
            340             345             350
Thr Pro His Gly Gly Arg Val Asn Cys His Arg Asp His Arg Ile Ala
        355             360             365
Met Ala Phe Ser Ile Leu Gly Leu Arg Val Asp Gly Ile Thr Leu Asp
    370             375             380
Asp Pro Gln Cys Val Gly Lys Thr Phe Pro Gly Phe Phe Asp Tyr Leu
385                 390             395             400
Gly Arg Leu Phe Pro Glu Lys Ala Leu Thr Leu Pro Gly
                405             410
```